US008841291B2

(12) United States Patent
McQuire et al.

(10) Patent No.: US 8,841,291 B2
(45) Date of Patent: Sep. 23, 2014

(54) SELECTIVE HYDROXAMIC ACID BASED MMP-12 AND MMP-13 INHIBITORS

(71) Applicants: Leslie Wighton McQuire, Cambridge, MA (US); Michael Shultz, Cambridge, MA (US); Ruben Alberto Tommasi, Cambridge, MA (US); Sven Weiler, Basel (CH)

(72) Inventors: Leslie Wighton McQuire, Cambridge, MA (US); Olivier Rogel, Basel (CH); Michael Shultz, Cambridge, MA (US); Ruben Alberto Tommasi, Cambridge, MA (US); Sven Weiler, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/042,652

(22) Filed: Sep. 30, 2013

(65) Prior Publication Data
US 2014/0031399 A1 Jan. 30, 2014

Related U.S. Application Data

(63) Continuation of application No. 13/003,406, filed as application No. PCT/EP2009/058932 on Jul. 13, 2009, now abandoned.

(60) Provisional application No. 61/080,472, filed on Jul. 14, 2008.

(51) Int. Cl.
*A01N 43/00* (2006.01)
*A61K 31/55* (2006.01)

(52) U.S. Cl.
USPC ...... 514/217.11; 514/357; 514/575; 546/337; 562/623

(58) Field of Classification Search
None
See application file for complete search history.

(56) References Cited

U.S. PATENT DOCUMENTS

| 5,866,587 A | 2/1999 | de Nanteuil et al. |
| 2007/0066646 A1 | 3/2007 | Clauzel et al. |
| 2009/0030002 A1* | 1/2009 | Chen et al. ............ 514/249 |

FOREIGN PATENT DOCUMENTS

| CN | 101209974 A | 7/2008 |
| FR | 2819252 A | 7/2002 |
| WO | 9718194 A1 | 5/1997 |
| WO | 9807742 A1 | 2/1998 |
| WO | 9842659 A2 | 10/1998 |
| WO | WO 9842659 A2 * | 10/1998 |
| WO | 9906410 A1 | 2/1999 |
| WO | 9932451 A1 | 7/1999 |
| WO | 0037436 | 6/2000 |
| WO | 03076422 A1 | 9/2003 |
| WO | 2004060874 | 7/2004 |
| WO | 2006008303 | 1/2006 |
| WO | 2006013193 | 2/2006 |
| WO | 2006013209 A2 | 2/2006 |
| WO | 2007117981 | 10/2007 |

OTHER PUBLICATIONS

Barlaam, et al., "New a-Substituted Succinate-Based Hydroxamic Acids as TNFr Convertase Inhibitors", J. Med. Chem. (1999), 42, pp. 4890-4908.
Brennan, et al., "Two-Dimensional Parallel Array Technology as a New Approach to Automated Combinatorial solid-Phase organic Synthesis", Biotechnology and Bioengineering (Combinatorial Chemistry) (1998), vol. 61, No. 1, pp. 33-45.
Matter, et al., "Affinity and Selectivity of Matrix Metalloproteinase Inhibitors: A Chennometrical Study from the Perspective of Ligands and Proteins", J. Med. Chem. 1999, 42, pp. 4506-4523.
Supuran, et al., "Protease inhibitors. Part 7 Inhibition of *Clostridium histolyticum* collagenase with sulfonylated derivatives of L-valine hydroxamate", European Journal of Pharmaceutical Sciences 10 (2000) pp. 67-76.
Supuran, et al., Protease Inhibitors: Synthesis of Sulfonylated Derivatives as Inhibitors of Clostrzdzum Histol Yticum Collagenase L-Alanine Hydroxamate, J. Enzyme Inhibition, 2000, vol. 15, pp. 111-128.
Scozzafava, et al., "Protease Inhibitors: Synthesis of Potent Bacterial Collagenase and Matrix Metalloproteinase Inhibitors Incorporating N-4-Nitrobenzylsulfonylglycine Hydroxamate Moieties", J. Med. Chem. 2000, 43, pp. 1858-1865.
Li, et al., "Preparation of hydroxamic acid derivatives as antibacterial agents", Database CA [online] Chemical Abstracts Service, retrieved from STN, Database accession No. 149:201241.
Levin et al., Bioorg. Med. Chem. Lett, 13:2799-2803 (2003).
Patani et al., Chem. Rev., 314703176 (1996).
European Journal of Medicinal Chemistry, 35:299-307 (2000).
Bioorganic & Medicinal Chemistry, 8:637-645 (2000).

* cited by examiner

*Primary Examiner* — Wu-Cheng Winston Shen
*Assistant Examiner* — Jean Cornet
(74) *Attorney, Agent, or Firm* — John B. Alexander

(57) ABSTRACT

The present invention provides a compound of formula (I):

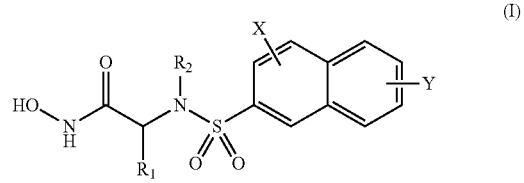

said compound is inhibitor of MMP-12 and/or MMP-13, and thus can be employed for the treatment of a disorder or disease characterized by abnormal activity of MMP-12 and/or MMP-13. Accordingly, the compound of formula (I) can be used in treatment of disorders or diseases mediated by MMP-12 and/or MMP-13. Finally, the present invention also provides pharmaceutical composition that include the compound of formula (I).

2 Claims, No Drawings

SELECTIVE HYDROXAMIC ACID BASED MMP-12 AND MMP-13 INHIBITORS

The invention relates to sulfonylamino hydroxamic acid derivatives and to processes for their preparation, pharmaceutical compositions comprising said compounds, a method of inhibiting matrix-degrading metalloproteinase, such as matrix metalloproteinases 12 and 13 (MMP-12 and MMP-13), in mammals using such compounds and the use of these derivatives as medicaments.

Matrix metalloproteinases (MMPs) are proteinases that are involved in the breakdown and remodeling of the extracellular matrices (ECM) under a variety of physiological and pathological conditions. Matrix metalloproteinases (MMPs), which comprise a family of more than 20 members, use $Zn^{2+}$ in the active sites to catalyze hydrolyses of ECM. Based on their substrate specificities, they can be broadly classified into three subfamilies: collagenase, stromelysins and gelatinases.

Under normal physiological conditions, these enzymes serve many important functions, including wound healing and tissue remodeling. However, when these enzymes are over activated, they can over-degrade ECM, resulting in disease conditions. For example, MMP-2 and MMP-9 (both are gelatinases) are thought to be involved in the pathogenesis of inflammatory, infectious, and neoplastic diseases in many organs. Excess activity of MMP-8, also known as collagenase-2 or neutrophil collagenase, is associated with diseases such as pulmonary emphysema and osteoarthritis. Excess activity of MMP-12, also known as macrophage elastase or metalloelastase, plays a key role in tumor invasion, arthritis, atherosclerosis, Alport syndrome, and chronic obstructive pulmonary disease (COPD). MMP-1 and MMP-13 are involved in the proteolysis of collagen. Excessive degradation of collagen is associated with the development of various diseases, including osteoarthritis.

Osteoarthritis is associated with excessive degradation of type II collagen. Early work suggested that collagenase-1 (MMP-1) may be responsible for such conditions because MMP-1 can specifically cleave type II collagen to produce characteristic ¾ and ¼ fragments. Later work indicated that collagenase-3 (MMP-13) may be more important in the development of osteoarthritis. MMP-13 can also cleave type II collagen to give the characteristic ¾ and ¼ fragments and does so at least 10 times faster than MMP-1. In addition, MMP-13 is found to be expressed in osteoarthritic cartilage. These observations suggest that MMP-13 activity may be a significant contributor to the progression of osteoarthritis and other diseases that are associated with cartilage collagen degradation. See e.g., P. G. Mitchell et al., "*Cloning, expression, and type II collagenolytic activity of matrix metalloproteinase*-13 *from human osteoarthritic cartilage*," J Clin Invest. 1996 Feb. 1; 97(3): 761-768. Therefore, MMP-13 is an attractive target for therapeutic interventions in the management of diseases involving excessive type II collagen degradation.

Many MMP inhibitors are known in the art. For example, U.S. Pat. No. 6,500,983 issued to Kottirsch et al. discloses the use of hydroxamic acid derivatives as MMP inhibitors. U.S. Pat. Nos. 6,277,987 and 6,410,580 issued to Kukkola et al. disclose sulfonyl amino acid and sulfonylamino hydroxamic acid derivatives as MMP inhibitors. The hydroxamic acid moiety in these inhibitors binds to the active site $Zn^{2+}$ to inhibit enzymatic activities. These patents are assigned to the assignee of the present invention and are incorporated by reference in their entireties.

While prior art MMP inhibitors are generally effective in inhibiting the target enzymes, selectivity is more difficult to achieve due to the high degree of homology among the MMPs. Because MMPs serve important functions under normal physiological conditions, therapeutics designed to inhibit any disease-causing MMP preferably are selective. For example, inhibitors for use in the prevention or treatment of osteoarthritis should preferably have substantial selectivity for MMP-13 over other MMPs (e.g., MMP-2 or MMP-9).

The present invention provides inhibitors that are selective for MMPs involved in the development of diseases, such as MMP-13 and MMP-12.

In one aspect, an inhibitor can include a compound of formula (I):

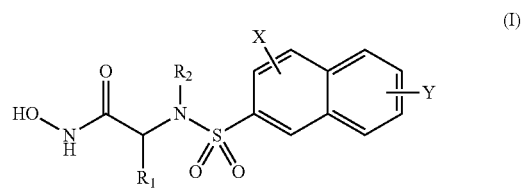

wherein $R_1$ is hydrogen, alkyl, alkenyl, alkynyl, aryl-alkyl-, cycloalkyl, heterocycloalkyl, each of which is optionally substituted by one to three substituents selected from aryl-alkoxy-, hydroxy, alkoxy, HS—, alkyl-S—, alkyl-O—(O)C—, cyano, alkyl-$SO_2$—, or aryl;

$R_2$ is H, alkyl, alkenyl, alkynyl, aryloxy-alkyl-, aryl-alkyl-, heteroaryl-alkyl-, heterocycloalkyl-alkyl, each of which is optionally substituted by one to three substituents selected from HS—, halo, alkoxy, alkyl, or dialkylamino;

X is hydrogen, hydroxyl, alkoxy, or halo;

Y is $R_3$—NH—, wherein $R_3$ is hydrogen, alkyl, alkyl-C(O)—, or aryl; or

Y is alkoxy, alkyl, hydrogen, hydroxyl, alkyl-C(O)—NH—, alkenyl-O—, or aryl-alkoxy-;

$R_1$ and $R_2$ taken together with the carbon atom and the nitrogen atom to which they are attached, form a 3- to 7-membered ring;

or a pharmaceutically acceptable salts thereof; or an optical isomer thereof; or a mixture of optical isomers.

Preferably, the present invention provides the compound of formula (I), wherein $R_1$ is ($C_1$-$C_7$) alkyl, ($C_1$-$C_7$) alkenyl, ($C_1$-$C_7$) alkynyl, or (4- to 7-membered) heterocycloalkyl, each of which is optionally substituted by one to three substituents selected from hydroxy, HS—, ($C_1$-$C_7$) alkyl-S—, ($C_6$-$C_{10}$) aryl, or ($C_1$-$C_7$) alkyl-O—C(O)—; $R_2$ is ($C_1$-$C_7$) alkyl, ($C_1$-$C_7$) alkenyl, ($C_6$-$C_{10}$) aryl-($C_1$-$C_7$) alkyl-, (5- to 9-membered) heteroaryl-($C_1$-$C_7$) alkyl-, or ($C_6$-$C_{10}$) aryloxy-($C_1$-$C_7$) alkyl-; X is hydrogen, hydroxy, or ($C_1$-$C_7$) alkoxy; Y is hydrogen, ($C_1$-$C_7$) alkyl, ($C_1$-$C_7$) alkenyl-O—, $H_2$N—, or ($C_1$-$C_7$) alkyl-C(O)—NH—; or $R_1$ and $R_2$ taken together with the carbon atom and the nitrogen atom to which they are attached, form a 3- to 7-membered ring; or a pharmaceutically acceptable salts thereof; or an optical isomer thereof; or a mixture of optical isomers.

More preferably, the present invention provides the compound of formula (I), wherein $R_1$ is a ($C_1$-$C_7$) alkyl, or ($C_1$-$C_7$) alkenyl; $R_2$ is a ($C_1$-$C_7$) alkyl, ($C_1$-$C_7$) alkenyl, ($C_1$-$C_7$) alkynyl, or ($C_6$-$C_{10}$) aryl-($C_1$-$C_7$) alkyl-; Y is H, $H_2$N—, ($C_1$-$C_4$) alkoxy, ($C_1$-$C_4$) alkyl, or ($C_1$-$C_4$) alkyl-NH—; X is H, HO—, or ($C_1$-$C_4$) alkoxy; or a pharmaceutically acceptable salts thereof; or an optical isomer thereof; or a mixture of optical isomers.

In another aspect, an inhibitor can include a compound of formula (II).

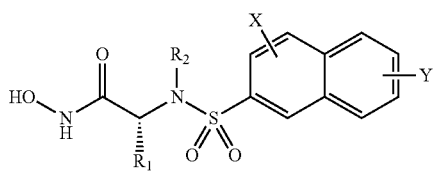

(II)

wherein

R₁ is hydrogen, alkyl, alkenyl, alkynyl, aryl-alkyl-, cycloalkyl, heterocycloalkyl, each of which is optionally substituted by one to three substituents selected from aryl-alkoxy-, hydroxy, alkoxy, HS—, alkyl-S—, alkyl-O—(O)C—, cyano, alkyl-SO₂—, or aryl;

R₂ is H, alkyl, alkenyl, alkynyl, aryloxy-alkyl-, aryl-alkyl-, heteroaryl-alkyl-, heterocycloalkyl-alkyl, each of which is optionally substituted by one to three substituents selected from HS—, halo, alkoxy, alkyl, or dialkylamino;

X is hydrogen, hydroxyl, alkoxy, or halo;

Y is R₃—NH—, wherein R₃ is hydrogen, alkyl, alkyl-C(O)—, or aryl; or

Y is alkoxy, alkyl, hydrogen, hydroxyl, alkyl-C(O)—NH—, alkenyl-O—, or aryl-alkoxy-;

R₁ and R₂ taken together with the carbon atom and the nitrogen atom to which they are attached, form a 3- to 7-membered ring;

or a pharmaceutically acceptable salts thereof; or an optical isomer thereof; or a mixture of optical isomers.

Preferably, the present invention provides the compound of formula (I), wherein R₁ is (C₁-C₇) alkyl, (C₁-C₇) alkenyl, (C₁-C₇) alkynyl, or (4- to 7-membered) heterocycloalkyl, each of which is optionally substituted by one to three substituents selected from hydroxy, HS—, (C₁-C₇) alkyl-S—, (C₆-C₁₀) aryl, or (C₁-C₇) alkyl-O—C(O)—; R₂ is (C₁-C₇) alkyl, (C₁-C₇) alkenyl, (C₆-C₁₀) aryl-(C₁-C₇) alkyl-, (5- to 9-membered) heteroaryl-(C₁-C₇) alkyl-, or (C₆-C₁₀) aryloxy-(C₁-C₇) alkyl-; X is hydrogen, hydroxy, or (C₁-C₇) alkoxy; Y is hydrogen, (C₁-C₇) alkyl, (C₁-C₇) alkenyl-O—, H₂N—, or (C₁-C₇) alkyl-C(O)—NH—; or R₁ and R₂ taken together with the carbon atom and the nitrogen atom to which they are attached, form a 3- to 7-membered ring; or a pharmaceutically acceptable salts thereof; or an optical isomer thereof; or a mixture of optical isomers.

More preferably, the present invention provides the compound of formula (I), wherein R₁ is a (C₁-C₇) alkyl, or (C₁-C₇) alkenyl; R₂ is a (C₁-C₇) alkyl, (C₁-C₇) alkenyl, (C₁-C₇) alkynyl, or (C₆-C₁₀) aryl-(C₁-C₇) alkyl-; Y is H, H₂N—, (C₁-C₄) alkoxy, (C₁-C₄) alkyl, or (C₁-C₄) alkyl-NH—; X is H, HO—, or (C₁-C₄) alkoxy; or a pharmaceutically acceptable salts thereof; or an optical isomer thereof; or a mixture of optical isomers.

In another aspect, an inhibitor can include a compound of formula (IIA)

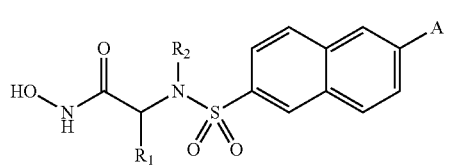

(IIA)

wherein

R₁ is alkyl, R₂ is alkyl or aryl-alkyl-, A is aryl-NH—, H₂N—, Alkyl, hydroxyl, alkoxy, alkyl-C(O)—NH—, alkenyl-O—, or aryl-alkyl-O—, or a pharmaceutically acceptable salts thereof; or an optical isomer thereof; or a mixture of optical isomers.

Preferably the present invention provides the compound of formula (IIA), wherein R₁ is (C₁-C₄) alkyl, R₂ is (C₁-C₇) alkyl, (C₆-C₁₀) aryl-(C₁-C₇) alkyl-, A is (C₁-C₇) alkyl, (C₁-C₇) alkenyl-O—, H₂N—, or (C₁-C₇) alkyl-C(O)—NH—, or (C₆-C₁₀) aryl-(C₁-C₇) alkyl-O—; or a pharmaceutically acceptable salts thereof; or an optical isomer thereof; or a mixture of optical isomers.

In another aspect, an inhibitor can include a compound of formula (III).

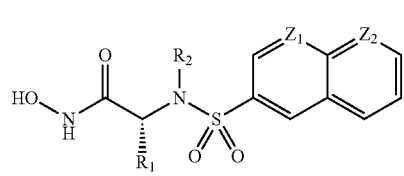

(III)

wherein

Z₁ and Z₂ are independently C or N;

R₁ and R₂ are independently hydrogen, alkyl, alkenyl, or alkynyl;

R₁ and R₂ taken together with the carbon atom and the nitrogen atom to which they are attached, form a 3- to 7-membered ring; or or a pharmaceutically acceptable salts thereof; or an optical isomer thereof; or a mixture of optical isomers.

Preferably, the present invention provides the compound of formula (III), wherein Z₁ is N, Z₂ is C, R₁ and R₂ are independently (C₁-C₇) alkyl, (C₁-C₇) alkenyl, or (C₁-C₇) alkynyl; or R₁ and R₂ taken together with the carbon atom and the nitrogen atom to which they are attached, form a 3- to 7-membered ring; or a pharmaceutically acceptable salts thereof; or an optical isomer thereof; or a mixture of optical isomers.

Also preferably, the present invention provides the compound of formula (III), wherein Z₁ is C, Z₂ is N, R₁ and R₂ are independently (C₁-C₇) alkyl, (C₁-C₇) alkenyl, or (C₁-C₇) alkynyl; or R₁ and R₂ taken together with the carbon atom and the nitrogen atom to which they are attached, form a 3- to 7-membered ring; or a pharmaceutically acceptable salts thereof; or an optical isomer thereof; or a mixture of optical isomers.

The present invention provides for compounds of formula I, pharmaceutical compositions employing such compounds and for methods of using such compounds.

For purposes of interpreting this specification, the following definitions will apply and whenever appropriate, terms used in the singular will also include the plural and vice versa.

As used herein, the term "alkyl" refers to a branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. When an alkyl group includes one or more unsaturated bonds, it may be referred to as an alkenyl (double bond) or an alkynyl (triple bond) group. Furthermore, when an alkyl group is linked to an aryl group (defined below), it may be referred to as an "arylalkyl" group.

The term "aryl" refers to monocyclic or bicyclic aromatic hydrocarbon groups having 6-20 carbon atoms in the ring portion. Preferably, the aryl is a ($C_6$-$C_{10}$) aryl. Non-limiting examples include phenyl, biphenyl, naphthyl or tetrahydronaphthyl, each of which may optionally be substituted by 1-4 substituents, such as optionally substituted alkyl, trifluoromethyl, cycloalkyl, halo, hydroxy, alkoxy, acyl, alkyl-C(O)—O—, aryl-O—, heteroaryl-O—, optionally substituted amino, thiol, alkylthio, arylthio, nitro, cyano, carboxy, alkyl-O—C(O)—, carbamoyl, alkylthiono, sulfonyl, sulfonamido, heterocycloalkyl and the like.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "carbamoyl" refers to $H_2NC$(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonamido" refers to alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S(O)$_2$—N(alkyl)-, heteroaryl-S(O)$_2$—N(alkyl)-, heteroaryl-alkyl-S(O)$_2$—N(alkyl)- and the like.

As used herein, the term "heterocycloalkyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroindolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocycloalkyl" further refers to heterocyclic groups as defined herein substituted with 1, 2 or 3 substituents selected from the groups consisting of the following:
(a) alkyl;
(b) hydroxy (or protected hydroxy);
(c) halo;
(d) oxo, i.e., =O;
(e) amino ($NH_2$), alkylamino or dialkylamino;
(f) alkoxy;
(g) cycloalkyl;
(h) carboxy;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "sulfonyl" refers to R—$SO_2$—, wherein R is hydrogen, alkyl, aryl, heteroaryl, aryl-alkyl, heteroaryl-alkyl, aryl-O—, heteroaryl-O—, alkoxy, aryloxy, cycloalkyl, or heterocycloalkyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. As used herein, the term "lower alkoxy" refers to the alkoxy groups having 1-7 carbons and preferably 1-4 carbons.

As used herein, the term "acyl" refers to a group R—C(O)—, wherein R has from 1 to 10 carbon atoms of a straight, branched, or cyclic configuration or a combination thereof, attached to the parent structure through carbonyl functionality. Such group may be saturated or unsaturated, and aliphatic or aromatic. Preferably, R in the acyl residue is alkyl, or alkoxy, or aryl, or heteroaryl. Also preferably, one or more carbons in the acyl residue may be replaced by nitrogen, oxygen or sulfur as long as the point of attachment to the parent remains at the carbonyl. Examples include but are not limited to: acetyl, benzoyl, propionyl, isobutyryl, t-butoxycarbonyl, benzyloxycarbonyl and the like. Lower acyl refers to acyl containing one to four carbons.

As used herein, the term "cycloalkyl" refers to optionally substituted saturated or unsaturated monocyclic, bicyclic or tricyclic hydrocarbon groups of 3-12 carbon atoms, preferably 3-7 carbon atoms, each of which may be substituted by one or more substituents, such as alkyl, halo, oxo, hydroxy, alkoxy, alkyl-C(O)—, acylamino, carbamoyl, alkyl-NH—, (alkyl)$_2$N—, thiol, alkylthio, nitro, cyano, carboxy, alkyl-O—

C(O)—, sulfonyl, sulfonamido, sulfamoyl, heterocycloalkyl and the like. Exemplary monocyclic hydrocarbon groups include but are not limited to: cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo [2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "sulfamoyl" refers to $H_2NS(O)_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

As used herein, the term "aryloxy" refers to both an —O-aryl and an —O— heteroaryl group, wherein aryl and heteroaryl are defined herein.

As used herein, the term "acylamino" refers to the group —NRC(O)R' where each of R and R' is independently hydrogen, alkyl, aryl, heteroaryl, or heterocycloalkyl, where both R and R' groups are optionally joined to form a heterocyclic group (e.g., morpholino) wherein alkyl, aryl, heteroaryl and heterocycloalkyl are as defined herein.

As used herein, the term "heteroaryl" refers to a 5-14 membered monocyclic- or bicyclic- or fused polycyclic-ring system, having 1 to 8 heteroatoms selected from N, O or S. Preferably, the heteroaryl is a 5-10 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocycloalkyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "acylamino" refers to the group —NRC(O)R' where each of R and R' is independently hydrogen, alkyl, aryl, heteroaryl, or heterocycloalkyl, where both R and R' groups are optionally joined to form a heterocyclic group (e.g., morpholino) wherein alkyl, aryl, heteroaryl and heterocycloalkyl are as defined herein.

As used herein, the term "halo" refers to fluoro, chloro, bromo, and iodo.

As used herein, the term "isomers" refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S). The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto (e.g., phenol or hdroxyamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences,* 20th ed., Mack Publishing Company, Easton, Pa., (1985), which is herein incorporated by reference.

The present invention includes all pharmaceutically acceptable isotopically-labeled compounds of the invention, i.e. Agents of the Invention, wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labeled Agents of the Invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled Agents of the Invention can generally be prepared by conventional techniques known to those skilled in the art or by processes analogous to those described in the accompanying Examples and Preparations using an appropriate isotopically-labeled reagents in place of the non-labeled reagent previously employed.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces expression or activity of MMP-13 or another selected MMP.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary,* (W.B. Saunders Co. 27th ed. 1988).

As used herein, the term "inhibition" or "inhibiting" refers to the reduction or suppression of a given condition, symptom, or disease, or a significant decrease in the baseline activity of a biological activity or process. Preferably, the condition is associated with or mediated by MMP-13, such as osteoarthritis.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans (E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the hydroxamide or sulfonamide moiety may thus be employed to resolve the compounds of the present invention into their optical antipodes, e.g., by fractional crystallization of a metal (e.g., $Zn^{2+}$) complex formed with an optically active co-ligand, e.g., L- or D-histidine. Racemic products can also be resolved by chiral chromatography, e.g., high pressure liquid chromatography (HPLC) using a chiral adsorbent.

Finally, compounds of the present invention are either obtained in the free form, as a salt thereof, or as prodrug derivatives thereof.

When a basic group is present in the compounds of the present invention (such as in a substituent group), the compounds can be converted into acid addition salts thereof, preferably pharmaceutically acceptable salts thereof. These may be formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as ($C_1$-$C_4$) alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as ($C_1$-$C_4$) alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, such as calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids such as arginine, lysine and the like. Salts may be formed using conventional methods, advantageously in the presence of an ethereal or alcoholic solvent, such as a lower alkanol. From the solutions of the latter, the salts may be precipitated with diethyl ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

The present invention also provides pro-drugs of the compounds of the present invention that converts in vivo to the compounds of the present invention. A pro-drug is an active or inactive compound that is modified through in vivo reaction, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-delakylation, oxidative O- and S-delakylation, oxidative deamination, as well as other oxidative reactions.

2. Reductive reactions, such as reduction of carbonyl groups, reduction of alcoholic groups and carbon-carbon double bonds, reduction of nitrogen-containing functions groups, and other reduction reactions.

3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., US20040077595, application Ser. No. 10/656, 838, incorporated herein by reference. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, *The Practice of Medicinal Chemistry*, Ch. 31-32, Ed. Werriuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the pro-drugs, any reference to the compounds of the present invention is to be understood as referring also to the corresponding pro-drugs of the compounds of the present invention, as appropriate and expedient.

Furthermore, the compounds of the present invention, including their salts, can also be obtained in the form of their hydrates, or include other solvents used for their crystallization.

The compounds of the present invention have valuable pharmacological properties, they are useful as inhibitors of matrix metalloproteinases such as matrix metalloproteinase 13 (MMP-13) or MMP-12. MMP12, also known as macrophage elastase or metalloelastase, is able to degrade extracellular matrix components such as elastin and is involved in tissue remodeling processes. MMP-12 has been indicated to be a key protein in the pathologenesis of tumor invasineness, arthritis, atherosclerosis, Alport syndrome, and chronic obstructive pulmonary disease (COPD). MMP-13, also known as collagenase 3, has been indicated in (1) extracellular matrix degradation and cell-matrix interaction associated with metastasis especially as observed in invasive breast cancer lesions and in malignant epithelia growth in skin carcinogenesis; and (2) during primary ossification and skeletal remodelling (M. Stahle-Backdahl et al., (1997) *Lab. Invest.* 76 (5):717-728; N. Johansson et al., (1997) *Dev. Dyn.* 208(3): 387-397), in destructive joint diseases such as rheumatoid and osteo-arthritis (D. Wernicke et al., (1996) *J. Rheumatol.* 23:590-595; P. G. Mitchell et al., (1996) *J. Clin. Invest.* 97(3): 761-768; O. Lindy et al., (1997) *Arthritis Rheum* 40(8:1391-1399); and the aseptic loosening of hip replacements (S. Imai et al., (1998) *J. Bone Joint Surg. Br.* 80(4):701-710). MMP13 has also been implicated in chronic adult periodontitis as it has been localised to the epithelium of chronically inflamed mucosa human gingival tissue (V. J. Uitto et al., (1998) *Am. J. Pathol* 152(6):1489-1499) and in remodelling of the collagenous matrix in chronic wounds (M. Vaalamo et al., (1997) *J. Invest. Dermatol.* 109(1): 96-101).

In certain embodiments, some of the compounds of the present invention are selective MMP-13 inhibitors over MMP-2. The selective MMP-13 inhibitors refer to the compounds for which the ratio of the inhibitory activity for MMP-13 over that for MMP-2 is at least two, or five, or ten, or twenty, or fifty or more. The selective MMP-13 inhibitors as used herein, also encompass the compounds in free form or in pharmaceutically acceptable salts, carriers as well the pro-drugs, or metabolites of the compounds.

Accordingly, the compounds of the present invention are also useful for treatment of a disorder or a disease mediated by MMP-13 or MMP-12. In particular, the compounds of the present invention are useful for treatment of at least one disorder or disease selected from Alport syndrome, asthma, rhinitis, chronic obstructive pulmonary diseases (COPD), arthritis (such as rheumatoid arthritis and osteoarthritis), cancer invasion and metastasis, diseases involving tissue destruction, loosening of hip joint replacements, periodontal disease.

Additionally, the present invention provides:

a compound of the present invention for use as a medicament;

the use of a compound of the present invention for the preparation of a pharmaceutical composition for the delay of progression and/or treatment of a disorder or disease mediated by MMP-12, and/or MMP-13.

the use of a compound of the present invention for the preparation of a pharmaceutical composition for the delay of progression and/or treatment of a disorder or disease mediated by MMP-12, and/or MMP-13.

the use of a compound of the present invention for the preparation of a pharmaceutical composition for the delay of progression and/or treatment of a disorder or disease selected from Alport syndrome, asthma, rhinitis, chronic obstructive pulmonary diseases (COPD), arthritis (such as rheumatoid arthritis and osteoarthritis), cancer invasion and metastasis, diseases involving tissue destruction, loosening of hip joint replacements, periodontal disease.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Preferably, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical compositions contain a therapeutically effective amount of a compound of the invention as defined above, either alone or in a combination with another therapeutic agent. Such other therapeutic agents include, for example, an anti-inflammatory agent with cyclooxygenase inhibiting activity, or other antirheumatic agents such as methotrexate, each at an effective therapeutic dose as reported in the art. Examples of antiinflammatory agents with cyclooxygenase inhibiting activity are diclofenac, naproxen, ibuprofen, and the like.

Furthermore, the combinations as described above can be administered to a subject via simultaneous, separate or sequential administration (use). Simultaneous administration (use) can take place in the form of one fixed combination with two or more active ingredients, or by simultaneously administering two or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two compounds are administered such that no overlap of measurable blood levels of both compounds are present in an overlapping manner (at the same time).

Also combinations of two or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

Additionally, the present invention provides:
a pharmaceutical composition or combination of the present invention for use as a medicament;
the use of a pharmaceutical composition or combination of the present invention for the delay of progression and/or treatment of a disorder or disease mediated by MMP-12 and/or MMP-13.
the use of a pharmaceutical composition or combination of the present invention for the delay of progression and/or treatment of a disorder or disease selected from increased degradation of collagen, osteoarthritis, malignant epithelia growth in skin carcinogenesis, tumor invasineness, arthritis, atherosclerosis, Alport syndrome, and chronic obstructive pulmonary disease (COPD).

The pharmaceutical composition or combination of the present invention can be in unit dosage of about 1-1000 mg of active ingredients for a subject of about 50-70 kg, preferably about 5-500 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range, depending on the route of administration, between about 0.1-500 mg/kg, preferably between about 1-100 mg/kg.

The compounds are particularly useful for the treatment of, for example, inflammatory conditions, osteoarthritis, rheumatoid arthritis and tumors. Beneficial effects are evaluated in pharmacological tests generally known in the art, and as illustrated herein.

Antiinflammatory activity can be determined in standard inflammation and arthritic animal models well-known in the art, e.g. the adjuvant arthritis model in rats and the collagen II induced arthritis model in mice (Mediators of Inflam. 1, 273-279 (1992).

Gelatinase (MMP-2) inhibitory activities can be determined as follows: Stock solutions of substrate (MCA-Lys-Pro-Leu-Gly-Leu-Dpa-Ala-Arg-NH$_2$) are prepared in DMSO at a concentration of 1.4 mM. Stock solutions of inhibitors (0.03 mM-3 mM) are also prepared in DMSO. The inhibitors are diluted into the assay solutions, and the controls use an equal volume of DMSO so that the final DMSO concentration from the inhibitor and substrate dilutions in all assays is 1.0%. Assays are performed in an assay buffer (100 mM sodium chloride, 10 μM ZnCl.Sub 2, 10 mM CaCl.sub.2, 100 mM Tris-Cl pH7.5, 0.05% Brij-35), containing 1.0% DMSO from the substrate and inhibitor additions. The substrate concentration used in the assays is 5 μM. The assays are carried out at 20-25° C. The fluorescence changes, as a result of substrate cleavage, are monitored using an excitation wavelength of 325 nm and an emission wavelength of 405 nm. The reaction mixtures are added in duplicate into appropriate wells of a 384-well assay plate. The reaction mixtures are preincubated with the inhibitors for 60 minutes The reactions are started by the addition of MMP substrate, and the fluorescence intensity changes are measured after 60 minutes The apparent enzyme activity in the presence of an inhibitor is then compared with that in the absence of any inhibitor to determine the inhibition effect of the inhibitor. These techniques are within the knowledge of one skilled in the art. The inhibition results are expressed as the inhibitor concentrations required to effect 50% inhibition ($IC_{50}$) of the enzyme activity, as compared with the control (non-inhibited) reactions.

Illustrative of the invention, compound 80 in the Tables below exhibits an $IC_{50}$ of 55 nM.

Collagenase-3 (MMP-13) inhibitory activity is determined as described above. Recombinant pro-collagenase-3 is activated with 1 mM APMA, and stored in the assay buffer after extensive dialysis in the assay buffer.

Illustrative of the invention, compound 80 in the Tables below exhibits an $IC_{50}$ of about 113 nM.

MMP-12 inhibitory activity is determined as described above.

The effect of compounds of the invention in vivo can be determined in rats. Typically, six rats are dosed orally with a compound up to four hours before being injected intra-articularly in both knees (N=12) with 0.1 to 2 ug/knee of recombinant human MMP-13 dissolved 0.05 mL of saline. Two hours later the rats are sacrificed, synovial lavage is collected, and chondroitin sulfate (CS) fragments released into the joint are quantitated. Chondroitin sulfate is measured by an inhibition ELISA using a Chondrotin Sulfate specific antibody (CS-56 (Sigma), in an analogous manner to the methods described by Thonar (Thonar, E. J.-M. A., Lenz, M. E., Klinsworth, G. K., Caterson, B., Pachman, L. M., Glickman, P., Katz, R., Huff, J., Keuttner, K. E. Quantitation of keratan sulfate in blood as a marker of cartilage catabolism, Arthr. Rheum. 28, 1367-1376 (1985).

The effect in protecting against cartilage degradation in arthritic disorders can be determined e.g. in a surgical model of osteoarthritis described in Arthritis and Rheumatism, Vol. 26, 875-886 (1983).

The effect of the compounds of the invention for the treatment of emphysema can be determined in animal models described in American Review of Respiratory Disease 117, 1109 (1978).

The antitumor effect of the compounds of the invention can be determined, for example, by measuring the growth of human tumors implanted subcutaneously in Balb/c nude mice according to methodology well-known in the art in comparison to placebo treated mice. Illustrative tumors are, for example, estrogen-dependent human breast carcinoma BT20 and MCF7, human bladder carcinoma T24, human colon carcinoma Colo 205, human lung adenocarcinoma A549, and human ovarian carcinoma NIH-OVCAR3.

The inhibition of tumor metastasis can be determined in two lung metastasis models. In the B16-F10 melanoma model, metastasis is measured by counting the numbers of lung metastasized melanoma nodules produced by intravenously injected B16-F10 melanoma cells into BDF1 treated mice, according to methodology well known in the art. In the HT1080 model, metastasis is quantified by measuring the fluorescence intensity of enhanced green fluorescent protein (EGFP) in the lung of Balb/c nude mice produced by the metastasized tumor from intravenously injected GFP-expressing human fibrosarcoma HT1080 cells. The inhibition is obtained by comparison of compound-treated and placebo-treated mice in both methods. In the HT1080 model, EGFP-expressing HT1080 cells are prepared by limiting dilution method in the presence of geneticin after transfecting the EGFP expression vector (pEGFP-CI) (CLONTECH Laboratories Inc., Palo Alto, Calif.). A suspension of cells ($10^6$ cells/0.1 mL of PBS) is injected intravenously into Balb/c nude mice. After administering test compounds and vehicle p.o. 3 weeks, tumor metastasized lungs of mice are removed after sacrifice and homogenized. After centrifugation, the cells are washed 3 times with lysing reagent (150 mM ammonium chloride, 0.1 mM EDTA-4 Na, 10 mM $KHCO_3$, pH 7.4) to lyse the red blood cells and 2 times with PBS. After centrifugation, EGFP is extracted from cells by 10% Triton in PBS and put into the wells of a 96-well multi plate. The fluorescence intensity is determined using a fluorescence plate reader at the excitation and emission wave lengths of 485 and 530 nm, respectively.

The effect of the compounds of the invention on atherosclerotic conditions can be evaluated using atherosclerotic plaques from cholesterol-fed rabbits which contain activated matrix metalloproteinases as described by Sukhova et al, Circulation 90, 1404 (1994). The inhibitory effect on matrix metalloproteinase enzyme activity in rabbit atherosclerotic plaques can be determined by in situ zymography, as described by Galis et al, J. Clin. Invest. 94, 2493 (1994), and is indicative of plaque rupture.

The compounds of the invention are particularly useful in mammals as antiinflammatory agents for the treatment of, for example, osteoarthritis and rheumatoid arthritis, as antitumor agents for the treatment and prevention of tumors growth, tumor metastasis, tumor invasion or progression, and as antiatherosclerotic agents for the treatment and prevention of the rupture of atherosclerotic plaques.

The present invention also relates to methods of using the compounds of the invention and their pharmaceutically acceptable salts, or pharmaceutical compositions thereof, in mammals for inhibiting the matrix-degrading metalloproteinases, e.g. stromelysin, gelatinase, collagenase and macrophage metalloelastase, for inhibiting tissue matrix degradation, and for the treatment of matrix-degrading metalloproteinase dependent conditions as described herein, e.g. inflammation, rheumatoid arthritis, osteoarthritis, also tumors (tumor growth, metastasis, progression or invasion), pulmonary disorders, and the like described herein. Tumors (carcinomas) include mammalian breast, lung, bladder, colon, prostate and ovarian cancer, and skin cancer, including melanoma and Kaposi's sarcoma.

The following Examples are intended to illustrate the invention and are not to be construed as being limitations thereon. Temperatures are given in degrees Centigrade. If not mentioned otherwise, all evaporations are performed under reduced pressure, preferably between about 15 and 100 mmHg (20-133 mbar). The structures of final products, intermediates and starting materials are confirmed by standard analytical methods, e.g. microanalysis and/or spectroscopic characteristics (e.g. MS, IR, or NMR). Abbreviations used are those conventional in the art.

EXAMPLES

The compounds of formula (I) can be prepared by the procedures described in the following sections. In a typical procedure a carboxylic acid derivative is prepared according to Method A, Method B, Method C, Method D, Method E, Method F, or Method G. Generally, the compounds of formula (I) can be prepared from a carboxlic acid derivative according to Method J, Method K, or Method L.

Method a: General Method for the Conversion of Amino Acid Tert-Butyl Esters to N-Sulfonyl Amino Acid Derivatives

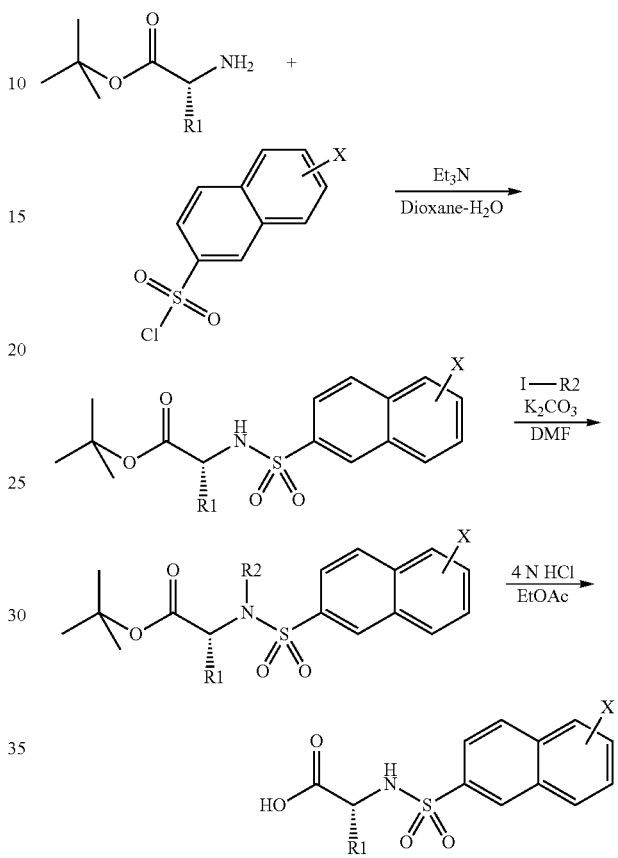

As to the individual steps in the above scheme, step 1 involves the sulfonylation of D-valine tert-butyl ester with a suitably substituted naphthalene-2-sulfonyl chloride to yield a substituted N-(naphthalene-2-sulfonyl)-D-valine tert-butyl ester. Step 2 involves the N-alkylation of the sulfonylamide, using an appropriate alkyl halide (e.g., 1-iodo-3-methylbutane or isoamyl iodide) between 20° C. and 90° C. Step 3 involves the deprotection of the tert-butyl ester. These derivatives may be converted into the requisite N-hydroxyamides via any of the general methods described below.

Typical Procedure for N-Sulfonylation

N-(6-acetoxy naphthalene-2-sulfonyl)-D-valine tert-butyl ester

D-valine tert-butyl ester (6.24 g, 35.9 mmol), 6-acetoxy naphthalene-2-sulfonyl chloride (10.2 g, 35.9 mmol) and triethylamine (12.5 mL, 89.7 mmol) are stirred in dioxane-water (1:1, 243 mL) at ambient temperature for 2 hours. The reaction mixture is acidified with a solution of aqueous citric acid (10% w/w, 800 mL). The precipitate is collected by filtration affording product as pale yellow crystals (10.2 g, 68% yield). LCMS (m/z): (439.28; M+18, 420.24; M−1).

Typical Procedure for N-Alkylation of Sulfonamides

N-isoamyl-N-(6-acetoxy naphthalene-2-sulfonyl)-D-valine tert-butyl ester

To a solution of N-(6-acetoxy naphthalene-2-sulfonyl)-D-valine tert-butyl ester (3.15 g, 7.48 mmol) in N,N-dimethylformamide (15 mL) is added potassium carbonate (3.09 g, 22.36 mmol), followed by 1-bromo-3-methyl butane (1.79 mL, 14.94 mmol), and the reaction is allowed to stir at ambient temperature for 16 h. Another equivalent of 1-bromo-3-methyl butane (0.9 mL, 7.5 mmol) is added and the reaction is allowed to stir for 16 h at ambient temperature. The reaction is poured over water and extracted three times with dichloromethane. The combined organic extracts are washed with brine, dried over magnesium sulfate and concentrated in vacuo. The crude product is purified by column chromatography and eluted with a gradient of 2-7% (hexanes-ethyl acetate) to afford the title compound as a yellow oil (2.5 g, 68% yield), along with N-isoamyl-N-(6-(3-methylbutoxy) naphthalene-2-sulfonyl)-D-valine tert-butyl ester as a yellow oil (0.3 g, 7.7% yield). LCMS (m/z): (492.26; M+1).

Typical Procedure for the Conversion of Tert-Butyl Esters to Carboxylic Acids

N-Isoamyl-N-(6-hydroxy naphthalene-2-sulfonyl)-D-valine

N-Isoamyl-N-(6-hydroxy naphthalene-2-sulfonyl)-D-valine tert-butyl ester (0.33 g, 0.74 mmol) is dissolved in 4 N hydrochloric acid in ethyl acetate (50 mL), and the reaction is allowed to stir at ambient temperature for 16 h. The solvent is removed in vacuo, and the residue is purified by column chromatography (15% hexanes-ethyl acetate) to afford the title compound as a colorless oil (0.26 g, 90% yield). LCMS (m/z): (394.24, M+1; 392.27, M−1).

While the above procedure illustrates the synthesis of a 6-hydroxynaphthane derivative, one of ordinary skill in the art would appreciate that other substituted naphthane derivates (having substituents at different positions or having different substitutents) may be similarly prepared.

Method B: General Method for the Conversion of Amino Acid Tert-Butyl Carbamates to N-Sulfonyl Amino Acid Derivatives

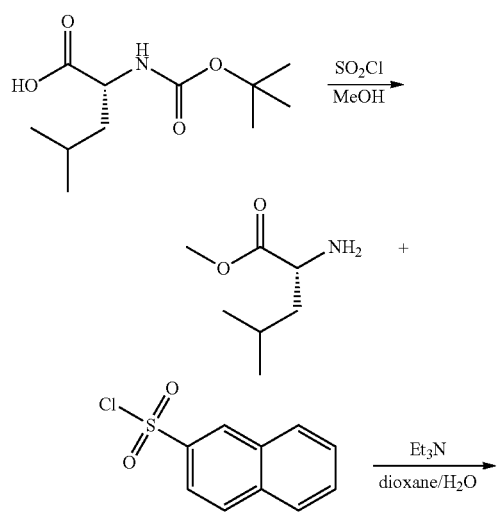

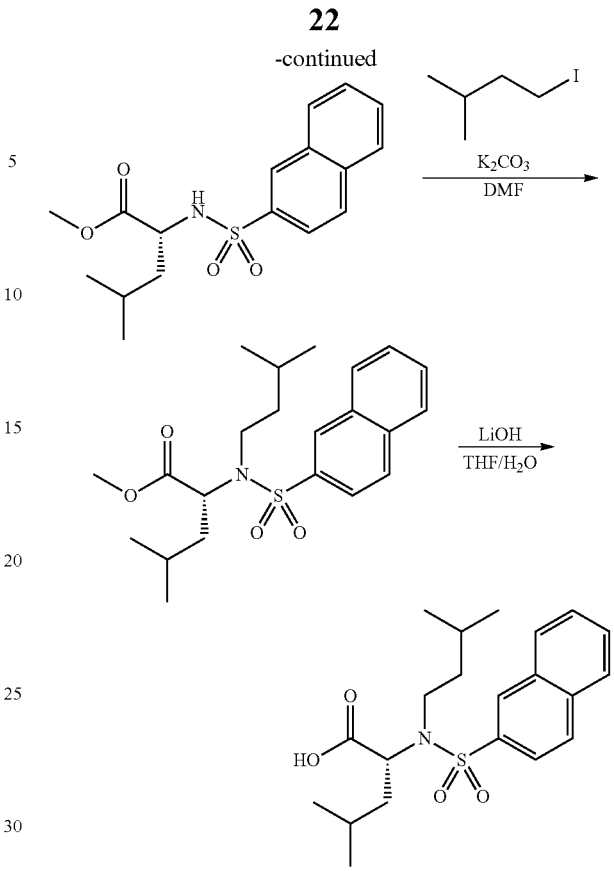

As to the individual steps in method B, step 1 involves the formation of D-isoleucine methyl ester with a concomitant removal of the tert-butoxy carbamate. Alternatively, amino acids without the tert-butoxy carbamate group can be converted directly to the corresponding methyl ester under identical conditions. When the desired methyl ester is commercially available, step 1 may be omitted while the remainder of method B is followed. Step 2 involves the sulfonylation of D-leucine methyl ester with a suitably substituted naphthalene-2-sulfonyl chloride to yield a substituted N-(naphthalene-2-sulfonyl)-D-leucine methyl ester. Step 3 involves the N-alkylation of the sulfonylamide, using an appropriate alkyl halide (e.g., 1-iodo-3-methylbutane or isoamyl iodide). Step 4 involves the deprotection of the methyl ester via saponification

Typical Procedure for the Formation of Methyl Esters

(R)-2-Amino-4-methyl-pentanoic acidmethyl ester

To a solution of (R)-2-tert-butoxycarbonylamino-4-methyl-pentanoic acid (2 g, 8.7 mmol) in methanol (20 mL) is added thionyl chloride (2.59 g, 21.7 mmol). The reaction mixture is refluxed for 2 h. The reaction mixture is cooled to room temperature and concentrated in vacuo. The crude product is carried on without any further purification. $^1$H NMR (400 MHz, MeOD): δ 1.00 (q, 6H, J=3 Hz), 1.7-1.9 (m, 3H, J=7.7 Hz), 3.85 (s, 3H), 4.0 (t, 1H).

Typical Procedure for the Sulfonylation of Amines

(R)-4-Methyl-2-(naphthalene-2-sulfonylamino)-pentanoic acid methyl ester

To a suspension of methyl ester (8.7 mmol, 1 eq) in dioxane/water (25 mL/25 mL, 1:1) is added triethylamine (3.1 g, 30.45 mmol) followed by the addition of 2-naphthalenesulfonyl chloride (1.97 g, 8.7 mmol). The reaction is stirred at room temperature for 18 h, then acidified with 1 N hydrochloric acid and extracted with dichloromethane. The combined organic extracts are dried over sodium sulfate and concentrated to give the crude product, which is carried on without any further purification. LCMS (m/z): 336 (M+1).

Typical Procedure for Alkylation of Sulfonamides (R)-4-Methyl-2-[(3-methyl-butyl)-(naphthalene-2-sulfonyl)-amino]-pentanoic acid methyl ester To a mixture of the sulfonylated methyl ester (8.7 mmol, 1.0 equivalents) and potassium carbonate in N,N-dimethylformamide (20 mL) is added 1-iodo-3-methyl butane. The mixture is stirred at room temperature for 18 h. The reaction is diluted with water and extracted with ethyl acetate. The combined organic extracts are washed with brine, dried over sodium sulfate and concentrated to afford the crude product (3.2 g) which is carried on without additional purification. LCMS (m/z): 406 (M+1).

General Procedure for the Saponification of Methyl Esters (R)-4-Methyl-2-[(3-methyl-butyl)-(naphthalene-2-sulfonyl)-amino]-pentanoic acid To a solution of methyl ester (1.6 g, 3.95 mmol) in tetrahydrofuran/water (21 mL/7 mL) is added lithium hydroxide (1 N, 7.9 mL). The reaction is stirred at room temperature for 18 h. The reaction mixture is acidified 1 N hydrochloric acid and extracted with ethyl acetate. The combined organic extracts are dried over sodium sulfate and concentrated in vacuo. Purification by flash chromatography yields 810 mg of the title compound as a white foam. $^1$H NMR (400 MHz, MeOD): δ 0.95 (m, 12H), 1.3-1.8 (m, 6H), 3.15-3.4 (m, 2H), 4.55 (q, 1H, J=5 Hz), 7.55-7.65 (m, 2H), 7.8 (dd, 1H), 7.91-8.05 (m, 3H), 8.40 (s, 1H). LCMS (m/z): 392 (M+1). Analytics calculated for $C_{21}H_{29}NO_4S$: C, 64.42; H, 7.47; N, 3.58. Found: C, 64.49; H, 7.33; N, 3.56.

Method C: General Method for the Conversion of Amino Acid Benzyl Esters to N-Sulfonyl Amino Acid Derivatives

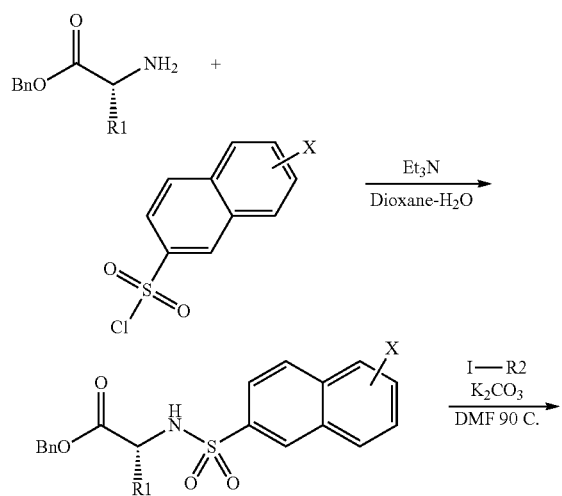

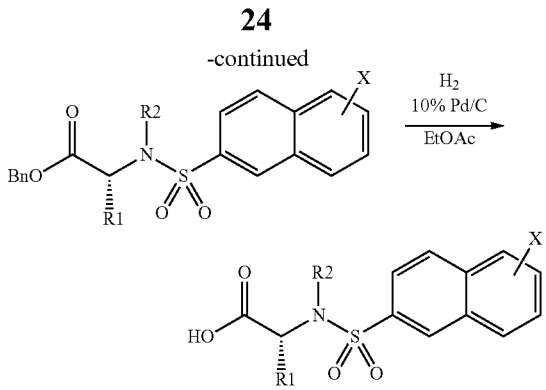

As to the individual steps in the above scheme, step 1 involves the sulfonylation of D-valine tert-butyl ester with a suitably substituted naphthalene-2-sulfonyl chloride to yield a substituted N-(naphthalene-2-sulfonyl)-D-valine tert-butyl ester. Step 2 involves the N-alkylation of the sulfonylamide, using an appropriate alkyl halide (e.g., 1-iodo-3-methylbutane or isoamyl iodide). Step 3 involves the deprotection of the benzyl ester via hydrogenolysis.

The sulfonylation and alkylation steps are carried out under analogous conditions as those described in methods A and B. The benzyl ester is converted to a carboxylic acid derivative following the typical procedure described below.

Typical Hydrogenation Procedure:

To a solution of 240 mg (0.44 mmol) 2-[(6-Benzyloxynaphthalene-2-sulfonyl)-(3-methyl-butyl)-amino]-3-methylbutyric acid tert-butyl ester in 20 ml EtOAc is added 50 mg PdC (10%) and the mixture is hydrogenated at 50 psi for 18 h. The mixture is filtered through Celite and evaporated to give the desired product.

Method D: Typical Procedure for the Conversion of Napthol Derivatives to Alkyl Derivatives

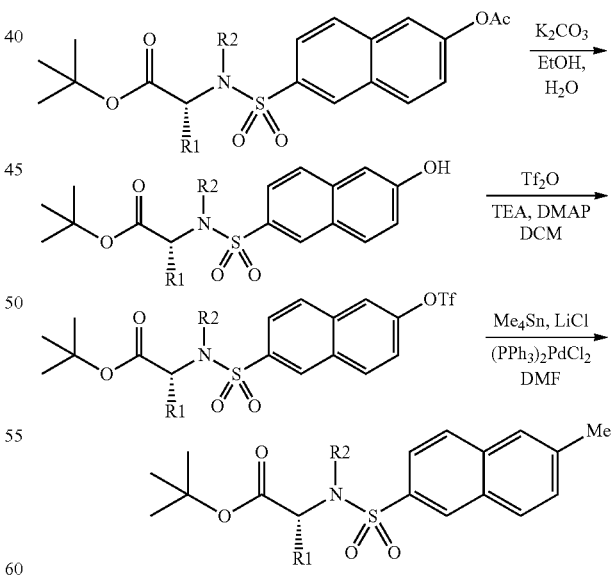

As to the individual steps in method D, step 1 involves the hydrolysis of the ester to provide the phenolic intermediate, step 2 involves the activation of the naphthol group into a trifluoromethanesulfonyl ester. Step 3 involves the displacement of the trifluoromethanesulfonyl ester with the desired substituent, e.g., a methyl group shown in the scheme above.

Once the substitution is completed, the product may be converted into the desired carboxylic acid according to the steps outlined in method A.

Typical Procedure for the Hydrolysis of Napthol Esters

N-Isoamyl-N-(6-hydroxy naphthalene-2-sulfonyl)-D-valine tert-butyl ester

To a solution of N-isoamyl-N-(6-acetoxy naphthalene-2-sulfonyl)-D-valine tert-butyl ester (0.75 g, 1.53 mmol) in ethanol-water (35 mL-15 mL) is added potassium carbonate (0.422 g, 3.05 mmol), and the reaction is heated to reflux for 16 h. The solvents are removed in vacuo, and the residue is redissolved in water and extracted three times with dichloromethane. The combined organic extracts are washed with sodium bicarbonate and brine, dried over sodium sulfate, and concentrated in vacuo. The crude product is purified by column chromatography (10% hexanes-ethyl acetate) to afford the title compound as a yellow oil (0.58 g, 85% yield).

N-isoamyl-N-(6-trifluoromethanesulfonyloxy naphthalene-2-sulfonyl)-D-valine tert-butyl ester To a solution of N-isoamyl-N-(6-hydroxy naphthalene-2-sulfonyl)-D-valine tert-butyl ester (0.18 g, 0.35 mmol) in dichloromethane (10 mL) at 0° C. is added triethylamine (0.099 mL, 0.71 mmol), triflic anhydride (0.089 mL, 0.53 mmol), and 4-dimethylaminopyridine (0.004 g, 0.035 mmol). The reaction is stirred at 0° C. for 1 hour. The solvents are removed in vacuo, and the residue is purified by column chromatography (6% hexanes-ethyl acetate) to afford the title compound (a triflate) as a yellow solid (0.14 g, 68% yield).

N-Isoamyl-N-(6-methyl naphthalene-2-sulfonyl)-D-valine tert-butyl ester

To a solution of N-isoamyl-N-(6-trifluoromethanesulfonyloxy naphthalene-2-sulfonyl)-D-valine tert-butyl ester (1.1 g, 1.89 mmol) in N,N-dimethylformamide (20 mL) is added lithium chloride (0.40 g, 9.5 mmol), tetramethyl tin (0.525 mL, 3.79 mmol), and bistriphenylphosphino palladium dichloride (0.066 g, 0.095 mmol). The reaction is heated to 80° C. for 16 h. The reaction is allowed to cool to ambient temperature and filtered through Celite. The filtrate is poured over water and extracted three times with dichloromethane. The combined organic extracts were washed with brine, dried over sodium sulfate, and concentrated in vacuo. The residue is purified by column chromatography (4% hexanes-ethyl acetate) to afford the title compound as a white solid (0.41 g, 50% yield).

Alternatively, different alkoxy substituted aryl compounds of formula (I) (where X=an alkoxy group) can be prepared from the suitably protected phenolic intermediate (tert-butyl shown for illustrative purposes) according to method E, which contains 1 steps. As illustrated in method E, this procedure involves the alkylation of the phenolic intermediate described above in method D with a suitable alkyl iodide (e.g. methyl iodide). The reaction conditions for the desired O-alkylation are analogous to the conditions for N-alkylation described in methods A and B. The conversion of the tert-butyl ester thus generated to the carboxylic acid is accomplished in the same manner described in method A.

Method E: Typical Procedure for the Alkylation of Napthol Derivatives

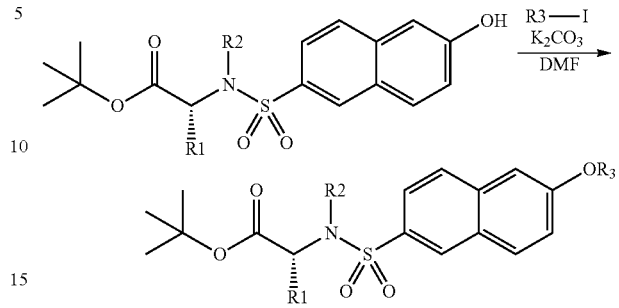

Alternatively, cyclic N-sulfonyl amino acid analogs of compounds of formula (I) can be prepared according to method F, which contains 6 steps.

Method F: Typical Procedure for the Formation of Tetrahydropyridine and Tetrahydroazepine Derivatives

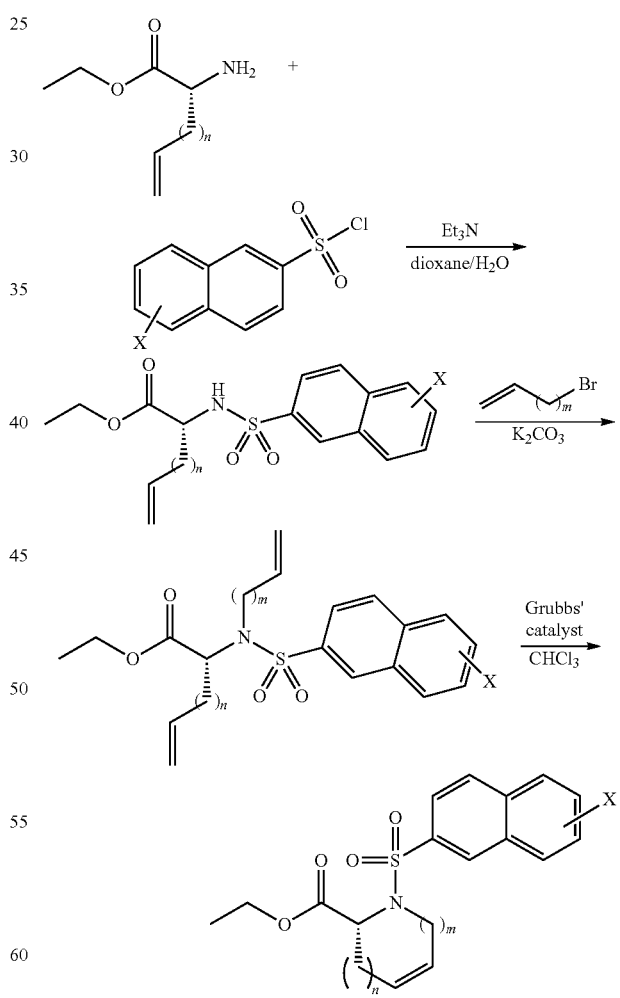

As to individual steps in method F, step 1 involves sulfonylation of a suitably protected amino acid derivative containing an olefin in the side chain. Step 2 involves the alkylation of the sulfonamide nitrogen. Steps 1 and 2 are analogous to the typical sulfonylation and alkylation conditions described in methods A and B. Step 3 involves a ring closing metathesis reaction to generate the cyclic amino acid. The resulting ester can be converted into the corresponding carboxylic acid by steps described in method B.

Step 3: Typical Procedure for Ring Closing Metathesis (R)-1-(1-Methoxy-naphthalene-2-sulfonyl)-1,2,3,6-tetrahydro-pyridine-2-carboxylic acid ethyl ester A solution of (R)-2-ally-1-(10methoxy-naphthalene-2sulfonyl)-amino-pent-4-enoic acid ethyl ester (141 mg, 0.35 mmol) in chloroform (5 mL) is de-gased with agon for 5 min, then Grubb's catalyst (5 mg, 0.006 mmol) is added. The reaction is stirred at room temperature for 15 min. The reaction is then concentrated in vacuo. Purification by flash chromatography yields the product (120 mg) as a solid. $^1$HNMR (400 MHz, MeOD): δ 0.92 (t, 3H, J=7 Hz), 2.65 (br, 2H), 3.8 (q, 1H, J=7 Hz), 3.95 (br, 2H), 4.15 (s, 3H), 5.03 (m, 1H), 5.65-5.75 (m, 2H), 7.65 (dd, 2H, J=2 Hz, J=6 Hz), 7.70 (d, 1H, J=8 Hz), 7.9 (m, 2H), 8.15 (m, 1H). LCMS (m/z): 376 (M+1).

Alternatively, substituted cyclic N-sulfonyl amino acid analogs of compounds of formula (I) can be prepared according to method G, which contains 4 steps.

Method G: Typical Procedure for the Alkylation of Napthol Derivatives

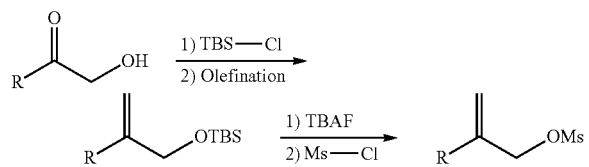

As to individual steps in method G, step 1 involves the protection of the hydroxy group as a suitable silyl ether. Step 2 involves the conversion of the ketone moiety to an olefin. Step 3 involves the deprotection of the silyl ether. Step four involves the formation of the methanesulfonic acid ester.

Typical Procedure for the Formation of Tert-Butyl Dimethylsilyl Ethers 2-(tert-Butyl-dimethyl-silanyloxy)-1-phenyl-ethanone To a well stirred solution of 2-hydroxyacetophenone (1.0 g, 7.34 mmol) in dichloromethane (15 mL) is added triethylamine (1.23 mL, 8.81 mmol), 4-dimethylaminopyridine (45 mg, 0.367 mmol) and tert-butyldimethylsilyl chloride (1.16 g, 7.71 mmol) dissolved in dichloromethane (2 mL). The reaction mixture is stirred at room temperature for 1 h, then diluted with dichloromethane (50 mL), washed with 10% citric acid, saturate sodium carbonate, brine, dried over magnesium sulfate, filtered and concentrated in vacuo. The residue is purified via silica gel chromatography (20% ethyl acetate in hexanes) to yield the title compound as a yellow oil (1.3 g, 5.19 mmol).

Typical Procedure for the Formation of Olefins from Ketones tert-Butyl-dimethyl-(2-phenyl-allyloxy)-silane To a well stirred solution of methyl-triphenyl-phosphonium bromide (3.08 g, 8.61 mmol) in tetrahydrofuran (10 mL) at 0° C. is added n-butyllithium (4.89 mL, 7.83 mmol of a 1.6 M solution). The reaction mixture is allowed to warm to room temperature, stirred for 1 h, then cooled to 0° C. 2-(tert-butyl-dimethyl-silanyloxy)-1-phenyl-ethanone (980 mg, 3.91 mmol) in tetrahydrofuran (30 mL) is then slowly added. The mixture is stirred at room temperature for 30 min then quenched by the addition of a saturated aqueous solution of ammonium chloride and extracted several times with ethyl acetate. The organic layers are combined, washed with water, brine, dried over magnesium sulfate, filtered and concentrated in vacuo. The residue is purified via silica gel chromatography (20% ethyl acetate in hexanes) to yield 1.3 g of the title compound as a clear oil containing ethyl acetate and was used directly in the next step.

Typical Procedure for the Deprotection of Tert-Butyl Dimethylsilyl Ethers

2-Phenyl-prop-2-en-1-ol

To a well stirred solution of tert-butyl-dimethyl-(2-phenyl-allyloxy)-silane (1.3 g, 5.23 mmol) in tetrahydrofuran (10 mL) is slowly added a solution of a 1 N tetrabutylammonium fluoride in tetrahydrofuran (10.5 mL, 10.5 mmol). The reaction is allowed to stir for 20 min, quenched by the addition of a saturated aqueous solution of ammonium chloride and extracted several times with ethyl acetate The organic layers are combined, washed with water, brine, dried over magnesium sulfate, filtered and concentrated in vacuo. The residue is purified via silica gel chromatography (10% ethyl acetate in hexanes) to yield 700 mg of the title compound.

Typical Procedure for the Formation of Methanesulfonic Acid Esters

Methanesulfonic acid 2-phenyl-allyl ester

To a well stirred solution of 2-phenyl-prop-2-en-1-ol (700 mg, 5.22 mmol) in dichlorometane (10 mL) at 0° C. is added triethylamine (0.945 mL, 6.78 mmol) and methylsulfonyl chloride (0.424 mL, 5.48 mmol). The reaction is allowed to stir for 10 min, warmed to room temperature and is stirred for 30 min. The reaction is quenched by the addition of a saturated aqueous solution of ammonium chloride and extracted several times with ethyl acetate. The organic layers are combined, washed with 1 N hydrochloric acid, brine, dried over magnesium sulfate, filtered and concentrated in vacuo. The residue is purified via silica gel chromatography (10% ethyl acetate in hexanes) to yield the title compound (1.07 g, 4.95 mmol).

The resulting methanesulfonic acid esters are converted to the desired carboxylic acid derivative by method F as shown below.

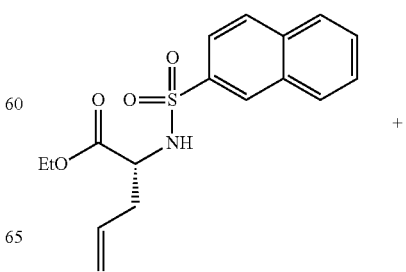

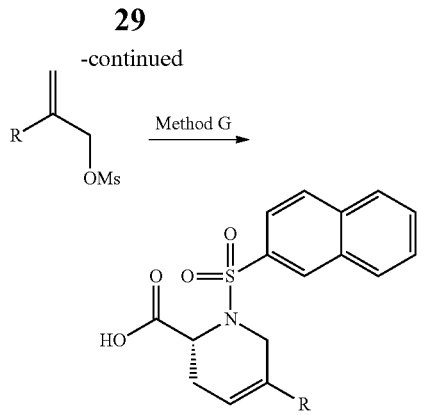

Alternatively, bicyclic N-sulfonyl amino acid analogs of compounds of formula (I) can be prepared according to method H, which contains 7 steps.

Method H: Typical Procedure for the Hydrogenation of Tetrahydropiperidine and Tetrahydroazepine Analogs To a mixture of (R)-1-(quinoline-3-sulfonyl)-piperidine-2-carboxylic acid hydroxyamide (110 mg) in ethanol (5 mL) is added 10% palladium on carbon (10 mg). The reaction mixture is maintained under 1 atmosphere of hydrogen for 18 h. The reaction mixture is filtered through Celite, and concentrated in vacuo yield a product (85 mg) as a light beige solid.

General Methods for the Formation of Hydroxamates

Method I: General Method for the Conversion of Carboxylic Acid Derivatives to Hydroxyamide Compounds Via Hydroxylamine Method J: General Method for the Conversion of Carboxylic Acid Derivatives to Hydroxyamide Compounds Via Acid Chloride

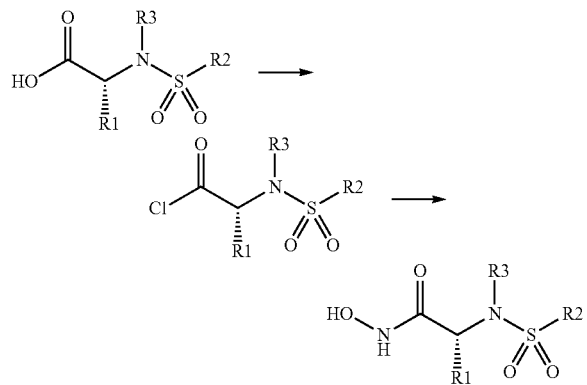

As to the individual steps in the above scheme, step 1 involves activation of the carboxylic acid as the acid chloride. Step 2 involves the substitution of the acid chloride with hydroxylamine to yield the desired hydroxamic acid.

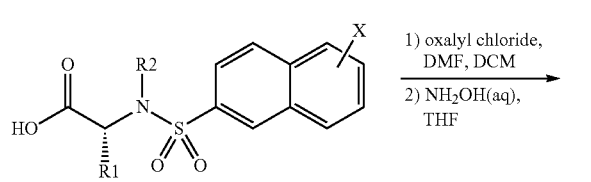

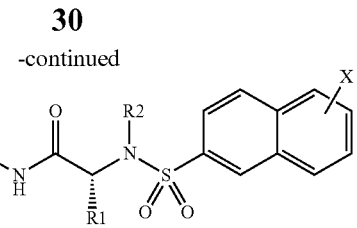

Typical Procedure for the Formation of N-Hydroxyamides Via Acid Chlorides

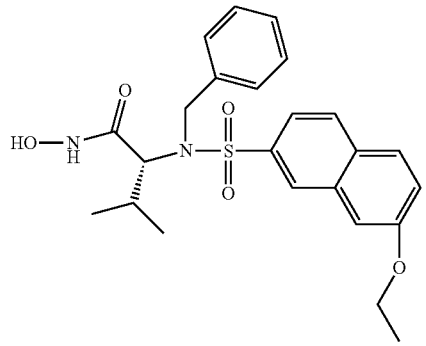 [SMILES: CCOc1ccc2ccc(S(=O)(=O)N(Cc3ccccc3)[C@@H](C(=O)NO)C(C)C)cc2c1]

N-Benzyl-N-(7-ethoxy-naphthalene-2-sulfonyl)-D-valine hydroxamic acid (NVP-LBQ690) (Converted from the carboxylic acid to the hydroxamic acid via the acid chloride)

To a solution of N-benzyl-N-(7-ethoxy-naphthalene-2-sulfonyl)-D-valine (0.335 mg, 0.76 mmol) in dichloromethane (20 ml) is added 5 drops of DMF and 2 M oxalyl chloride (1 ml, 2 mmol). After 1 hour the reaction is complete by TLC. The mixture is transferred dropwise to a cooled (0° C.) mixture of 50% aqueous hydroxylamine (3 ml, 2 mmol) in THF (25 ml). After stirring for 1 hour the reaction is washed with 1 N hydrochloric acid, saturated sodium chloride solution, dried over MgSO$_4$, filtered and concentrated. The crude product is purified by column chromatography (hexane-ethyl acetate; 1:1) and crystallized from diethyl ether affording the title compound. Mass spectrum (457.2; M+1, 455.4; M−1). CHN Calc CHN 63.14, 6.18, 6.14. Found CHN 63.17, 6.11, 6.01.

Alternatively, compounds of the general formula I can be prepared from the carboxylic acid intermediates as described above, according to method J, which contains 2 steps.

Method K: General Method for the Conversion of Carboxylic Acid Derivatives to Hydroxyamide Compounds Via O-Tetrahydropyranylhyrdroxylamine

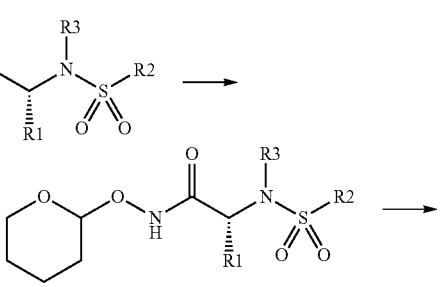

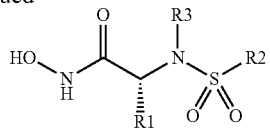

Typical Procedure for Making O-Tetrahydropyranyl N-Hyrdroxyamide

Following the procedure for the formation of O-tritylhydroxylamine compounds, O-tetrahydropyranyl N-hyrdroxyamides can be prepared by analogous methods where O-tetrahydropyranylhyrdroxylamine is used instead of O-tritylhydroxylamine.

General Procedure for the Deprotection of O-Tetrahydropyranyl N-Hyrdroxyamide

To a solution of the tetrahydropyranyl protected hydroxamic acid is added ethanol and 3 N hydrochloric acid and the reaction stirred at ambient temperature for 16 hours. Water and ethyl acetate are added, the aqueous layer neutralized with sodium bicarbonate and the layers separated. The aqueous layer is extracted with ethyl acetate, washed with brine, dried over magnesium sulfate and filtered. The solvent is removed in vacuo and the residue is purified by crystallization from diethyl ether and hexane to give the desired product As to the individual steps in the above scheme, step 1 involves coupling of the carboxylic acid with tetrahydropyranyl (tetrahydropyranyl) protected hydroxylamine. Step 2 involves removal of the tetrahydropyranyl protecting group via acid hydrolysis to yield the desired hydroxamic acid.

Method L: General Method for the Conversion of Carboxylic Acid Derivatives to Hydroxyamide Compounds Via O-Tritylhyrdroxylamine

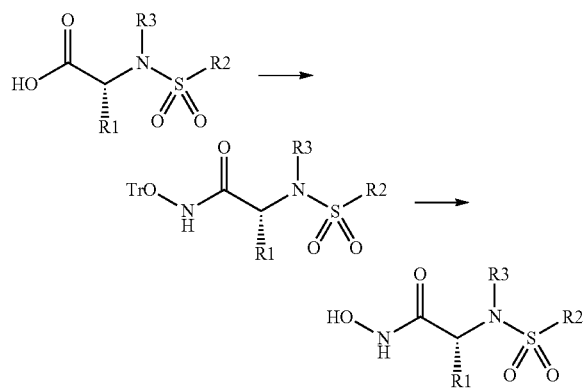

Typical Procedure for Making O-Trityl Hydroxyamide Compounds:

A solution of acid (460 mg, 1.18 mmol), O-tritylhydroxyamine (485 mg, 1.76 mmol), N-methyl morpholine (594 mg, 5.88 mmol), 1-hydroxy-7-azabenzo-triazole (160 mg, 1.18 mmol), and 1-(3-(dimethylamino)propyl)-3-ethylcarbodiimide hydrochloride (293 mg, 1.53 mmol) in dichloromethane (20 mL) are stirred at room temperature for 18 h. The reaction is then acidified with 1 N hydrochloric acid and extracted with dichloromethane. The combined organic extracts are washed with brine, dried over sodium sulfate, and concentrated in vacuo to give 810 mg of product as white solid which is carried on without any further purification. LCMS (m/z): 647 (M−1).

Typical Procedure for the Deprotection of O-Trityl Hydroxyamide Compounds:

To a solution of trityl protected hydroxylamine compound (400 mg, 0.62 mmol) in dichloromethane (10 mL) is added trifluoroacetic acid (563 mg, 4.9 mmol) followed by the addition of triethylsilane (143 mg, 1.23 mmol). The reaction is stirred at room temperature for 5 minutes, then concentrated in vacuo to give a crude product, which is purified by flash chromatography to afford product (280 mg) as white solid.

Alternatively, hydroxamates may be prepared directly from carboxylic acid derivatives and hydroxylamine (50% solution in water) following method L except the final deprotection step is omitted.

Generally, the compounds of formula (II) can be prepared by methods of preparing enantiomers of the compounds known to those skilled in the art by resolving racemic mixtures, such as by formation and recrystallization of diastereomeric salts or by chiral chromatography or HPLC separation utilizing chiral stationery phases.

Preferably, the compounds of formula (II) can be prepared starting with materials in the form of the intended enantiomer and using the schemes described herein, such that the resulting final compounds are in the form of the intended enantiomer.

In starting compounds and intermediates which are converted to the compounds of the present invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, carboxy, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, at or near the boiling point of the solvents used, and at atmospheric or super-atmospheric pressure.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known.

The present invention will now be illustrated by reference to the following examples which set forth particularly advantageous embodiments. However, it should be noted that these embodiments are illustrative and are not to be construed as restricting the invention in any way.

Other analogs (e.g., ethyl, propyl, etc.) may also be prepared by this procedure. In addition, one of ordinary skill in the art would appreciate that the triflate intermediate may also be displaced with other nucleophiles, such as amines (RNH$_2$ or RR'NH) or thiols (RSH).

The above tert-butyl ester can then be deprotected (with TFA) to produce a free carboxylic acid. The carboxylic acid can then be converted into a trityl hydroxamic acid, which is subsequently deprotected to produce the desired hydroxamic acid, according to the procedures shown in Scheme I.

Example 1

(R)—N-Hydroxy-2-[(1-hydroxy-naphthalene-2-sulfonyl)-(3-methyl-butyl)-amino]-3-methyl-butyramide

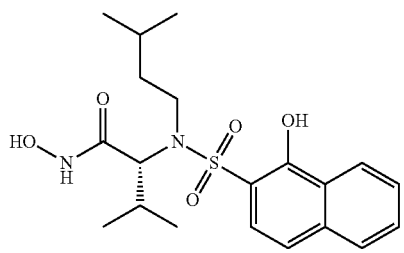 [SMILES: CC(C)CCN([C@@H](C(=O)NO)C(C)C)S(=O)(=O)c1ccc2ccccc2c1O]

Following methods A and L, the title compound is prepared from (R)-2-amino-3-methyl-butyric acid tert-butyl ester, 1-methoxy-naphthalene-2-sulfonyl chloride and 1-bromo-3-methyl-butane. Analytical data: LCMS (m/z): 409 (M+1).

Example 2

N-Hydroxy-2-[isobutyl-(naphthalene-2-sulfonyl)-amino]-acetamide

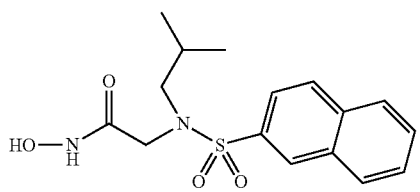 [SMILES: CC(C)CN(CC(=O)NO)S(=O)(=O)c1ccc2ccccc2c1]

Following methods B and L, the title compound is prepared from amino-acetic acid, naphthalene-2-sulfonyl chloride and 1-bromo-3-methyl-butane. LCMS (m/z): 393.1 (M+1).

Example 3

(R)-2-(Naphthalene-2-sulfonylamino)-pent-4-enoic acid hydroxyamide

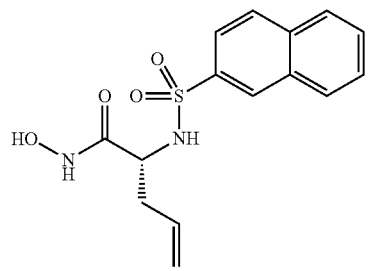 [SMILES: C=CC[C@@H](NS(=O)(=O)c1ccc2ccccc2c1)C(=O)NO]

Following typical sulfonylation methods and method L, the title compound is prepared from (R)-2-amino-pent-4-enoic acid ethyl ester and naphthalene-2-sulfonyl chloride. LCMS (m/z): 321 (M+1). Analytics calculated for $C_{15}H_{16}N_2O_4S$: C, 56.24; H, 5.03; N, 8.74. Found: C, 56.87; H, 4.84; N, 8.42.

Example 4

(R)-2-[But-3-enyl-(naphthalene-2-sulfonyl)-amino]-pent-4-enoic acid hydroxyamide

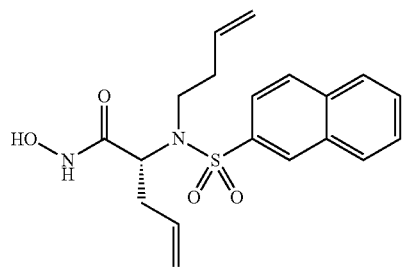 [SMILES: C=CCCN([C@H](CC=C)C(=O)NO)S(=O)(=O)c1ccc2ccccc2c1]

Following typical sulfonylation and alkylation methods followed by method L, the title compound is prepared from (R)-2-amino-pent-4-enoic acid ethyl ester, naphthalene-2-sulfonyl chloride and 4-bromo-but-1-ene. LCMS (m/z): 375 (M+1). Analytics calculated for $C_{19}H_{22}N_2O_4S$: C, 60.94; H, 5.92; N, 7.48. Found: C, 60.73; H, 5.87; N, 7.27.

Example 5

4-Methyl-2-(naphthalene-2-sulfonylamino)-pentanoic acid hydroxyamide

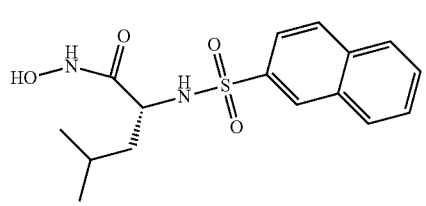 [SMILES: CC(C)C[C@@H](NS(=O)(=O)c1ccc2ccccc2c1)C(=O)NO]

Following typical sulfonylation conditions and method J, the title compound is prepared from (R)-2-amino-4-methyl-pentanoic acid and naphthalene-2-sulfonyl chloride. LCMS (m/z): 337.2 (M+1), 335.33 (M−1).

Example 6

N-Hydroxy-3-methyl-2-(naphthalene-2-sulfonylamino)-butyramide

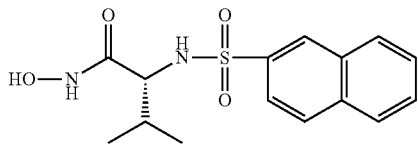 [SMILES: CC(C)[C@@H](NS(=O)(=O)c1ccc2ccccc2c1)C(=O)NO]

Following typical sulfonylation conditions and method L, the title compound is prepared from (R)-2-amino-3-methyl-butyric acid tert-butyl ester and naphthalene-2-sulfonyl chloride. LCMS (m/z): 321.10 (M−1).

Example 7

(R)—N-Hydroxy-2-[(3-methyl-butyl)-(naphthalene-2-sulfonyl)-amino]-4-phenyl-butyramide

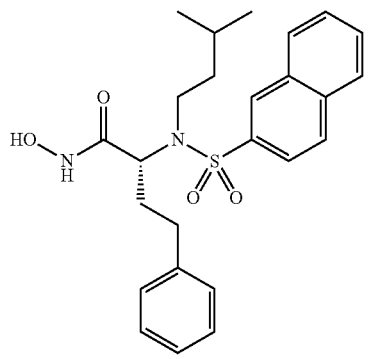 [SMILES: CC(C)CCN([C@H](CCc1ccccc1)C(=O)NO)S(=O)(=O)c1ccc2ccccc2c1]

Following methods B and L, the title compound is prepared from (R)-2-amino-4-phenyl-butyric acid, naphthalene-2-sulfonyl chloride and 1-iodo-3-methyl-butane. $^1$HNMR (400 MHz, MeOD): δ 0.88 (d, 6H, J=6 Hz), 1.45-1.60 (m, 4H), 1.61-1.72 (m, 1H), 2.05-2.20 (m, 1H), 2.35-2.55 (m, 2H), 3.55-3.70 (m, 1H), 4.25 (m, 1H), 6.92 (d, 2H, J=8 Hz), 7.10-7.20 (m, 3H), 7.60-7.75 (m, 3H) 7.98-8.07 (m, 3H), 8.38 (s, 1H). LCMS (m/z): 455 (M+1). Analytics calculated for $C_{25}H_{30}N_2O_4S$: C, 66.05; H, 6.65; N, 6.16. Found: C, 65.97; H, 6.49; N, 5.98.

Example 8

(R)-2-[Allyl-(naphthalene-2-sulfonyl)-amino]-pent-4-ynoic acid hydroxyamide

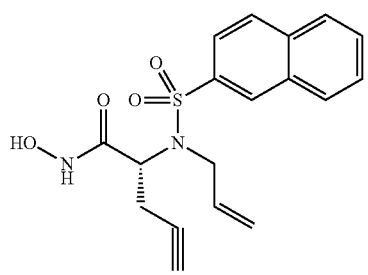 [SMILES: C#CC[C@H](C(=O)NO)N(CC=C)S(=O)(=O)c1ccc2ccccc2c1]

Following typical sulfonylation and alkylation methods followed by method L, the title compound is prepared from (R)-2-amino-pent-4-ynoic acid ethyl ester, naphthalene-2-sulfonyl chloride and 3-bromo-propene. LCMS (m/z): 359 (M+1).

Example 9

(R)-1-(Naphthalene-2-sulfonyl)-piperidine-2-carboxylic acid hydroxyamide

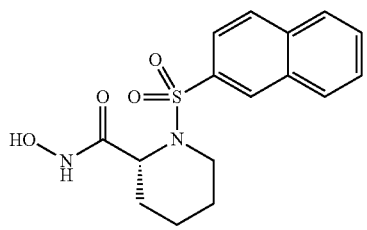 [SMILES: O=C(NO)[C@H]1CCCCN1S(=O)(=O)c1ccc2ccccc2c1]

Following method H, the title compound is prepared from (R)-1-(naphthalene-2-sulfonyl)-1,2,3,6-tetrahydro-pyridine-2-carboxylic acid hydroxyamide. LCMS (m/z): 335 (M+1). Analytics calculated for $C_{19}H_{22}N_2O_4S$: C, 57.47; H, 5.43; N, 19.14. Found: C, 53.11; H, 5.09; N, 7.24.

Example 10

2-[Benzyl-(naphthalene-2-sulfonyl)-amino]-N-hydroxy-3-methyl-butyramide

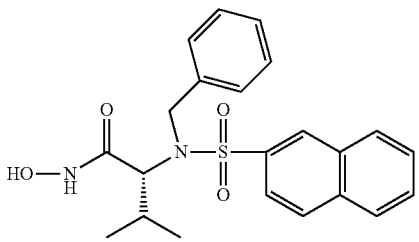 [SMILES: CC(C)[C@H](C(=O)NO)N(Cc1ccccc1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and benzyl bromide. LCMS (m/z): 411.16 (M−1).

Example 11

N-Hydroxy-2-(naphthalene-2-sulfonylamino)-2-(tetrahydro-pyran-4-yl)-acetamide

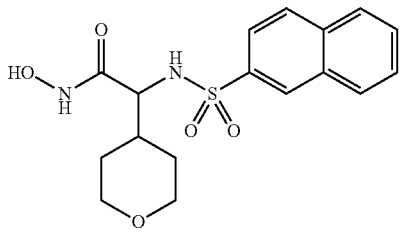 [SMILES: O=C(NO)C(NS(=O)(=O)c1ccc2ccccc2c1)C1CCOCC1]

Following methods B and L, the title compound is prepared from amino-(tetrahydro-pyran-4-yl)-acetic acid and naphthalene-2-sulfonyl chloride. LCMS (m/z): 365.3 (M+1), 363.4 (M−1). CHN: Calc CHN: 56.03, 5.53, 7.69. Found CHN: 56.66, 5.71, 7.23.

Example 12

N-Hydroxy-2-methyl-2-(naphthalene-2-sulfonylamino)-propionamide

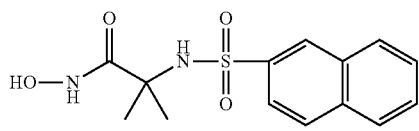 [SMILES: CC(C)(NS(=O)(=O)c1ccc2ccccc2c1)C(=O)NO]

Following typical sulfonylation conditions and method L, the title compound is prepared from 2-amino-2-methyl-propionic acid and naphthalene-2-sulfonyl chloride. LCMS (m/z): 307.21 (M−1).

Example 13

(R)—N-Hydroxy-3-methyl-2-[(naphthalene-2-sulfonylphenethyl-amino]-butyramide

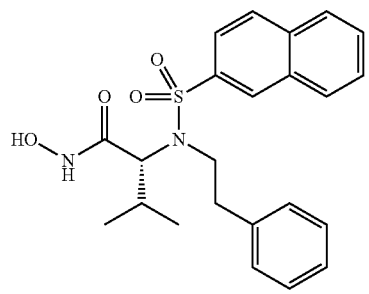 [SMILES: CC(C)[C@H](C(=O)NO)N(CCc1ccccc1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and (2-bromo-ethyl)-benzene. LCMS (m/z): 427 (M+1). Analytics calculated for $C_{23}H_{26}N_2O_4S$: C, 64.77; H, 6.14; N, 6.57. Found: C, 64.57; H, 6.02; N, 6.53.

Example 14

N-Hydroxy-3-methyl-2-[(naphthalene-2-sulfonyl)-(3-phenyl-propyl)-amino]-butyramide

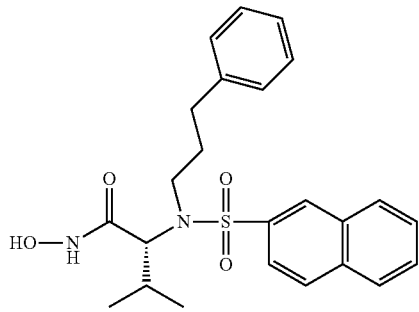 [SMILES: CC(C)[C@H](C(=O)NO)N(CCCc1ccccc1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and (3-bromo-propyl)-benzene. LCMS (m/z): 439.15 (M−1)

Example 15

(R)-4-Methyl-2-[(3-methyl-butyl)-(naphthalene-2-sulfonyl)-amino]-pentanoic acid hydroxyamide

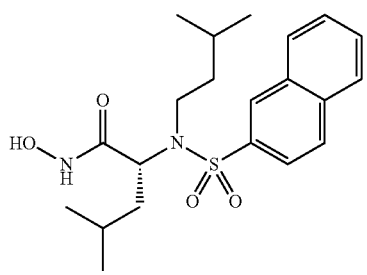 [SMILES: CC(C)CCN([C@H](CC(C)C)C(=O)NO)S(=O)(=O)c1ccc2ccccc2c1]

Following methods B and L, the title compound is prepared from butane (R)-2-amino-4-methyl-pentanoic acid methyl ester, naphthalene-2-sulfonyl chloride and 1-iodo-3-methyl-butane. $^1$HNMR (400 MHz, MeOD): δ 0.80 (q, 6H, J=3.6 Hz), 0.90 (d, 6H, J=6 Hz), 1.25 (m, 1H), 1.4-1.6 (m, 2H), 1.62-1.75 (m, 2H), 3.58-3.60 (m, 1H), 4.27-4.42 (t, 1H, J=7 Hz), 7.6-7.7 (m, 2H), 7.82 (d, 1H, J=8.5 Hz), 7.98 (d, 1H, J=8.5 Hz), 8.07 (d, 1H, J=8.5 Hz), 8.45 (s, 1H). LCMS (m/z): 407 (M+1). Analytics calculated for $C_{21}H_{30}N_2O_4S$: C, 62.04; H, 7.44; N, 6.89. Found: C, 62.32; H, 7.34; N, 6.71

Example 16

(R)—N-Hydroxy-3-(4-hydroxy-phenyl)-2-[(3-methyl-butyl)-(naphthalene-2-sulfonyl)-amino]-propionamide

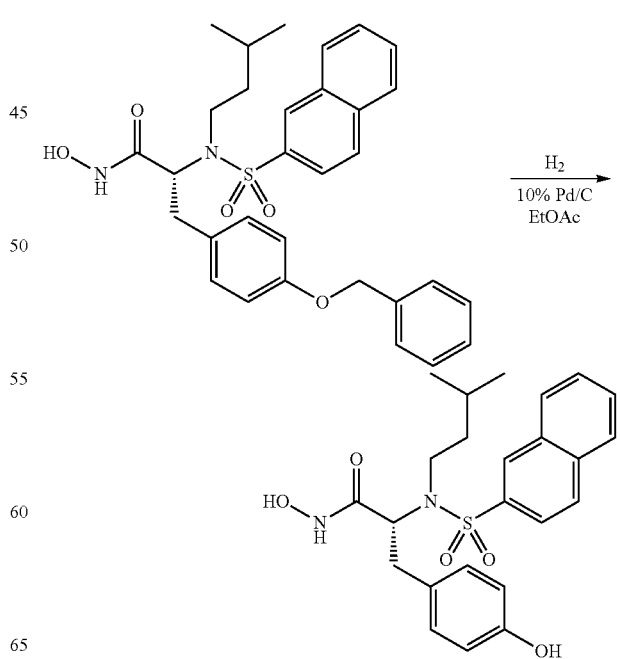

A mixture of (R)-3-(4-benzyloxy-phenyl)-N-hydroxy-2-[(3-methyl-butyl)-(naphthalene-2-sulfonyl)-amino]-propionamide (230 mg, 0.42 mmol) and 200 mg of 10% Pd/C in ethyl acetate (20 mL) are hydrogenated under 50 PSI for 6 h. The reaction mixture is filtered through celite, and concentrated in vacuo. Purification by flash chromatography yields 40 mg of product. $^1$HNMR (400 MHz, MeOD): δ 0.90 (d, 6H, J=5.5 Hz), 1.5-1.7 (m, 4H), 2.4-2.5 (dd, 1H, J=5 Hz), 3.05-3.15 (dd, 1H, J=5 Hz), 3.35-3.45 (m, 1H), 3.6-3.75 (m, 1H), 4.30-4.40 (q, 1H, J=5 Hz), 6.55 (d, 2H, J=8 Hz), 6.80 (d, 2H, J=8 Hz), 7.7-7.85 (m, 3H), 7.92-8.10 (m, 3H), 8.45 (s, 1H). LCMS (m/z): 457 (M+1). Analytics calculated for $C_{24}H_{28}N_2O_{54}S$: C, 63.14; H, 6.18; N, 6.14. Found: C, 63.03; H, 6.30; N, 5.89.

Example 17

N-methyl-N-(naphthalene-2-sulfonyl)-D-valine hydroxamic acid

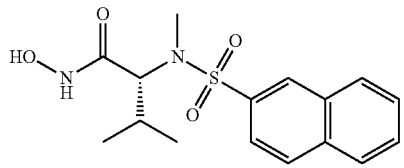 [SMILES: CC(C)[C@H](C(=O)NO)N(C)S(=O)(=O)c1ccc2ccccc2c1]

Following methods A and L, the title compound is prepared from (R)-2-amino-3-methyl-butyric acid tert-butyl ester, naphthalene-2-sulfonyl chloride and methyl iodide. LCMS (m/z): 337.18 (M+1), 335.29 (M−1).

Example 18

N-Hydroxy-4-methanesulfonyl-2-(naphthalene-2-sulfonylamino)-butyramide

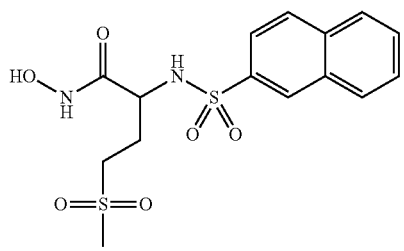 [SMILES: CS(=O)(=O)CCC(NS(=O)(=O)c1ccc2ccccc2c1)C(=O)NO]

Following typical sulfonylation conditions and method L, the title compound is prepared from 2-amino-4-methanesulfonyl-butyric acid and naphthalene-2-sulfonyl chloride. LCMS (m/z): 387.2 (M+1), 385.3 (M−1).

Example 19

1-(Naphthalene-2-sulfonylamino)-cyclohexanecarboxylic acid hydroxyamide

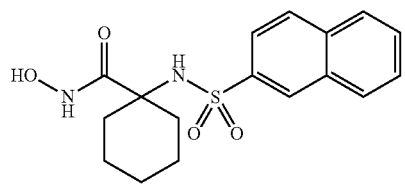 [SMILES: O=C(NO)C1(NS(=O)(=O)c2ccc3ccccc3c2)CCCCC1]

Following typical sulfonylation conditions and method L, the title compound is prepared from 1-amino-cyclohexanecarboxylic acid and naphthalene-2-sulfonyl chloride. LCMS (m/z): 349.3 (M+1), 347.3 (M−1).

Example 20

(R)—N-Hydroxy-2-[(3-methyl-butyl)-(naphthalene-2-sulfonyl)-amino]-4-methylsulfanyl-butyramide

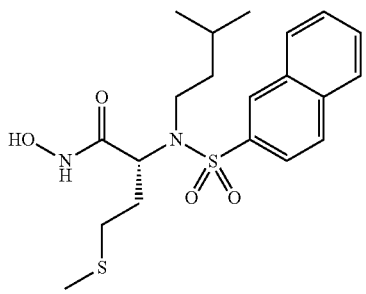 [SMILES: CSCC[C@H](C(=O)NO)N(CCC(C)C)S(=O)(=O)c1ccc2ccccc2c1]

Following methods B and L, the title compound is prepared from (R)-2-tert-butoxycarbonylamino-4-methylsulfanyl-butyric acid, naphthalene-2-sulfonyl chloride and 1-iodo-3-methyl-butane. $^1$HNMR (400 MHz, MeOD): δ 0.88 (d, 6H, J=6 Hz), 1.41-1.60 (m, 4H), 2.02-2.38 (m, 4H), 3.55-3.70 (m, 1H), 4.45 (t, 1H, J=7 Hz), 7.60-7.70 (m, 2H), 7.85 (dd, 1H, J=2 Hz, J=7 Hz), 7.97 (d, 1H, J=7 Hz), 8.04 (d, 2H, J=8 Hz), 8.48 (s, 1H). LCMS (m/z): 425 (M+1). Analytics calculated for $C_{20}H_{28}N_2O_4S_2$: C, 56.58; H, 6.65; N, 6.60. Found: C, 55.93; H, 6.71; N, 6.32.

Example 21

(R)-3,N-Dihydroxy-2-[(3-methyl-butyl)-(naphthalene-2-sulfonyl)-amino]-propionamide

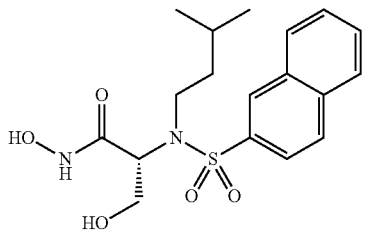 [SMILES: CC(C)CCN([C@H](CO)C(=O)NO)S(=O)(=O)c1ccc2ccccc2c1]

Following methods B and L, the title compound is prepared from (R)-2-amino-3-tert-butoxy-propionic acid methyl ester, naphthalene-2-sulfonyl chloride and 1-iodo-3-methyl-butane. ¹HNMR (400 MHz, MeOD): δ 0.88 (d, 6H, J=6 Hz), 1.45-1.65 (m, 4H), 3.50-3.59 (m, 1H), 3.6-3.75 (m, 2H), 3.8-3.9 (m, 1H), 4.40 (t, 1H, J=7 Hz), 7.60-7.70 (m, 2H), 7.85 (dd, 1H, J=2 Hz, J=7 Hz), 7.97-8.05 (m, 3H), 8.45 (s, 1H). LCMS (m/z): 381 (M+1). Analytics calculated for $C_{18}H_{24}N_2O_5S$: C, 56.83; H, 6.36; N, 7.36. Found: C, 56.38; H, 6.40; N, 7.07.

Example 22

N-Hydroxy-3-methyl-2-[(3-methyl-butyl)-(naphthalene-2-sulfonyl)-amino]-butyramide

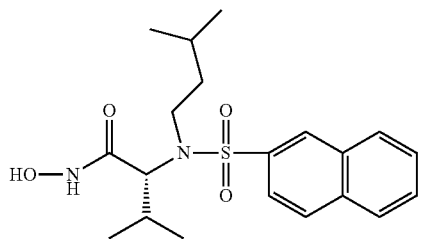 [SMILES: CC(C)CCN([C@@H](C(=O)NO)C(C)C)S(=O)(=O)c1ccc2ccccc2c1]

Following methods A and L, the title compound is prepared from (R)-2-amino-3-methyl-butyric acid tert-butyl ester, naphthalene-2-sulfonyl chloride and 1-bromo-3-methyl-butane. LCMS (m/z): 393.1 (M+1).

Example 23

(S)-3-(Naphthalene-2-sulfonyl)-thiazolidine-4-carboxylic acid hydroxyamide

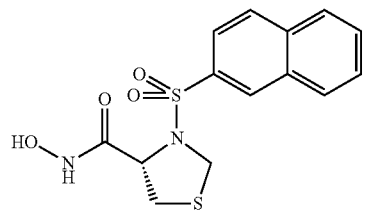 [SMILES: O=C(NO)[C@H]1CSCN1S(=O)(=O)c1ccc2ccccc2c1]

Following typical methods for sulfonylation and method L, the title compound is prepared from (S)-thiazolidine-4-carboxylic acid and naphthalene-2-sulfonyl chloride. LCMS (m/z): 339 (M+1). Analytics calculated for $C_{14}H_{13}N_2O_4S_2$: C, 49.69; H, 4.17; N, 8.28. Found: C, 49.84; H, 4.15; N, 8.03.

Example 24

(R)-2-[Allyl-(naphthalene-2-sulfonyl)-amino]-N-hydroxy-3-methyl-butyramide

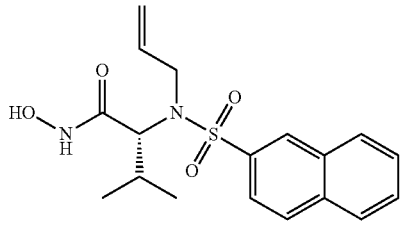 [SMILES: C=CCN([C@@H](C(=O)NO)C(C)C)S(=O)(=O)c1ccc2ccccc2c1]

Following methods A and L, the title compound is prepared from (R)-2-amino-3-methyl-butyric acid tert-butyl ester, naphthalene-2-sulfonyl chloride and 3-bromo-propene. Analytical data: LCMS (m/z): 363 (M+1).

Example 25

(R)-3-(4-Benzyloxy-phenyl)-N-hydroxy-2-[(3-methyl-butyl)-(naphthalene-2-sulfonyl)-amino]-propionamide

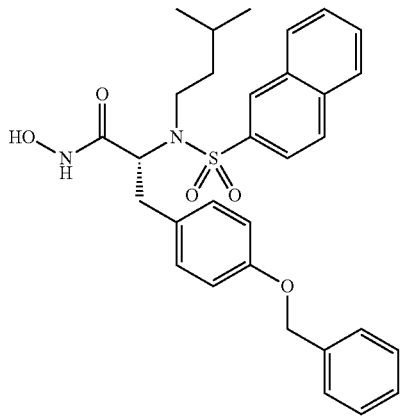 [SMILES: CC(C)CCN([C@H](Cc1ccc(OCc2ccccc2)cc1)C(=O)NO)S(=O)(=O)c1ccc2ccccc2c1]

Following methods B and L, the title compound is prepared from (R)-2-amino-3-(4-benzyloxy-phenyl)-propionic acid, naphthalene-2-sulfonyl chloride and 1-iodo-3-methyl-butane. ¹HNMR (400 MHz, MeOD): δ 0.90 (d, 6H, J=6 Hz), 1.50-1.65 (m, 4H), 2.45-2.58 (m, 1H), 3.02-3.13 (m, 1H), 3.35-3.48 (m, 1H), 3.60-3.71 (m, 1H), 4.3-4.48 (m, 1H), 4.95 (s, 2H), 6.65 (d, 2H, J=8.5 Hz), 6.89 (d, 2H, J=8.5 Hz), 7.28-7.40 (m, 5H), 7.60-8.05 (m, 3H), 7.95-8.05 (m, 3H), 8.42 (s, 1H). LCMS (m/z): 547 (M+1).

Example 26

(R)-1-(Naphthalene-2-sulfonyl)-1,2,3,6-tetrahydropyridine-2-carboxylic acid hydroxyamide

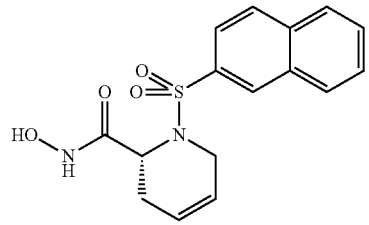 [SMILES: O=C(NO)[C@H]1CC=CCN1S(=O)(=O)c1ccc2ccccc2c1]

Following methods B, G and L, the title compound is prepared from (R)-2-amino-pent-4-enoic acid ethyl ester, naphthalene-2-sulfonyl chloride and 3-bromo-propene. LCMS (m/z): 333 (M+1).

Example 27

2-[Benzyl-(7-ethoxy-naphthalene-2-sulfonyl)-amino]-N-hydroxy-3-methyl-butyramide

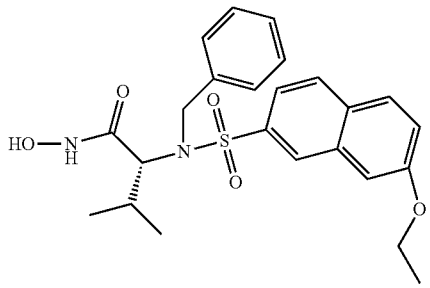 [SMILES: CCOc1ccc2ccc(S(=O)(=O)N(Cc3ccccc3)[C@@H](C(=O)NO)C(C)C)cc2c1]

Following methods A, E and J, the title compound is prepared from (R)-2-amino-3-methyl-butyric acid tert-butyl ester, 7-hydroxy-naphthalene-2-sulfonyl chloride, chloroethane and benzyl bromide. LCMS (m/z): 457.2 (M+1), 455.4 (M−1). CHN Calc C, 63.14; H, 6.18; N, 6.14. Found C, 63.17; H, 6.11; N, 6.01.

Example 28

(R)—N-Hydroxy-3-methyl-2-[(naphthalene-2-sulfonyl)-pyridin-4-ylmethyl-amino]-butyramide

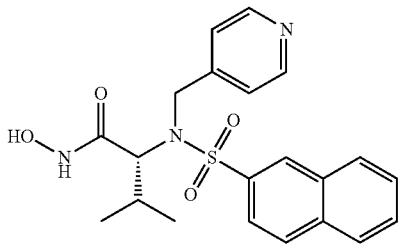 [SMILES: CC(C)[C@H](C(=O)NO)N(Cc1ccncc1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and 4-bromomethyl-pyridine. LCMS (m/z): 414 (M+1). Analytics calculated for $C_{21}H_{23}N_3O_4S$: 0, 61; H, 5.61; N, 10.16. Found: C, 59.29; H, 5.95; N, 9.92.

Example 29

N-isoamyl-N-(6-ethyl naphthalene-2-sulfonyl)-D-valine hydroxamic acid

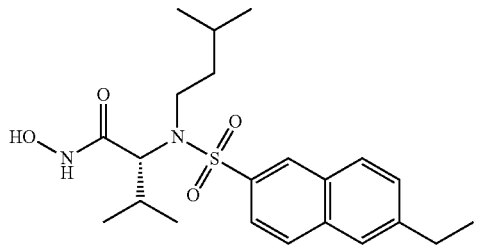 [SMILES: CCc1ccc2cc(S(=O)(=O)N(CCC(C)C)[C@@H](C(=O)NO)C(C)C)ccc2c1]

Following methods A, D and L, the title compound is prepared from (R)-2-amino-3-methyl-butyric acid tert-butyl ester, acetic acid 6-chlorosulfonyl-naphthalen-2-yl ester, tetraethyl-stannane and 1-bromo-3-methyl-butane. LCMS (m/z): 419.32 (M−1). CHN Calc C, 62.04; H, 7.44; N, 6.89. Found C, 61.88; H, 7.38; N, 6.79.

Example 30

N-(2-phenoxyethyl)-N-(naphthalene-2-sulfonyl)-D-valine hydroxamic acid

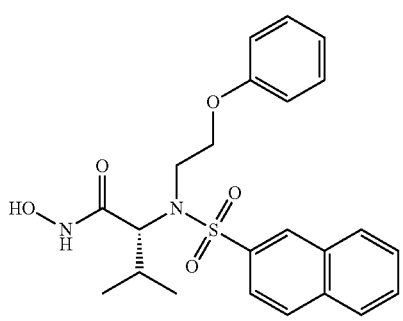 [SMILES: CC(C)[C@H](C(=O)NO)N(CCOc1ccccc1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and (2-bromo-ethoxy)-benzene. LCMS (m/z): 443.29 (M+1), 441.37 (M−1).

Example 31

N-Hydroxy-2-[(6-hydroxy-naphthalene-2-sulfonyl)-(3-methyl-butyl)-amino]-3-methyl-butyramide

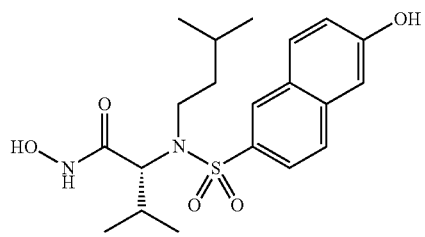 [SMILES: CC(C)CCN([C@@H](C(=O)NO)C(C)C)S(=O)(=O)c1ccc2cc(O)ccc2c1]

To a solution of N-isoamyl-N-(6-hydroxy naphthalene-2-sulfonyl)-D-valine O-trityl hydroxamic acid (0.21 g, 0.32 mmol) in dichloromethane (10 mL) is added trifluoroacetic acid (0.199 mL, 2.58 mmol) followed by triethyl silane (0.103 mL, 0.65 mmol). The reaction is allowed to stir at ambient temperature for 30 minutes. The solvent is removed in vacuo, and the residue is purified by column chromatography (15% hexanes-ethyl acetate), followed by crystallization from hexane-dichloromethane to afford the title compound as a white powder (0.04 g, 30% yield). LCMS (m/z): 409.24 (M+1), 407.29 (M−1). CHN: Calc C, 62.04; H, 7.44; N, 6.89. Found C, 61.88; H, 7.38; N, 6.79.

Example 32

2-[(6-Amino-naphthalene-2-sulfonyl)-(3-phenyl-propyl)-amino]-N-hydroxy-3-methyl-butyramide

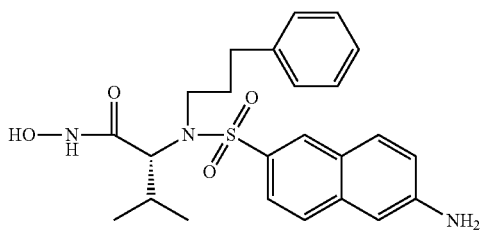 [SMILES: CC(C)[C@H](C(=O)NO)N(CCCc1ccccc1)S(=O)(=O)c1ccc2cc(N)ccc2c1]

Following methods C and K, the title compound is prepared from (R)-2-amino-3-methyl-butyric acid tert-butyl ester, 7-acetylamino-naphthalene-2-sulfonyl chloride, chloroethane and (3-bromo-propyl)-benzene. LCMS (m/z): 454.27 (M−1).

Example 33

(R)-1-(Naphthalene-2-sulfonyl)-azepane-2-carboxylic acid hydroxyamide

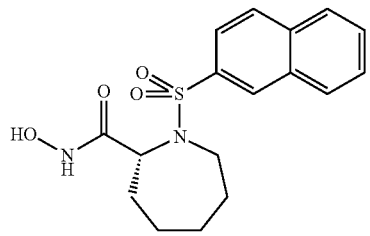

Following method H the title compound is prepared from (R)-1-(naphthalene-2-sulfonyl)-2,3,6,7-tetrahydro-1H-azepine-2-carboxylic acid hydroxyamide. LCMS (m/z): 349 (M+1). Analytics calculated for $C_{17}H_{20}N_2O_4S$: C, 58.6; H, 5.79; N, 8.04. Found: C, 60.83; H, 5.99; N, 7.45.

Example 34

2-[(6-Acetylamino-naphthalene-2-sulfonyl)-(3-phenyl-propyl)-amino]-N-hydroxy-3-methyl-butyramide

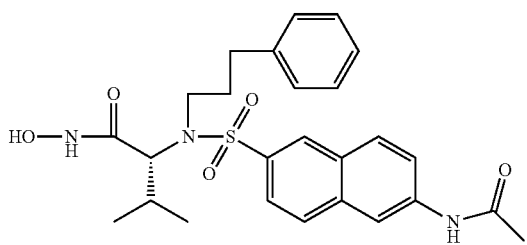 [SMILES: CC(=O)Nc1ccc2cc(S(=O)(=O)N(CCCc3ccccc3)[C@@H](C(=O)NO)C(C)C)ccc2c1]

Following methods C and K, the title compound is prepared from (R)-2-amino-3-methyl-butyric acid tert-butyl ester, 7-acetylamino-naphthalene-2-sulfonyl chloride, chloroethane and (3-bromo-propyl)-benzene. LCMS (m/z): 498.1 (M+1), 496.3 (M−1).

Example 35

N-Hydroxy-2-[(3-methyl-butyl)-(naphthalene-2-sulfonyl)-amino]-2-(tetrahydro-pyran-4-yl)-acetamide

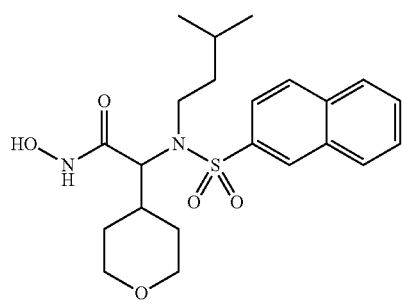 [SMILES: CC(C)CCN(C(C(=O)NO)C1CCOCC1)S(=O)(=O)c1ccc2ccccc2c1]

Following methods B and L, the title compound is prepared from amino-(tetrahydro-pyran-4-yl)-acetic acid, naphthalene-2-sulfonyl chloride and 1-bromo-3-methyl-butane. LCMS (m/z): 435.4 (M+1), 433.5 (M−1) (HPLC-MS).

Example 36

N-isoamyl-N-(6-methoxy naphthalene-2-sulfonyl)-D-valine hydroxamic acid

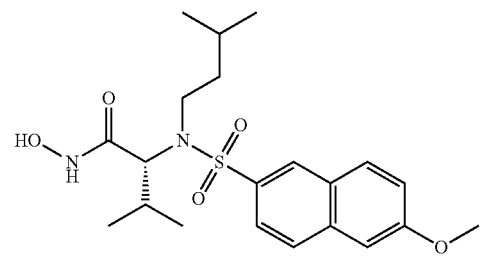 [SMILES: COc1ccc2cc(S(=O)(=O)N(CCC(C)C)[C@@H](C(=O)NO)C(C)C)ccc2c1]

Following methods A and L, the title compound is prepared from (R)-2-amino-3-methyl-butyric acid tert-butyl ester, 6-methoxy-naphthalene-2-sulfonyl chloride and 1-bromo-3-methyl-butane. LCMS (m/z): 421.36 (M−1).

Example 37

N-isoamyl-N-(6-hydroxy naphthalene-2-sulfonyl)-D-valine hydroxamic acid

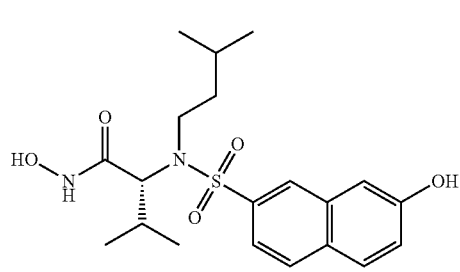 [SMILES: CC(C)CCN([C@@H](C(=O)NO)C(C)C)S(=O)(=O)c1ccc2ccc(O)cc2c1]

Following methods A and L, the title compound is prepared from (R)-2-amino-3-methyl-butyric acid tert-butyl ester, 6-hydroxy-naphthalene-2-sulfonyl chloride and 1-bromo-3-methyl-butane. LCMS (m/z): 409.24 (M+1), 407.29 (M−1). CHN Calc C, 62.04; H, 7.44; N, 6.89. Found C, 61.88; H, 7.38; N, 6.79.

Example 38

2-[(7-Amino-naphthalene-2-sulfonyl)-(3-phenyl-propyl)-amino]-N-hydroxy-3-methyl-butyramide

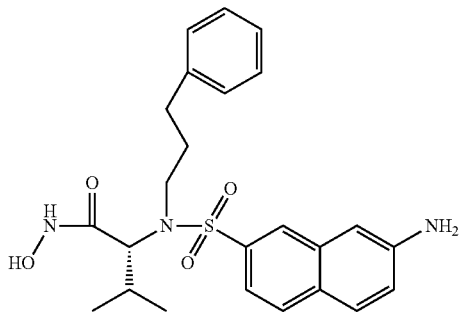 [SMILES: CC(C)[C@H](C(=O)NO)N(CCCc1ccccc1)S(=O)(=O)c1ccc2ccc(N)cc2c1]

Following methods C and K, the title compound is prepared from (R)-2-amino-3-methyl-butyric acid tert-butyl ester, 7-acetylamino-naphthalene-2-sulfonyl chloride and (3-bromo-propyl)-benzene. LCMS (m/z): 456.3 (M+1), 454.4 (M−1).

Example 39

(R)-1-(Naphthalene-2-sulfonyl)-5-phenyl-1,2,3,6-tetrahydro-pyridine-2-carboxylic acid hydroxyamide

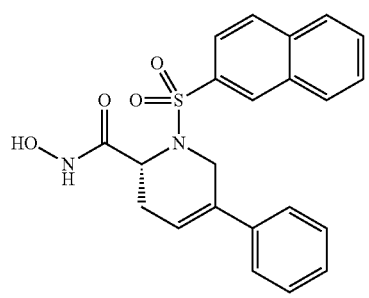 [SMILES: O=C(NO)[C@H]1CC=C(c2ccccc2)CN1S(=O)(=O)c1ccc2ccccc2c1]

Following methods B, F, G and L, the title compound is prepared from (R)-2-amino-pent-4-enoic acid ethyl ester, naphthalene-2-sulfonyl chloride and 2-hydroxyacetophenone. LCMS (m/z): 409 (M+1). Analytics calculated for $C_{14}H_{13}N_2O_4S_2$: C, 66.10; H, 4.93; N, 6.86. Found: C, 66.10; H, 4.94; N, 6.59.

Example 40

(R)—N-Hydroxy-2-[(7-methoxy-naphthalene-2-sulfonyl)-(3-methyl-butyl)-amino]-3-methyl-butyramide

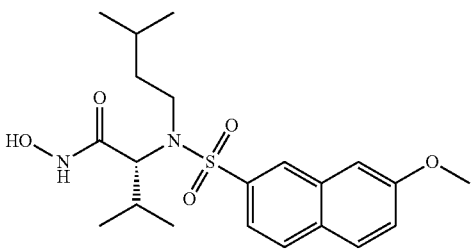 [SMILES: COc1ccc2ccc(S(=O)(=O)N(CCC(C)C)[C@@H](C(=O)NO)C(C)C)cc2c1]

Following methods A and L, the title compound is prepared from (R)-2-amino-3-methyl-butyric acid tert-butyl ester, 7-methoxy-naphthalene-2-sulfonyl chloride and 1-bromo-3-methyl-butane. Analytical data: LCMS (m/z): 423 (M+1).

Example 41

N-(2-(4-fluorophenoxy)ethyl)-N-(naphthalene-2-sulfonyl)-D-valine hydroxamic acid

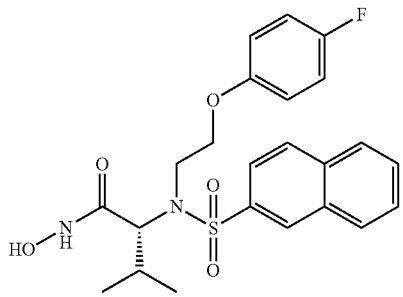 [SMILES: CC(C)[C@H](C(=O)NO)N(CCOc1ccc(F)cc1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and 1-(2-bromo-ethoxy)-4-fluoro-benzene. LCMS (m/z): 461.25 (M+1), 459.33 (M−1).

Example 42

2-[(6-Ethoxy-naphthalene-2-sulfonyl)-(3-methyl-butyl)-amino]-N-hydroxy-3-methyl-butyramide

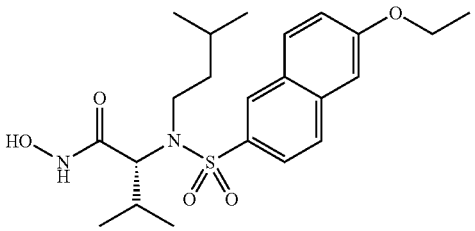 [SMILES: CCOc1ccc2cc(S(=O)(=O)N(CCC(C)C)[C@@H](C(=O)NO)C(C)C)ccc2c1]

Following methods A, E and L, the title compound is prepared from (R)-2-amino-3-methyl-butyric acid tert-butyl ester, 6-hydroxy-naphthalene-2-sulfonyl chloride, iodoethane and 1-bromo-3-methyl-butane. LCMS (m/z): 435.34 (M−1).

Example 43

2-[Benzyl-(6-p-tolylamino-naphthalene-2-sulfonyl)-amino]-N-hydroxy-3-methyl-butyramide

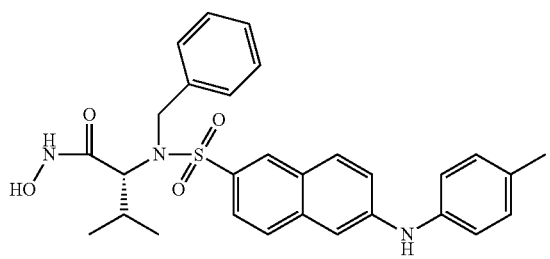 [SMILES: Cc1ccc(Nc2ccc3cc(S(=O)(=O)N(Cc4ccccc4)[C@@H](C(=O)NO)C(C)C)ccc3c2)cc1]

Following methods C and K, the title compound is prepared from (R)-2-amino-3-methyl-butyric acid tert-butyl ester, 6-p-tolylamino-naphthalene-2-sulfonyl chloride and benzyl bromide. LCMS (m/z): 518.2 (M+1), 516.4 (M−1).

Example 44

(R)-1-(Naphthalene-2-sulfonyl)-4-vinyl-1,2,3,6-tetrahydro-pyridine-2-carboxylic acid hydroxyamide

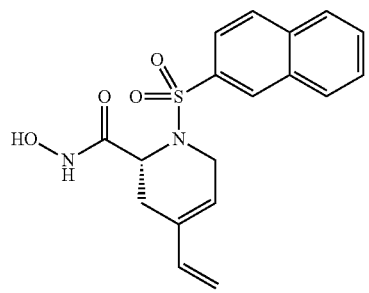 [SMILES: C=CC1=CCN(S(=O)(=O)c2ccc3ccccc3c2)[C@@H](C(=O)NO)C1]

Following methods B, G and L, the title compound is prepared from (R)-2-amino-pent-4-ynoic acid ethyl ester, naphthalene-2-sulfonyl chloride and 3-bromo-propene. LCMS (m/z): 359 (M+1). Analytics calculated for $C_{18}H_{18}N_2O_4S$: C, 60.32; H, 5.06; N, 17.86. Found: C, 59.99; H, 5.31; N, 7.82.

Example 45

N-Hydroxy-3-methyl-2-[(naphthalene-2-sulfonyl)-pyridin-3-ylmethyl-amino]-butyramide

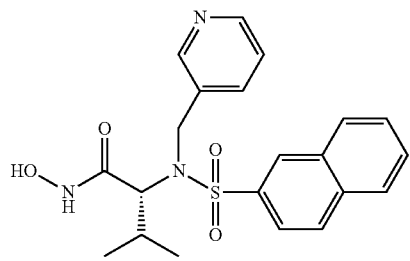 [SMILES: CC(C)[C@H](C(=O)NO)N(Cc1cccnc1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and 3-chloromethyl-pyridine. LCMS (m/z): 414.2 (M+1), 412.2 (M−1)

Example 46

(R)—N-Hydroxy-2-[[2-(3-methoxy-phenoxy)-ethyl]-(naphthalene-2-sulfonyl)-amino]-3-methyl-butyramide

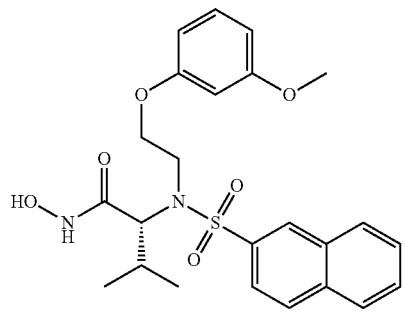 [SMILES: COc1cccc(OCCN([C@@H](C(=O)NO)C(C)C)S(=O)(=O)c2ccc3ccccc3c2)c1]

Following methods A and L, the title compound is prepared from (R)-2-amino-3-methyl-butyric acid tert-butyl ester, naphthalene-2-sulfonyl chloride and 1-(2-bromo-ethoxy)-3-methoxy-benzene. Analytical data: LCMS (m/z): 473 (M+1).

Example 47

N-Hydroxy-3-methyl-2-[[6-(3-methyl-butoxy)-naphthalene-2-sulfonyl]-(3-methyl-butyl)-amino]-butyramide

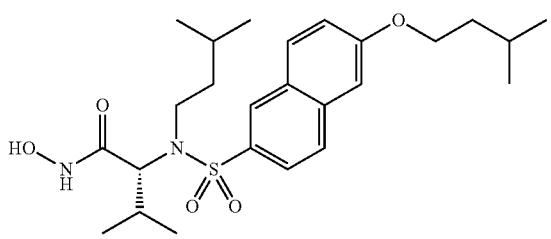 [SMILES: CC(C)CCOc1ccc2cc(S(=O)(=O)N(CCC(C)C)[C@@H](C(=O)NO)C(C)C)ccc2c1]

Following methods A, E and L, the title compound is prepared from (R)-2-amino-3-methyl-butyric acid tert-butyl ester, 6-hydroxy-naphthalene-2-sulfonyl chloride and 1-bromo-3-methyl-butane. LCMS (m/z): 477.36 (M−1).

Example 48

2-[(7-Ethoxy-naphthalene-2-sulfonyl)-(3-methyl-butyl)-amino]-N-hydroxy-3-methyl-butyramide

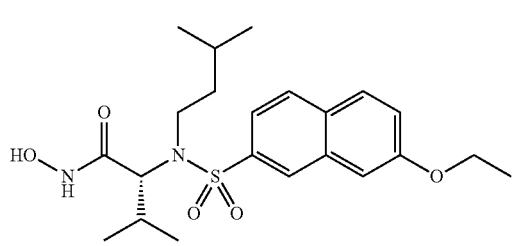 [SMILES: CCOc1ccc2ccc(S(=O)(=O)N(CCC(C)C)[C@@H](C(=O)NO)C(C)C)cc2c1]

Following methods A, E and L, the title compound is prepared from (R)-2-amino-3-methyl-butyric acid tert-butyl ester, 7-hydroxy-naphthalene-2-sulfonyl chloride, iodoethane and 1-bromo-3-methyl-butane. LCMS (m/z): 435.32 (M−1).

Example 49

N-Hydroxy-2-[(6-isobutoxy-naphthalene-2-sulfonyl)-(3-methyl-butyl)-amino]-3-methyl-butyramide

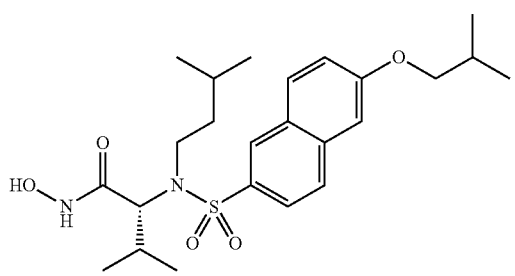 [SMILES: CC(C)CCN([C@@H](C(=O)NO)C(C)C)S(=O)(=O)c1ccc2cc(OCC(C)C)ccc2c1]

Following methods A, E and L, the title compound is prepared from (R)-2-amino-3-methyl-butyric acid tert-butyl ester, 6-hydroxy-naphthalene-2-sulfonyl chloride, 1-iodo-2-methyl-propane and 1-bromo-3-methyl-butane. LCMS (m/z): 463.43 (M−1).

Example 50

(R)-1-(Quinoline-3-sulfonyl)-piperidine-2-carboxylic acid hydroxyamide

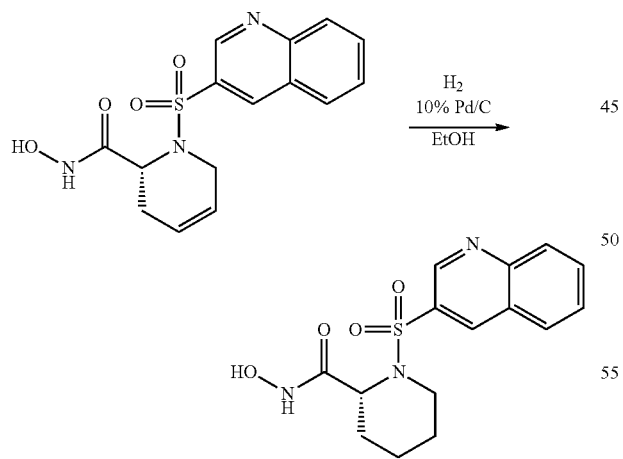

Following method H the title compound is prepare from (R)-1-(quinoline-3-sulfonyl)-1,2,3,6-tetrahydro-pyridine-2-carboxylic acid hydroxyamide. $^1$HNMR (400 MHz, DMSO): δ 1.25-1.75 (m, 5H), 1.9 (m, 1H), 3.4 (m, 1H), 3.8 (br, 1H), 4.45 (br, 1H), 7.75 (t, 1H, J=7 Hz), 7.95 (t, 1H, J=7 Hz), 8.10 (d, 1H, J=7 Hz), 8.22 (d, 1H, J=7 Hz), 8.8 (d, 1H, J=2 Hz), 9.15 (d, 1H, J=2 Hz). LCMS (m/z): 336 (M+1).

Example 51

2-[(6-Amino-naphthalene-2-sulfonyl)-(3-methyl-butyl)-amino]-N-hydroxy-3-methyl-butyramide

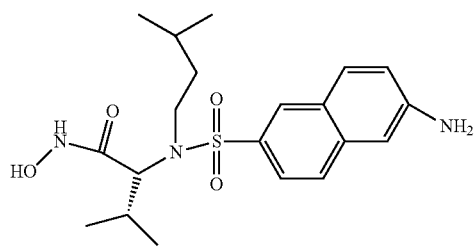

Following methods C and K, the title compound is prepared from (R)-2-amino-3-methyl-butyric acid tert-butyl ester, 6-acetylamino-naphthalene-2-sulfonyl chloride and 1-bromo-3-methyl-butane. LCMS (m/z): 408.1 (M+1), 406.2 (M−1).

Example 52

1-(Naphthalene-2-sulfonyl)-pyrrolidine-2-carboxylic acid hydroxyamide

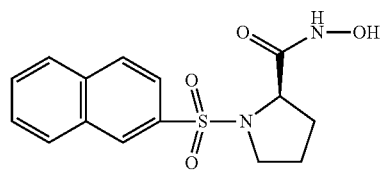 [SMILES: O=C(NO)[C@H]1CCCN1S(=O)(=O)c1ccc2ccccc2c1]

Following typical sulfonylation conditions and method L, the title compound is prepared from proline and naphthalene-2-sulfonyl chloride. LCMS (m/z): 319.18 (M−1)

Example 53

2-[(6-Benzyloxy-naphthalene-2-sulfonyl)-(3-methyl-butyl)-amino]-N-hydroxy-3-methyl-butyramide

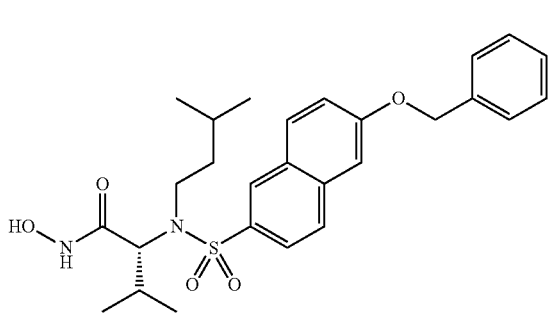 [SMILES: CC(C)CCN([C@@H](C(=O)NO)C(C)C)S(=O)(=O)c1ccc2cc(OCc3ccccc3)ccc2c1]

Following methods A, E and L, the title compound is prepared from (R)-2-amino-3-methyl-butyric acid tert-butyl ester, 6-hydroxy-naphthalene-2-sulfonyl chloride, benzyl bromide and 1-bromo-3-methyl-butane. LCMS (m/z): 497.44 (M−1).

Example 54

(R)—N-Hydroxy-3-methyl-2-[(naphthalene-2-sulfonyl)-pyridin-2-ylmethyl-amino]-butyramide

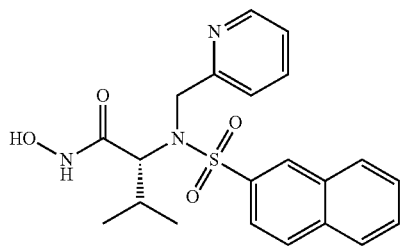 [SMILES: CC(C)[C@H](C(=O)NO)N(Cc1ccccn1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and 2-chloromethyl-pyridine. LCMS (m/z): 414 (M+1). (hydrochloric acid salt) Analytics calculated for $C_{21}H_{24}N_3O_4SCl$: C, 57.99; H, 5.33; N, 6.44. Found: C, 55.97; H, 5.51; N, 6.00.

Example 55

2-[(6-Acetylamino-naphthalene-2-sulfonyl)-(3-methyl-butyl)-amino]-N-hydroxy-3-methyl-butyramide

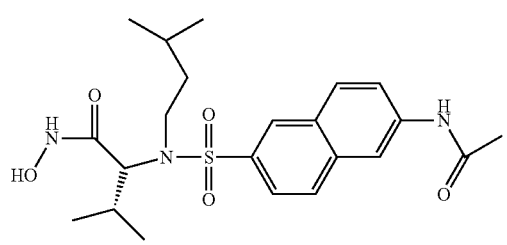

Following methods C and K, the title compound is prepared from (R)-2-amino-3-methyl-butyric acid tert-butyl ester, 6-acetylamino-naphthalene-2-sulfonyl chloride and 1-bromo-3-methyl-butane. LCMS (m/z): 450.2 (M+1), 448.3 (M−1).

Example 56

N-(2-Dimethylamino-ethyl)-N-(6-methoxy naphthalene-2-sulfonyl)-D-valine hydroxamic acid

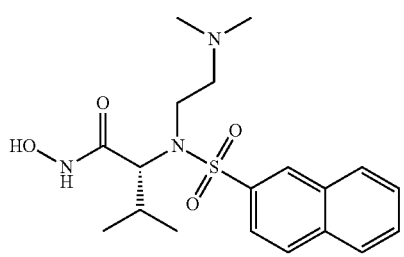 [SMILES: CC(C)[C@H](C(=O)NO)N(CCN(C)C)S(=O)(=O)c1ccc2ccccc2c1]

Following methods A and L, the title compound is prepared from (R)-2-amino-3-methyl-butyric acid tert-butyl ester, naphthalene-2-sulfonyl chloride and (2-chloro-ethyl)-dimethyl-amine. LCMS (m/z): 394.31 (M+1), 392.34 (M−1).

Example 57

N-Hydroxy-3-methyl-2-{(3-methyl-butyl)-[7-(3-methyl-butylamino)-naphthalene-2-sulfonyl]-amino}-butyramide

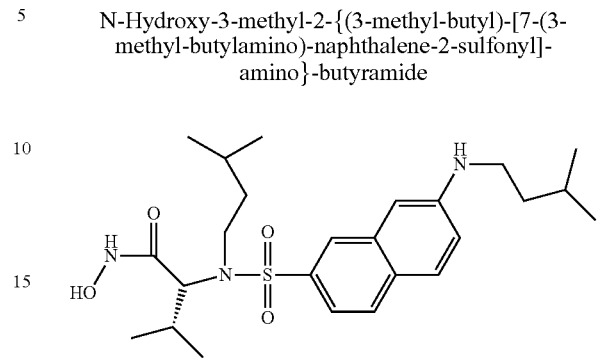

Following methods C and K, the title compound is prepared from (R)-2-amino-3-methyl-butyric acid tert-butyl ester, 7-acetylamino-naphthalene-2-sulfonyl chloride and 1-bromo-3-methyl-butane. LCMS (m/z): 478.2 (M+1), 476.3 (M−1).

Example 58

(R)-2-[[2-(4-Chloro-phenoxy)-ethyl]-(naphthalene-2-sulfonyl)-amino]-N-hydroxy-3-methyl-butyramide

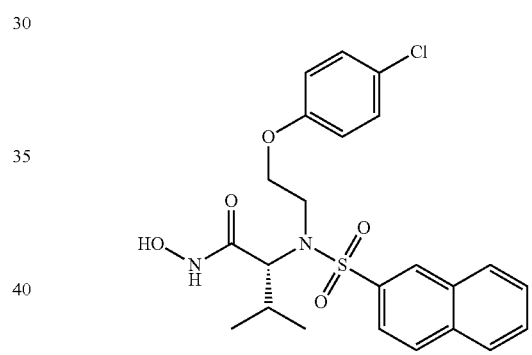

Following methods A and L, the title compound is prepared from (R)-2-amino-3-methyl-butyric acid tert-butyl ester, naphthalene-2-sulfonyl chloride and 1-(2-bromo-ethoxy)-4-chloro-benzene. Analytical data: LCMS (m/z): 477 (M+1).

Example 59

(R)-3-tert-Butoxy-N-hydroxy-2-[(3-methyl-butyl)-(naphthalene-2-sulfonyl)-amino]-propionamide

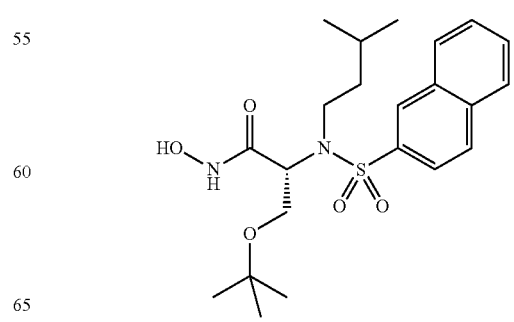

Following typical methods for sulfonylation, alkylation and method L, the title compound is prepared from (R)-2-amino-3-tert-butoxy-propionic acid methyl ester, naphthalene-2-sulfonyl chloride and 1-iodo-3-methyl-butane. ¹HNMR (400 MHz, MeOD): δ 0.88 (d, 6H, J=6 Hz), 0.95 (s, 9H), 1.45-1.65 (m, 4H), 2.02-2.38 (m, 4H), 3.30-3.43 (m, 1H), 3.5-3.75 (m, 2H), 4.42 (t, 1H, J=7 Hz), 7.60-7.70 (m, 2H), 7.85 (dd, 1H, J=2 Hz, J=7 Hz), 7.97-8.05 (m, 3H), 8.45 (s, 1H). LCMS (m/z): 437 (M+1). Analytics calculated for $C_{22}H_{32}N_2O_5S$: C, 60.53; H, 7.39; N, 6.42. Found: C, 60.19; H, 7.02; N, 6.28.

Example 60

(R)-5-Methyl-1-(naphthalene-2-sulfonyl)-1,2,3,6-tetrahydro-pyridine-2-carboxylic acid hydroxyamide

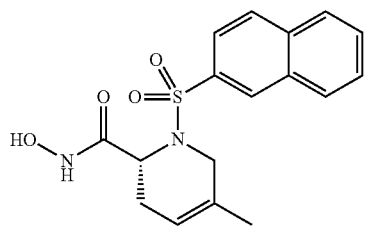 [SMILES: CC1=CC[C@H](C(=O)NO)N(S(=O)(=O)c2ccc3ccccc3c2)C1]

Following methods B, F, G and L, the title compound is prepared from (R)-2-amino-pent-4-enoic acid ethyl ester, naphthalene-2-sulfonyl chloride and 1-hydroxy-propan-2-one. LCMS (m/z): 345.2 (M−1). Analytics calculated for $C_{17}H_{18}N_2O_4S$: C, 58.94; H, 5.24; N, 8.09. Found: C, 58.51; H, 5.34; N, 7.68.

Example 61

2-[(7-Acetylamino-naphthalene-2-sulfonyl)-(3-methyl-butyl)-amino]-N-hydroxy-3-methyl-butyramide

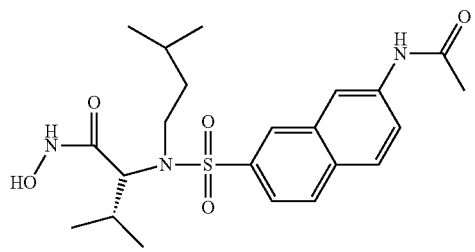

Following methods C and K, the title compound is prepared from (R)-2-amino-3-methyl-butyric acid tert-butyl ester, 7-acetylamino-naphthalene-2-sulfonyl chloride and 1-bromo-3-methyl-butane. LCMS (m/z): 450.4 (M+1), 448.5 (M−1).

Example 62

N-(2-(3-chlorophenoxy)ethyl)-N-(naphthalene-2-sulfonyl)-D-valine hydroxamic acid

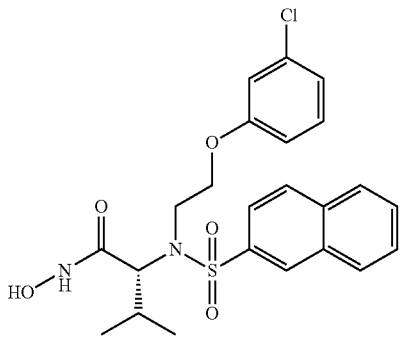 [SMILES: CC(C)[C@H](C(=O)NO)N(CCOc1cccc(Cl)c1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and 1-(2-bromo-ethoxy)-3-chloro-benzene. LCMS (m/z): 477.29 (M+1), 475.35 (M−1).

Example 63

(R)-1-(Quinoline-6-sulfonyl)-1,2,3,6-tetrahydro-pyridine-2-carboxylic acid hydroxyamide

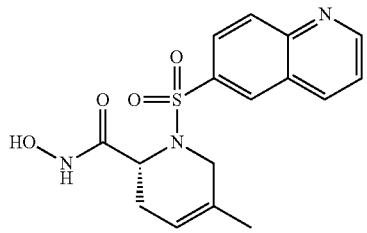 [SMILES: CC1=CC[C@H](C(=O)NO)N(S(=O)(=O)c2ccc3ncccc3c2)C1]

Following methods B, G and L, the title compound is prepared from (R)-2-amino-pent-4-enoic acid ethyl ester, quinoline-6-sulfonyl chloride and 3-bromo-propene. ¹HNMR (400 MHz, MeOD): δ 2.15-2.45 (m, 4H), 3.95-4.25 (m, 4H), 5.79 (d, 2H, J=7 Hz), 5.65 (br, 2H), 7.67 (q, 1H, J=4 Hz), 8.15 (m, 2H), 8.55 (br, 2H), 8.98 (m, 1H). LCMS (m/z): 334 (M+1).

Example 64

N-(2-(2-chlorophenoxy)ethyl)-N-(naphthalene-2-sulfonyl)-D-valine hydroxamic acid

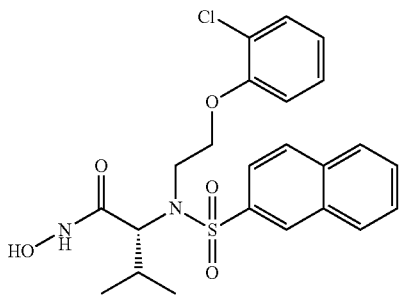 [SMILES: CC(C)[C@H](C(=O)NO)N(CCOc1ccccc1Cl)S(=O)(=O)c1ccc2ccccc2c1]

Following methods A and L, the title compound is prepared from (R)-2-amino-3-methyl-butyric acid tert-butyl ester, naphthalene-2-sulfonyl chloride and 1-(2-bromo-ethoxy)-2-chloro-benzene. LCMS (m/z): 477.22 (M+1), 475.30 (M−1).

Example 65

N-Hydroxy-2-methyl-2-[(3-methyl-butyl)-(naphthalene-2-sulfonyl)-amino]-propionamide

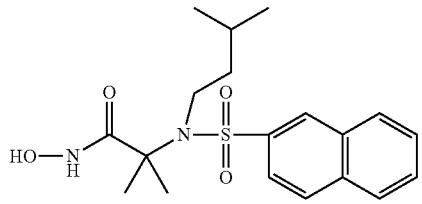 [SMILES: CC(C)CCN(C(C)(C)C(=O)NO)S(=O)(=O)c1ccc2ccccc2c1]

Following methods B and L, the title compound is prepared from 2-amino-2-methyl-propionic acid, naphthalene-2-sulfonyl chloride and 1-bromo-3-methyl-butane. LCMS (m/z): 377.29 (M−1).

Example 66

2-[(6-Allyloxy-naphthalene-2-sulfonyl)-(3-methyl-butyl)-amino]-N-hydroxy-3-methyl-butyramide

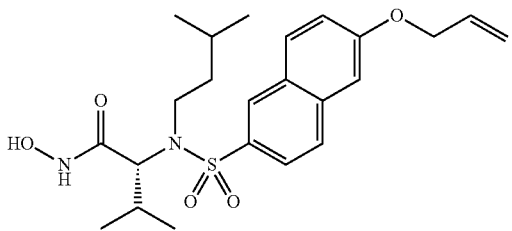 [SMILES: C=CCOc1ccc2cc(S(=O)(=O)N(CCC(C)C)[C@@H](C(=O)NO)C(C)C)ccc2c1]

Following methods A, E and L, the title compound is prepared from (R)-2-amino-3-methyl-butyric acid tert-butyl ester, 6-hydroxy-naphthalene-2-sulfonyl chloride, 3-bromo-propene and 1-bromo-3-methyl-butane. LCMS (m/z): 447.31 (M−1).

Example 67

(R)—N-Hydroxy-3-methyl-2-[(3-methyl-butyl)-(quinoline-6-sulfonyl)-amino]-butyramide

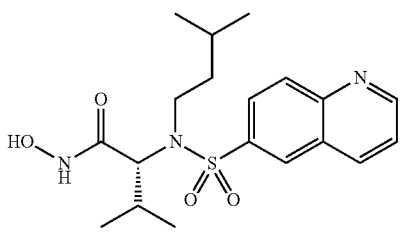 [SMILES: CC(C)CCN([C@@H](C(=O)NO)C(C)C)S(=O)(=O)c1ccc2ncccc2c1]

Following methods A and L, the title compound is prepared from (R)-2-amino-3-methyl-butyric acid tert-butyl ester, quinoline-6-sulfonyl chloride and 1-iodo-3-methyl-butane. $^1$HNMR (400 MHz, MeOD): δ 0.85-0.98 (m, 12H), 1.4-1.6 (m, 2H), 1.75-1.85 (m, 1H), 2.1-2.3 (m, 1H), 3.2-3.25 (m, 1H), 3.8-3.9 (m, 2H), 7.82 (q, 1H, J=4.5 Hz), 8.62 (s, 1H), 8.75 (d, 1H, J=8 Hz), 9.10 (d, 1H, J=4.5 Hz). LCMS (m/z): 394 (M+1).

Example 68

2-[(7-Ethoxy-naphthalene-2-sulfonyl)-pyridin-3-ylmethyl-amino]-N-hydroxy-3-methyl-butyramide

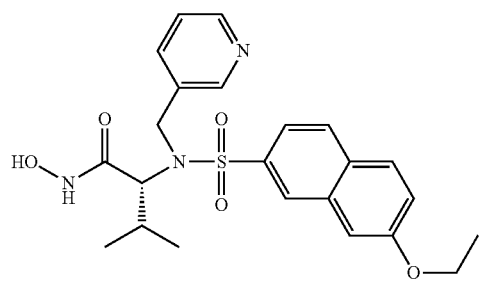 [SMILES: CCOc1ccc2ccc(S(=O)(=O)N(Cc3cccnc3)[C@@H](C(=O)NO)C(C)C)cc2c1]

Following methods A, E and J, the title compound is prepared from (R)-2-amino-3-methyl-butyric acid tert-butyl ester, 7-hydroxy-naphthalene-2-sulfonyl chloride, chloroethane and 3-chloromethyl-pyridine. LCMS (m/z): 458.3 (M+1), 456.3 (M−1). CHN Calc C, 60.38; H, 5.95; N, 9.18. Found C, 60.48; H, 5.97; N, 9.08.

Example 69

(R)—N-Hydroxy-3,3-dimethyl-2-[(3-methyl-butyl)-(naphthalene-2-sulfonyl)-amino]-butyramide

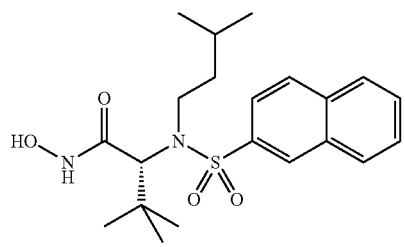 [SMILES: CC(C)CCN([C@@H](C(=O)NO)C(C)(C)C)S(=O)(=O)c1ccc2ccccc2c1]

Following methods B and L, the title compound is prepared from (R)-2-amino-3,3-dimethyl-butyric acid, naphthalene-2-sulfonyl chloride and 1-iodo-3-methyl-butane. 1HNMR (400 MHz, MeOD): δ 0.88 (q, 6H, J=4 Hz), 1.10 (s, 9H), 1.4-1.6 (m, 4H), 1.9 (m, 1H), 3.15-3.25 (m, 1H), 4.05 (s, 1H), 7.6-7.7 (m, 2H), 7.8-7.85 (m, 1H), 7.92-8.08 (m, 3H), 8.45 (s, 1H). LCMS (m/z): 405 (M−1). Analytics calculated for $C_{21}H_{30}N_2O_4S$: C, 62.04; H, 7.44; N, 6.89. Found: C, 61.70; H, 7.27; N, 6.67.

Example 70

1-[(3-Methyl-butyl)-(naphthalene-2-sulfonyl)-amino]-cyclopentanecarboxylic acid hydroxyamide

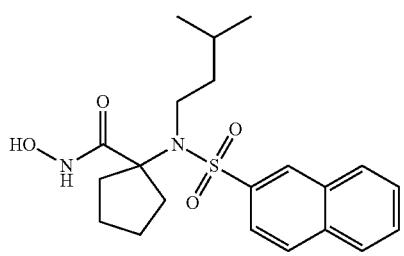 [SMILES: CC(C)CCN(C1(C(=O)NO)CCCC1)S(=O)(=O)c1ccc2ccccc2c1]

Following methods B and L, the title compound is prepared from 1-amino-cyclopentanecarboxylic acid, naphthalene-2-sulfonyl chloride and 1-bromo-3-methyl-butane. LCMS (m/z): 405.24 (M+1), 403.30 (M−1). CHN Calc C, 62.35; H, 6.98; N, 6.92. Found C, 62.27; H, 6.85; N, 6.55.

Example 71

2-[{7-[Acetyl-(3-methyl-butyl)-amino]-naphthalene-2-sulfonyl}-(3-methyl-butyl)-amino]-N-hydroxy-3-methyl-butyramide

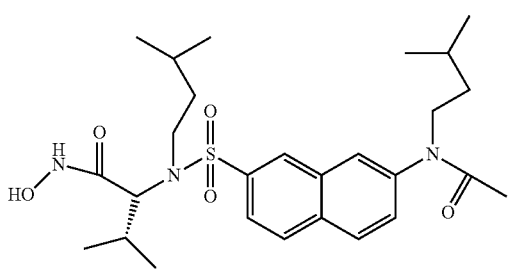

Following methods C and K, the title compound is prepared from (R)-2-amino-3-methyl-butyric acid tert-butyl ester, 7-acetylamino-naphthalene-2-sulfonyl chloride and 1-bromo-3-methyl-butane. LCMS (m/z): 520.2 (M+1), 518.3 (M−1).

Example 72

(R)-1-(Quinoline-3-sulfonyl)-1,2,3,6-tetrahydro-pyridine-2-carboxylic acid hydroxyamide

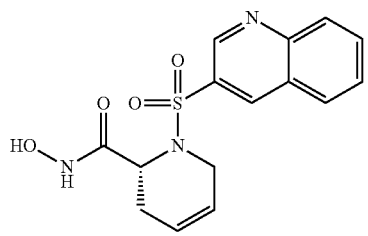 [SMILES: O=C(NO)[C@H]1CC=CCN1S(=O)(=O)c1cnc2ccccc2c1]

Following methods B, G and L, the title compound is prepared from (R)-2-amino-pent-4-enoic acid ethyl ester, quinoline-3-sulfonyl chloride and 3-bromo-propene. $^1$HNMR (400 MHz, DMSO): δ 2.20 (br, 2H), 3.85-4.15 (m, 2H), 4.70 (m, 1H), 5.65 (br, 2H), 7.77 (t, 1H, J=7 Hz), 7.95 (t, 1H, J=7 Hz), 8.1 (d, 1H, J=8 Hz), 8.23 (d, 1H, J=8 Hz), 8.9 (d, 1H, J=2 Hz), 9.1 (d, 1H, J=2 Hz). LCMS (m/z): 334 (M+1).

Example 73

1-[(3-Methyl-butyl)-(naphthalene-2-sulfonyl)-amino]-cyclopropanecarboxylic acid hydroxyamide

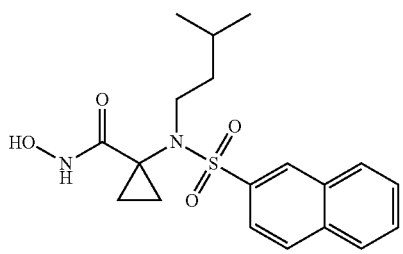 [SMILES: CC(C)CCN(C1(C(=O)NO)CC1)S(=O)(=O)c1ccc2ccccc2c1]

Following methods B and L, the title compound is prepared from 1-amino-cyclopropanecarboxylic acid, naphthalene-2-sulfonyl chloride and 1-bromo-3-methyl-butane. LCMS (m/z): 377.06 (M+1), 375.05 (M−1). CHN Calc C, 60.62; H, 6.43; N, 7.44. Found C, 60.40; H, 6.06; N, 7.31.

Example 74

4-[Hydroxycarbamoyl-(naphthalene-2-sulfonylamino)-methyl]-piperidine-1-carboxylic acid tert-butyl ester

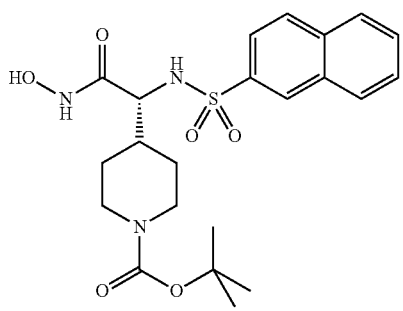 [SMILES: CC(C)(C)OC(=O)N1CCC([C@@H](NS(=O)(=O)c2ccc3ccccc3c2)C(=O)NO)CC1]

Following typical sulfonylation conditions and method L, the title compound is prepared from 4-((R)-amino-carboxymethyl)-piperidine-1-carboxylic acid tert-butyl ester and naphthalene-2-sulfonyl chloride. LCMS (m/z): 464.3 (M+1), 462.5 (M−1), CHN: Calc C, 57.00; H, 6.31; N, 9.06. Found C, 57.40; H, 6.32; N, 8.53.

Example 75

N-(2-(2,3,6-trimethyl phenoxy)ethyl)-N-(naphthalene-2-sulfonyl)-D-valine hydroxamic acid

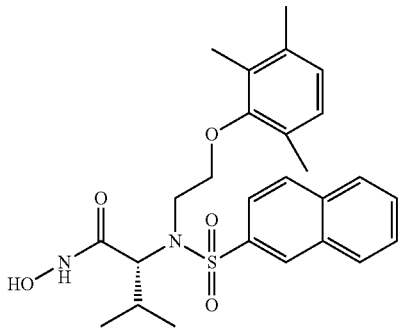 [SMILES: Cc1ccc(C)c(OCCN([C@@H](C(=O)NO)C(C)C)S(=O)(=O)c2ccc3ccccc3c2)c1C]

Following methods A and L, the title compound is prepared from (R)-2-amino-3-methyl-butyric acid tert-butyl ester, naphthalene-2-sulfonyl chloride and 2-(2-bromo-ethoxy)-1,3,4-trimethyl-benzene. LCMS (m/z): 485.35 (M+1), 483.38 (M−1).

Example 76

(R)—N-Hydroxy-3-methyl-2-[(3-methyl-butyl)-(quinoline-3-sulfonyl)-amino]-butyramide

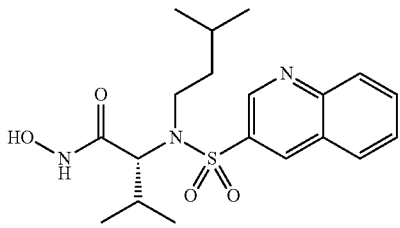 [SMILES: CC(C)CCN([C@@H](C(=O)NO)C(C)C)S(=O)(=O)c1cnc2ccccc2c1]

Following methods A and L, the title compound is prepared from (R)-2-amino-3-methyl-butyric acid tert-butyl ester, quinoline-3-sulfonyl chloride and 1-iodo-3-methyl-butane. $^1$HNMR (400 MHz, MeOD): δ 0.80-0.90 (m, 12H), 1.3-1.7 (m, 3H), 2.05-2.15 (m, 1H), 3.15 (m, 1H), 3.80 (d, 2H, J=9 Hz), 3.8-3.9 (m, 2H), 7.80 (t, 1H, J=7 Hz), 7.98 (t, 1H, J=7 Hz), 8.10 (d, 1H, J=7 Hz), 8.12 (d, 1H, J=7 Hz), 8.90 (d, 1H, J=10 Hz), 9.2 (d, 1H, J=2 Hz). LCMS (m/z): 394 (M+1). Analytics calculated for $C_{19}H_{27}N_3O_4S$: C, 57.99; H, 6.92; N, 10.68. Found: C, 58.09; H, 6.65; N, 10.51.

Example 77

N-Hydroxy-3-methyl-2-[(2-morpholin-4-yl-ethyl)-(naphthalene-2-sulfonyl)-amino]-butyramide

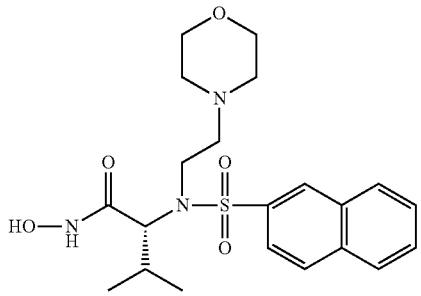 [SMILES: CC(C)[C@H](C(=O)NO)N(CCN1CCOCC1)S(=O)(=O)c1ccc2ccccc2c1]

Following methods A and L, the title compound is prepared from (R)-2-amino-3-methyl-butyric acid tert-butyl ester, naphthalene-2-sulfonyl chloride and 4-(2-chloro-ethyl)-morpholine. LCMS (m/z): 434.54 (M−1).

Example 78

(R)-1-(1-Methoxy-naphthalene-2-sulfonyl)-1,2,3,6-tetrahydro-pyridine-2-carboxylic acid hydroxyamide

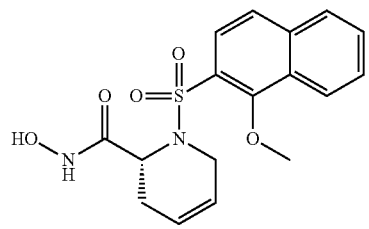 [SMILES: COc1c(S(=O)(=O)N2CC=CC[C@@H]2C(=O)NO)ccc2ccccc12]

Following methods B, G and L, the title compound is prepared from (R)-2-amino-pent-4-enoic acid ethyl ester, 1-methoxy-naphthalene-2-sulfonyl chloride and 3-bromopropene. $^1$HNMR (400 MHz, DMSO): δ 2.20 (br, 2H), 3.95 (m, 1H), 4.05 (m, 1H), 4.60 (d, 1H, J=6 Hz), 5.60 (br, 2H), 7.65-7.75 (m, 2H), 7.80 (m, 2H), 8.05 (m, 1H), 8.15 (d, 1H, J=5.5 Hz), 8.8 (s, 1H). LCMS (m/z): 363 (M+1). Analytics calculated for $C_{17}H_{18}N_2O_5S$: C, 56.34; H, 5.01; N, 7.73. Found: C, 55.87; H, 4.99; N, 7.30.

Example 79

(R)—N-Hydroxy-2-[(1-methoxy-naphthalene-2-sulfonyl)-(3-methyl-butyl)-amino]-3-methyl-butyramide

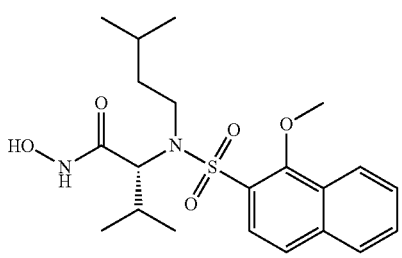 [SMILES: COc1c(S(=O)(=O)N(CCC(C)C)[C@@H](C(=O)NO)C(C)C)ccc2ccccc12]

Following methods A and L, the title compound is prepared from (R)-2-amino-3-methyl-butyric acid tert-butyl ester, 1-methoxy-naphthalene-2-sulfonyl chloride and 1-bromo-3-methyl-butane. Analytical data: LCMS (m/z): 423 (M+1).

Example 80

2-[(1-Chloro-naphthalene-2-sulfonyl)-(3-methyl-butyl)-amino]-N-hydroxy-3-methyl-butyramide

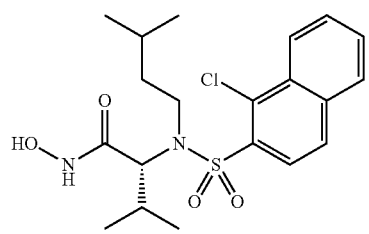 [SMILES: CC(C)CCN([C@@H](C(=O)NO)C(C)C)S(=O)(=O)c1ccc2ccccc2c1Cl]

Following methods A and L, the title compound is prepared from (R)-2-amino-3-methyl-butyric acid tert-butyl ester, 1-chloro-naphthalene-2-sulfonyl chloride and 1-bromo-3-methyl-butane. LCMS (m/z): 427 (M+1), 425 (M−1), CHN: Calc C, 56.26; H, 6.37; N, 6.56. Found C, 55.92; H, 6.44; N, 6.29.

Example 81

N-Hydroxy-2-(naphthalene-2-sulfonylamino)-acetamide

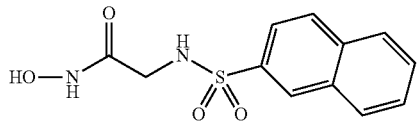 [SMILES: O=C(CNS(=O)(=O)c1ccc2ccccc2c1)NO]

Following typical sulfonylation methods and method L, the title compound is prepared from amino-acetic acid and naphthalene-2-sulfonyl chloride. LCMS (m/z): 281.0 (M+1).

Example 82

4-{Hydroxycarbamoyl-[(3-methyl-butyl)-(naphthalene-2-sulfonyl)-amino]-methyl}-piperidine-1-carboxylic acid tert-butyl ester

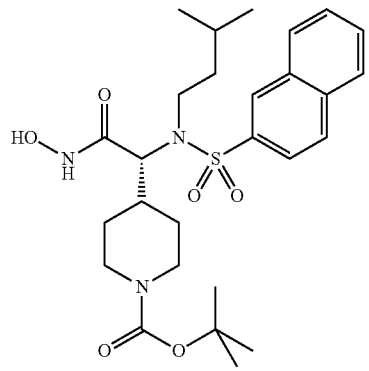 [SMILES: CC(C)CCN([C@@H](C(=O)NO)C1CCN(C(=O)OC(C)(C)C)CC1)S(=O)(=O)c1ccc2ccccc2c1]

Following methods A and L, the title compound is prepared from 4-((R)-amino-carboxy-methyl)-piperidine-1-carboxylic acid tert-butyl ester, naphthalene-2-sulfonyl chloride and 1-bromo-3-methyl-butane. LCMS (m/z): 534.2 (M+1), 532.4 (M−1), CHN: Calc C, 60.77; H, 7.37; N, 7.87. Found C, 59.76; H, 7.43; N, 7.74.

Example 83

7-(Naphthalene-2-sulfonyl)-7-aza-bicyclo[4.2.1]nonane-8-carboxylic acid hydroxyamide

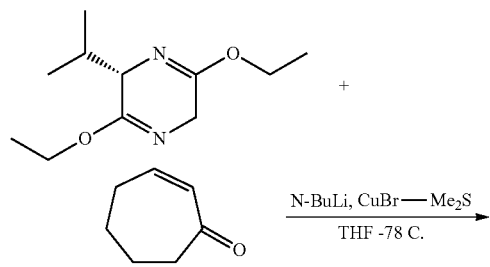

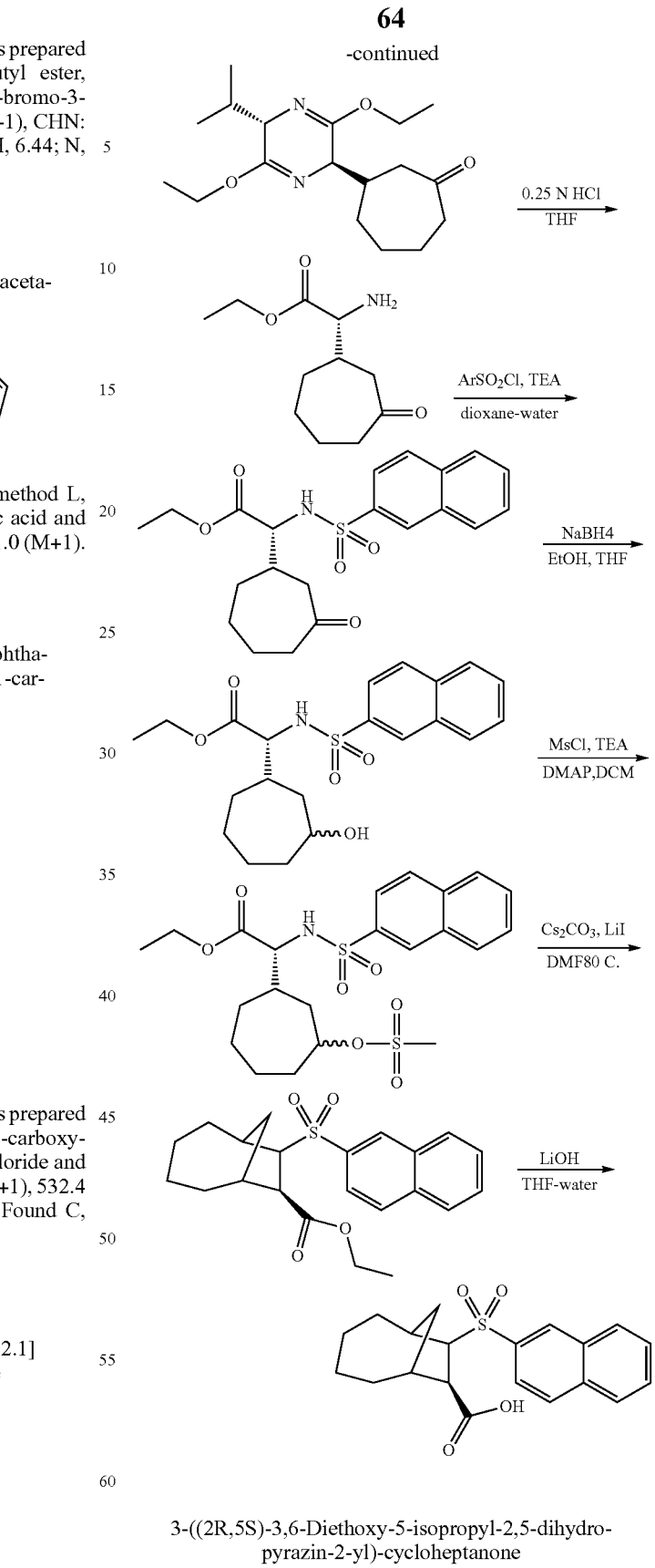

3-((2R,5S)-3,6-Diethoxy-5-isopropyl-2,5-dihydropyrazin-2-yl)-cycloheptanone

A solution of (S)-3,6-diethoxy-2-isopropyl-2,5-dihydropyrazine (6.0 g, 28.3 mmol) in tetrahydrofuran (58 mL) is cooled to −78° C. n-butyllithium (1.6 M in hexane, 21.4 mL, 34.2 mmol) is added slowly via syringe, and the reaction is allowed to stir at −78° C. for 30 minutes. The reaction mixture is then transferred via canula to a solution of CuBr-Me$_2$S (3.35 g, 16.3 mmol) in tetrahydrofuran:dimethylsulfide (90 mL, [2:1]) at −50° C. The reaction is warmed to −30° C. and stirred further for 30 minutes. The reaction is then cooled to −78° C. and cyclohept-2-eneone (5.23 mL, 46.9 mmol) is added dropwise over 10 minutes. The reaction is maintained at −78° C. until the disappearance of the dihydropyrazine is confirmed by TLC and quenched by the addition of a saturated aqueous solution of ammonium chloride at −78° C. The reaction is allowed to warm to ambient temperature, diluted with water, and extracted with diethyl ether. The organic extracts were washed with ammonium chloride, dilute ammonium hydroxide, water and brine, dried over magnesium sulfate, and concentrated in vacuo. The residue is purified by column chromatography eluting with a gradient of hexane in ether (20-25%) to afford the title compound (6.52 g, 72% yield), slightly contaminated with cyclohept-2-enone. LCMS (m/z): 323.13 (M+1).

(R)—N-naphthalene-2-sulfonyl (3-oxo-cycloheptyl)glycine ethyl ester 3-((2R,5S)-3,6-Diethoxy-5-isopropyl-2,5-dihydropyrazin-2-yl)-cycloheptanone (2.0 g, 6.2 mmol) is treated with 0.25 N hydrochloric acid (25 mL), diluted with tetrahydrofuran (40 mL) and allowed to stir at ambient temperature for 1 hour. The solvents were removed in vacuo, and azeotroped with toluene three times. The residue was dissolved in dichloromethane (50 mL) and cooled to 0° C. To this solution is added triethylamine (6.73 mL, 48.3 mmol), followed by naphthalene-2-sulfonyl chloride (4.39 g, 19.4 mmol), and the reaction is allowed to warm to ambient temperature and stirred for 16 h. The reaction is then diluted with dichloromethane washed with 1 N hydrochloric acid, sodium bicarbonate solution, and brine, and dried over magnesium sulfate. The solvents are removed in vacuo, and the residue is purified by column chromatography (50% hexanes-ethyl acetate) to afford the title compound as a yellow oil (1.8 g, 72% yield). LCMS (m/z): 404.10 (M+1), 402.09 (M−1).

(R)—N-naphthalene-2-sulfonyl (3-hydroxy-cycloheptyl)glycine ethyl ester

To a solution of (R)—N-naphthalene-2-sulfonyl (3-oxocyclohepty)glycine ethyl ester (1.05 g, 2.61 mmol) in tetrahydrofuran-ethanol (20 mL, 1:1) at 0° C. is added sodium borohydride (0.147 g, 3.88 mmol) and the reaction is stirred at 0° C. for 1 hour. The reaction was quenched at 0° C. with citric acid (10% aqueous), and the solvents were removed in vacuo. The residue was dissolved in water and extracted three times with ethyl acetate. The combined organic extracts were washed with brine, dried over magnesium sulfate, and concentrated in vacuo. The residue is purified by column chromatography (50% hexanes-ethyl acetate) to afford the title compound as a white solid (0.90 g, 85% yield). LCMS (m/z): 406.14 (M+1), 404.13 (M−1).

(R)—N-naphthalene-2-sulfonyl (3-methanesulfonyloxy-cyclohepty)glycine ethyl ester To a solution of (R)—N-naphthalene-2-sulfonyl (3-hydroxy-cyclohepty)glycine ethyl ester (0.90 g, 2.22 mmol) in dichloromethane (30 mL) at 0° C. is added triethylamine (0.463 mL, 3.3 mmol), methane sulfonyl chloride (0.269 g, 2.35 mmol), 4-dimethylaminopyridine (0.015 g, 0.12 mmol), and the reaction is allowed to warm to ambient temperature and stirred for 2 hours. The reaction is diluted with dichloromethane, washed with water and brine, and dried over magnesium sulfate. The solvents are removed in vacuo, and the residue is purified by column chromatography (35% hexanes-ethyl acetate) to afford the title compound as a colorless oil (0.95 g, 88% yield). LCMS (m/z): 484.17 (M+1), 482.16 (M−1).

(R)-7-(Naphthalene-2-sulfonyl)-7-aza-bicyclo[4.2.1] nonane-8-carboxylic acid ethyl ester To a solution of (R)—N-naphthalene-2-sulfonyl (3-methanesulfonyloxy-cycloheptyl)glycine ethyl ester (0.60 g, 1.24 mmol) in N,N-dimethylformamide (5 mL) is added cesium carbonate (1.21 g, 3.71 mmol) followed by lithium iodide (0.249 g, 1.86 mmol), and the reaction is heated to 80° C. for 3 hours. The reaction is cooled to ambient temperature, diluted with water, and extracted three times with ethyl acetate. The combined organic extracts are washed with brine, dried over magnesium sulfate, and concentrated in vacuo. The crude product is purified by column chromatography (20% hexanes-ethyl acetate) to afford the title compound as a white solid (0.37 g, 77% yield). LCMS (m/z): 388.10 (M+1).

(R)-7-(Naphthalene-2-sulfonyl)-7-aza-bicyclo[4.2.1] nonane-8-carboxylic acid

To a solution of (R)-7-(naphthalene-2-sulfonyl)-7-aza-bicyclo[4.2.1]nonane-8-carboxylic acid ethyl ester (0.55 g, 1.42 mmol) in tetrahydrofuran (15 mL) is added a solution of lithium hydroxide (1.2 g, 28.6 mmol) in water (15 mL). The reaction is heated to 80° C. for 16 h, and the solvent is removed in vacuo. The residue is dissolved in water and washed with diethyl ether. The aqueous layer is then acidified with 6 N hydrochloric acid to pH less than 4 and extracted three times with ethyl acetate. The combined organic extracts are washed with brine, dried over magnesium sulfate, and concentrated to afford the title compound as a yellow solid (0.50 g, 98% yield). LCMS (m/z): 360.07 (M+1), 358.12 (M−1).

This product is then converted into a hydroxamate according to the general protocols outlined in method L. LCMS (m/z): 375.04 (M+1), 373.02 (M−1). CHN Calc C, 60.94; H, 5.92; N, 7.48. Found C, 59.97; H, 5.92; N, 7.27

Example 84

2-[(7-Amino-naphthalene-2-sulfonyl)-(3-methyl-butyl)-amino]-N-hydroxy-3-methyl-butyramide

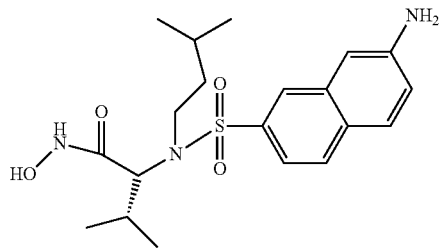

2-[(7-Acetylamino-naphthalene-2-sulfonyl)-(3-methyl-butyl)-amino]-N-hydroxy-3-methyl-butyramide (100 mg, 0.22 mmol) (example 61), 3 N hydrochloric acid (2 mL) and methanol (5 mL) are combined and stirred at reflux for 4 hours. The mixture is stirred at room for 60 hours. The solvent is partially removed in vacuo and a red precipitate forms. This precipitate is collected by filtration and air dried. LCMS (m/z): 408.2 (M+1), 406.3 (M−1).

Example 85

N-isoamyl-N-(6-methyl naphthalene-2-sulfonyl)-D-valine hydroxamic acid

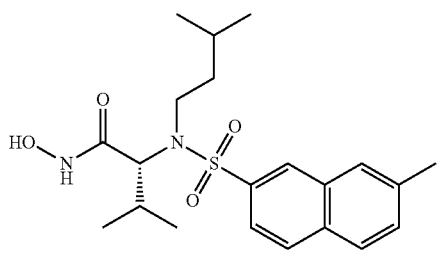 [SMILES: Cc1ccc2ccc(S(=O)(=O)N(CCC(C)C)[C@@H](C(=O)NO)C(C)C)cc2c1]

Following methods A, D and L, the title compound is prepared from (R)-2-amino-3-methyl-butyric acid tert-butyl ester, acetic acid 7-chlorosulfonyl-naphthalen-2-yl ester, tetramethyl-stannane and 1-bromo-3-methyl-butane. LCMS (m/z): 407.26 (M+1), 405.31 (M−1).

Example 86

(R)—N-Hydroxy-3-methyl-2-[[7-(3-methyl-butoxy)-naphthalene-2-sulfonyl]-(3-methyl-butyl)-amino]-butyramide

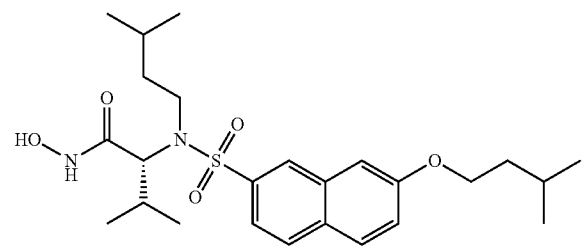 [SMILES: CC(C)CCOc1ccc2ccc(S(=O)(=O)N(CCC(C)C)[C@@H](C(=O)NO)C(C)C)cc2c1]

Following methods A and L, the title compound is prepared from (R)-2-amino-3-methyl-butyric acid tert-butyl ester, acetic acid 7-chlorosulfonyl-naphthalen-2-yl ester and 1-bromo-3-methyl-butane. Analytical data: LCMS (m/z): 479 (M+1).

Example 87

N-Hydroxy-3-methyl-2-[(3-methyl-butyl)-(6-propoxy-naphthalene-2-sulfonyl)-amino]-butyramide

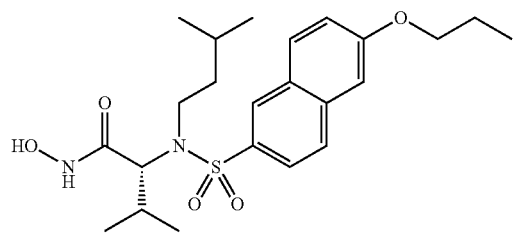 [SMILES: CCCOc1ccc2cc(S(=O)(=O)N(CCC(C)C)[C@@H](C(=O)NO)C(C)C)ccc2c1]

Following methods A, E and L, the title compound is prepared from (R)-2-amino-3-methyl-butyric acid tert-butyl ester, 6-hydroxy-naphthalene-2-sulfonyl chloride, 1-iodobutane and 1-bromo-3-methyl-butane. LCMS (m/z): 449.36 (M−1).

Example 88

(R)-1-(Naphthalene-2-sulfonyl)-2,3,6,7-tetrahydro-1H-azepine-2-carboxylic acid hydroxyamide

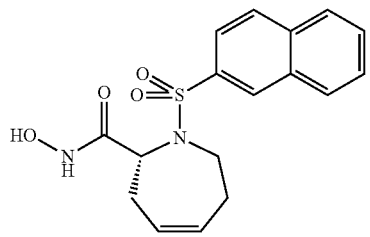 [SMILES: O=C(NO)[C@H]1CC=CCCN1S(=O)(=O)c1ccc2ccccc2c1]

Following methods B, G and L, the title compound is prepared from (R)-2-amino-pent-4-enoic acid ethyl ester, naphthalene-2-sulfonyl chloride and 4-bromo-but-1-ene. LCMS (m/z): 347 (M+1). Analytics calculated for $C_{17}H_{18}N_2O_4S$: C, 58.94; H, 5.24; N, 8.09. Found: C, 58.60; H, 5.24; N, 7.94.

Example 89

(R)-2-[Butyl-(naphthalene-2-sulfonyl)-amino]-3,N-dihydroxy-butyramide

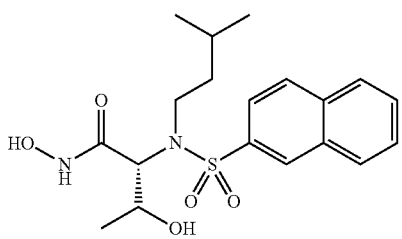 [SMILES: CC(C)CCN([C@@H](C(=O)NO)C(C)O)S(=O)(=O)c1ccc2ccccc2c1]

Following typical methods for sulfonylation, alkylation and method L, the title compound is prepared from (2R,3S)-2-amino-3-tert-butoxy-butyric acid, naphthalene-2-sulfonyl chloride and 1-iodo-3-methyl-butane. $^1$HNMR (400 MHz, DMSO): δ 0.80 (d, 6H, J=4 Hz), 1.05 (d, 3H, J=8 Hz), 1.45 (m, 1H), 1.55 (m, 2H), 3.20 (m, 1H), 3.62 (m, 1H), 3.90 (br, 1H), 4.02 (d, 1H, J=7 Hz), 4.70 (br, 1H), 7.68 (m, 2H), 7.82 (d, 1H, J=7 Hz), 8.05 (t, 2H, J=7 Hz), 8.12 (d, 1H, J=7 Hz), 8.45 (s, 1H). LCMS (m/z): 395 (M+1). Analytics calculated for $C_{19}H_{26}N_2O_5S$: C, 57.85; H, 6.64; N, 7.10. Found: C, 57.58; H, 6.74; N, 6.94.

Example 90

2,2-Dimethyl-4-(naphthalene-2-sulfonyl)-thiomorpholine-3-carboxylic acid

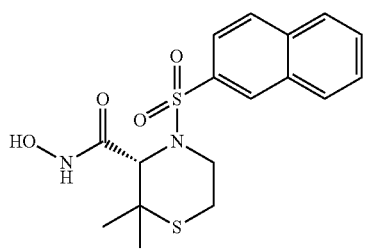 [SMILES: CC1(C)SCCN(S(=O)(=O)c2ccc3ccccc3c2)[C@H]1C(=O)NO]

Following typical sulfonylation conditions and method L, the title compound is prepared from (S)-2,2-dimethyl-thiomorpholine-3-carboxylic acid and naphthalene-2-sulfonyl chloride. LCMS (m/z): 381.2 (M+1), 379.3 (M−1), CHN: Calc CHN: 53.66, 5.30, 7.36. Found CHN: 593.51, 5.20, 7.07.

Example 91

(R)-2-(Naphthalene-2-sulfonyl)-2-aza-bicyclo[2.2.2]octane-3-carboxylic acid hydroxyamide

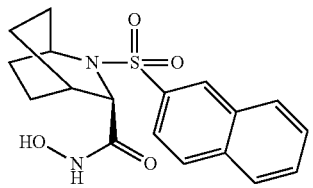 [SMILES: O=C(NO)[C@H]1C2CCC(CC2)N1S(=O)(=O)c1ccc2ccccc2c1]

Following typical methods for sulfonylation and method L, the title compound is prepared from (R)-2-aza-bicyclo[2.2.2]octane-3-carboxylic acid and naphthalene-2-sulfonyl chloride. LCMS (m/z): 361.30 (M+1), 359.36 (M−1). CHN Calc C, 59.98; H, 5.59; N, 7.77. Found C, 59.68; H, 5.49; N, 7.60.

Example 92

(R)—N-Hydroxy-3,3-dimethyl-2-(quinoline-6-sulfonylamino)-butyramide

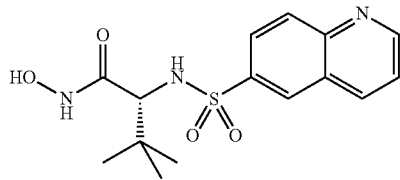 [SMILES: CC(C)(C)[C@@H](NS(=O)(=O)c1ccc2ncccc2c1)C(=O)NO]

Following typical methods for sulfonylation and method L, the title compound is prepared from (R)-2-amino-3,3-dimethyl-butyric acid and quinoline-6-sulfonyl chloride. ¹HNMR (400 MHz, MeOD): δ 0.99 (s, 9H), 3.45 (s, 1H), 7.68 (q, 1H, J=4 Hz), 8.15 (s, 2H), 8.5 (m, 2H), 9.0 (d, 1H, J=2 Hz). LCMS (m/z): 338 (M+1).

Example 93

(R)—N-Hydroxy-3,3-dimethyl-2-(naphthalene-2-sulfonylamino)-butyramide

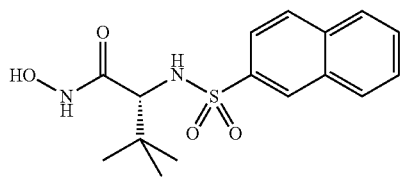 [SMILES: CC(C)(C)[C@@H](NS(=O)(=O)c1ccc2ccccc2c1)C(=O)NO]

Following typical methods for sulfonylation and method L, the title compound is prepared from (R)-2-amino-3,3-dim-ethyl-butyric acid and naphthalene-2-sulfonyl chloride. ¹HNMR (400 MHz, MeOD): δ 1.25 (s, 9H), 3.73 (s, 1H), 7.94 (m, 2H), 8.13 (d, 1H, J=7 Hz), 8.25 (d, 1H, J=7 Hz), 8.3 (m, 2H), 8.7 (s, 1H). LCMS (m/z): 335 (M−1).

Example 94

(R)-1-(4-Methyl-3,4-dihydro-2H-benzo[1,4]oxazine-7-sulfonyl)-1,2,3,6-tetrahydro-pyridine-2-carboxylic acid hydroxyamide

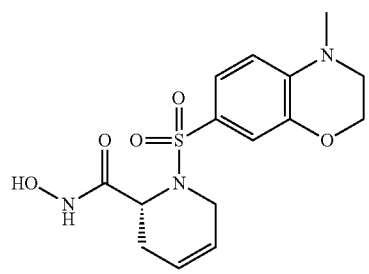

Following methods B, G and L, the title compound is prepared from (R)-2-amino-pent-4-enoic acid ethyl ester, 4-methyl-3,4-dihydro-2H-benzo[1,4]oxazine-7-sulfonyl chloride and 3-bromo-propene. ¹HNMR (400 MHz, CDCl3): δ 2.05 (m, 1H), 2.75-2.80 (m, 1H), 3.3 (t, 2H, J=5 Hz), 3.82 (d, 1H, J=16 Hz), 4.10 (d, 1H, J=16 Hz), 4.35 (t, 2H, J=5 Hz), 4.69 (d, 1H, J=6.5 Hz), 5.5-5.8 (m, 2H), 6.8 (d, 1H, J=8 Hz), 6.97 (d, 1H, J=2 Hz), 7.05 (dd, 1H, J=2 Hz, J=8 Hz). LCMS (m/z): 354 (M+1).

Example 95

(R)-1-(2,3,4a,8a-Tetrahydro-benzo[1,4]dioxine-6-sulfonyl)-1,2,3,6-tetrahydro-pyridine-2-carboxylic acid hydroxyamide

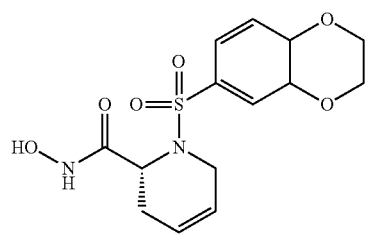 [SMILES: O=C(NO)[C@H]1CC=CCN1S(=O)(=O)C1=CC2OCCOC2C=C1]

Following methods B, G and L, the title compound is prepared from (R)-2-amino-pent-4-enoic acid ethyl ester, 2,3-dihydro-benzo[1,4]dioxine-6-sulfonyl chloride and 3-bromo-propene. ¹HNMR (400 MHz, MeOD): δ 2.10-2.20 (m, 1H), 2.40-2.50 (m, 1H), 3.9-4.1 (m, 2H), 4.30 (d, 4H, J=4 Hz), 4.60 (d, 2H, J=6 Hz), 5.65 (br, 2H), 6.95 (d, 1H, J=9 Hz), 7.34 (m, 2H). LCMS (m/z): 341 (M−1).

Example 96

(R)-1-(6-Morpholin-4-yl-pyridine-3-sulfonyl)-1,2,3,6-tetrahydro-pyridine-2-carboxylic acid hydroxyamide

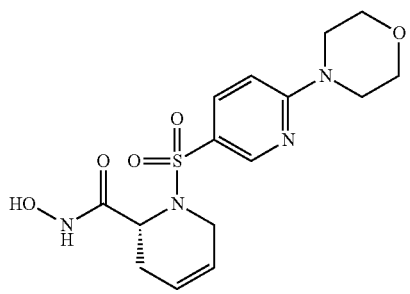

Following methods B, G and L, the title compound is prepared from (R)-2-amino-pent-4-enoic acid ethyl ester, 6-morpholin-4-yl-pyridine-3-sulfonyl chloride and 3-bromopropene. ¹HNMR (400 MHz, DMSO): δ 2.25-2.45 (br, 4H), 3.63 (t, 4H, J=5 Hz), 3.77 (t, 4H, J=5 Hz), 4.0 (dd, 2H), 4.7 (d, 1H, J=7 Hz), 5.60 (br, 2H), 6.85 (d, 1H, J=8 Hz), 7.85 (dd, 1H, J=8 Hz), 8.45 (d, 1H, J=2 Hz). LCMS (m/z): 369 (M+1).

Example 97

(R)-1-(3,4-Dimethoxy-benzenesulfonyl)-1,2,3,6-tetrahydro-pyridine-2-carboxylic acid hydroxyamide

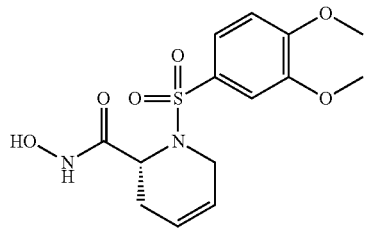 [SMILES: COc1ccc(S(=O)(=O)N2CC=CC[C@@H]2C(=O)NO)cc1OC]

Following methods B, G and L, the title compound is prepared from (R)-2-amino-pent-4-enoic acid ethyl ester, 3,4-dimethoxy-benzenesulfonyl chloride and 3-bromo-propene. ¹HNMR (400 MHz, DMSO): δ 2.10-2.25 (m, 1H), 2.30-2.45 (m, 1H), 3.84 (s, 3H), 3.86 (s, 3H), 3.95-4.15 (m, 2H), 4.60 (d, 1H, J=6 Hz), 5.65 (br, 2H), 7.05 (d, 1H, J=8.5 Hz), 7.82 (d, 1H, J=2 Hz), 7.45 (dd, 1H, J=2 Hz, J=8 Hz). LCMS (m/z): 343 (M+1).

Example 98

(R)-2-[(Benzothiazole-2-sulfonyl)-(3-methyl-butyl)-amino]-N-hydroxy-3-methyl-butyramide

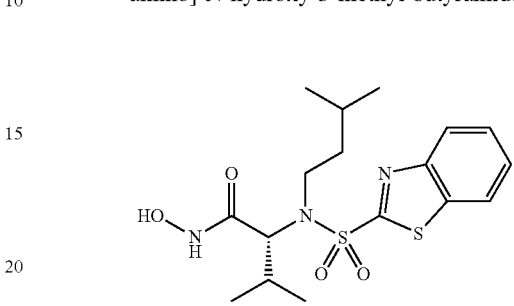

Following methods A and L, the title compound is prepared from (R)-2-amino-3-methyl-butyric acid tert-butyl ester, naphthalene-2-sulfonyl chloride and 1-iodo-3-methyl-butane. ¹HNMR (400 MHz, MeOD): δ 0.85-0.95 (m, 12H), 1.4-1.75 (m, 4H), 2.2-2.3 (m, 1H), 3.4-3.5 (m, 1H), 3.7-3.8 (m, 1H), 3.9-4.05 (d, 1H, J=9 Hz), 7.55-7.7 (m, 2H), 8.08 (d, 1H, J=7 Hz), 8.22 (d, 1H, J=7 Hz). LCMS (m/z): 400 (M+1).

Benzothiazole-2-sulfonyl chloride

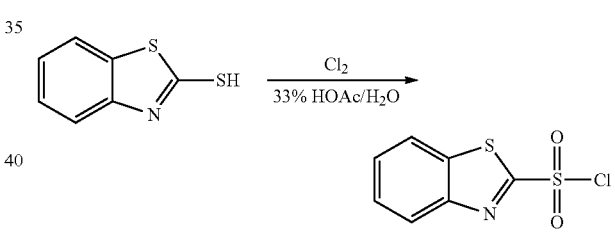

A suspension of 2-mercapto-benzothiazole (2 g, 11.98 mmol) in 30% acetic acid/water is stirred at 0° C. as chlorine gas is bubbled for 15 min, then the reaction mixture is filtered, the filter cake is washed with water, and used in the next step without any additional purification.

| # | Structure | Structure Name | MMP2 IC$_{50}$ [μM] | MMP13 IC$_{50}$ [μM] | MW (Calc'd) | LCMS |
|---|---|---|---|---|---|---|
| 1 | 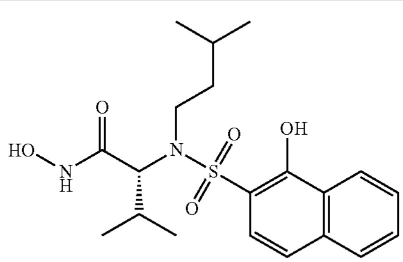 [SMILES: CC(C)CCN([C@@H](C(=O)NO)C(C)C)S(=O)(=O)c1ccc2ccccc2c1O] | N-Hydroxy-2-[(1-hydroxy-naphthalene-2-sulfonyl)-(3-methyl-butyl)-amino]-3-methyl-butyramide | >3 | 0.672 | 408.52 | 409 (M+1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 2 | 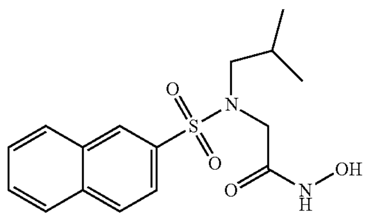 [SMILES: CC(C)CN(CC(=O)NO)S(=O)(=O)c1ccc2ccccc2c1] | N-Hydroxy-2-[isobutyl-(naphthalene-2-sulfonyl)-amino]-acetamide | 0.133 | 0.0184 | 336.41 | 337.1 (M + 1) |
| 3 | 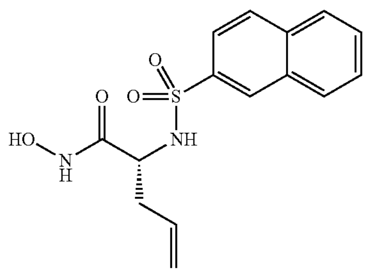 [SMILES: C=CC[C@@H](NS(=O)(=O)c1ccc2ccccc2c1)C(=O)NO] | 2-(Naphthalene-2-sulfonylamino)-pent-4-enoic acid hydroxyamide | 0.0222 | 0.0356 | 320.37 | 321 (M + 1) |
| 4 | 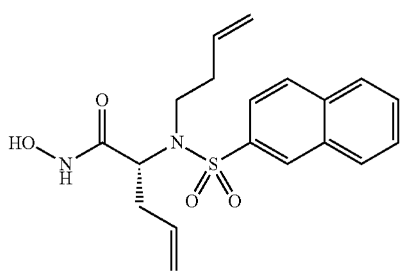 [SMILES: C=CCCN([C@H](CC=C)C(=O)NO)S(=O)(=O)c1ccc2ccccc2c1] | 2-[But-3-enyl-(naphthalene-2-sulfonyl)-amino]-pent-4-enoic acid hydroxyamide | 0.0507 | 0.0007 | 374.46 | 375 (M + 1) |
| 5 | 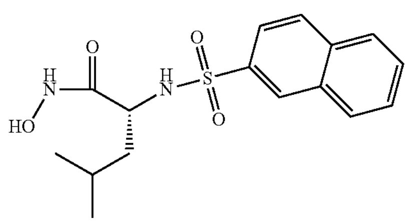 [SMILES: CC(C)C[C@@H](NS(=O)(=O)c1ccc2ccccc2c1)C(=O)NO] | 4-Methyl-2-(naphthalene-2-sulfonylamino)-pentanoic acid hydroxyamide | 0.0575 | 0.0405 | 336.41 | 335.33 (M − 1) |
| 6 | 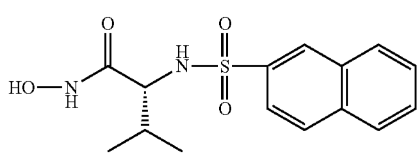 [SMILES: CC(C)[C@@H](NS(=O)(=O)c1ccc2ccccc2c1)C(=O)NO] | N-Hydroxy-3-methyl-2-(naphthalene-2-sulfonylamino)-butyramide | 0.0960 | 0.033 | 322.39 | 321.10 (M − 1) |
| 7 | 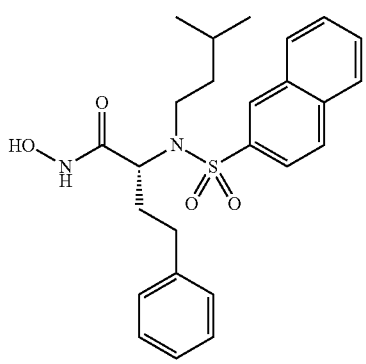 [SMILES: CC(C)CCN([C@H](CCc1ccccc1)C(=O)NO)S(=O)(=O)c1ccc2ccccc2c1] | N-Hydroxy-2-[(3-methyl-butyl)-(naphthalene-2-sulfonyl)-amino]-4-phenyl-butyramide | 0.458 | 0.0259 | 454.59 | 455 (M + 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 8 | 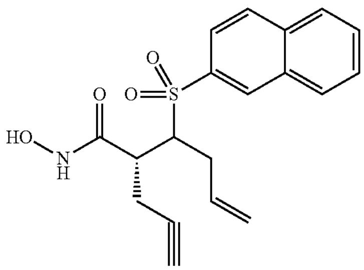 | 2-[Allyl-(naphthalene-2-sulfonyl)-amino]-pent-4-ynoic acid hydroxyamide | 0.125 | 0.0035 | 358.42 | 359 (M + 1) |
| 9 | 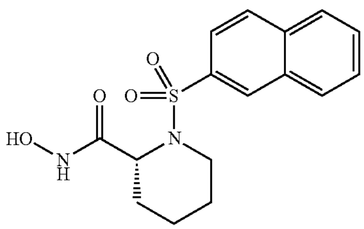 | 1-(Naphthalene-2-sulfonyl)-piperidine-2-carboxylic acid hydroxyamide | 0.0488 | 0.0049 | 334.4 | 335 (M + 1) |
| 10 | 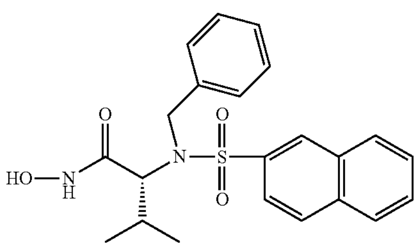 [SMILES: CC(C)[C@H](C(=O)NO)N(Cc1ccccc1)S(=O)(=O)c1ccc2ccccc2c1] | 2-[Benzyl-(naphthalene-2-sulfonyl)-amino]-N-hydroxy-3-methyl-butyramide | 0.706 | 0.0281 | 412.51 | 411.16 (M − 1) |
| 11 | 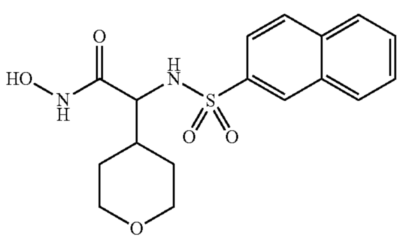 [SMILES: O=C(NO)C(NS(=O)(=O)c1ccc2ccccc2c1)C1CCOCC1] | N-Hydroxy-2-(naphthalene-2-sulfonylamino)-2-(tetrahydro-pyran-4-yl)-acetamide | 0.0927 | 0.0509 | 364.42 | 363.4 (M − 1) |
| 12 | 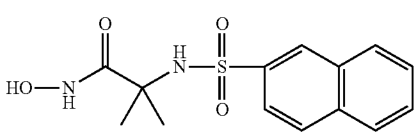 [SMILES: CC(C)(NS(=O)(=O)c1ccc2ccccc2c1)C(=O)NO] | N-Hydroxy-2-methyl-2-(naphthalene-2-sulfonylamino)-propionamide | 0.793 | 0.761 | 308.36 | 307.21 (M − 1) |
| 13 | 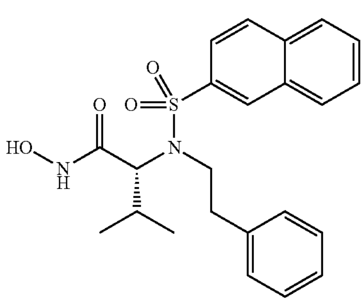 [SMILES: CC(C)[C@H](C(=O)NO)N(CCc1ccccc1)S(=O)(=O)c1ccc2ccccc2c1] | N-Hydroxy-3-methyl-2-[(naphthalene-2-sulfonyl)-phenethyl-amino]-butyramide | 0.200 | 0.0024 | 426.54 | 427 (M + 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 14 | 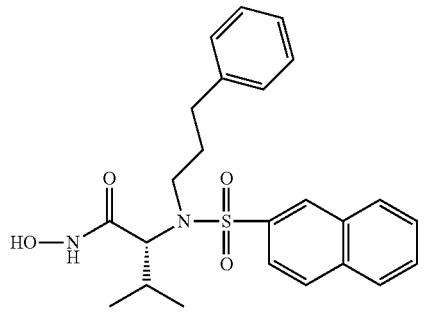 [SMILES: CC(C)[C@H](C(=O)NO)N(CCCc1ccccc1)S(=O)(=O)c1ccc2ccccc2c1] | N-Hydroxy-3-methyl-2-[(naphthalene-2-sulfonyl)-(3-phenyl-propyl)-amino]-butyramide | 0.798 | 0.0242 | 440.57 | 439.15 (M − 1) |
| 15 | 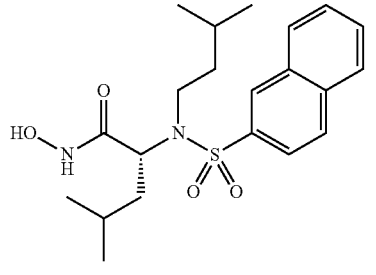 [SMILES: CC(C)CCN([C@H](CC(C)C)C(=O)NO)S(=O)(=O)c1ccc2ccccc2c1] | 4-Methyl-2-[(3-methyl-butyl)-(naphthalene-2-sulfonyl)-amino]-pentanoic acid hydroxyamide | 0.128 | 0.0006 | 406.55 | 407 (M + 1) |
| 16 | 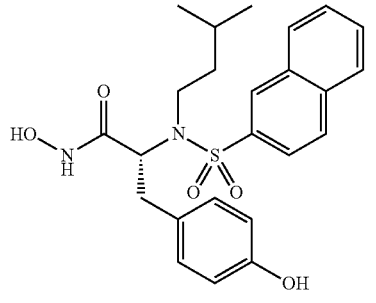 [SMILES: CC(C)CCN([C@H](Cc1ccc(O)cc1)C(=O)NO)S(=O)(=O)c1ccc2ccccc2c1] | N-Hydroxy-3-(4-hydroxy-phenyl)-2-[(3-methyl-butyl)-(naphthalene-2-sulfonyl)-amino]-propionamide | 0.174 | 0.0258 | 456.57 | 457 (M + 1) |
| 17 | 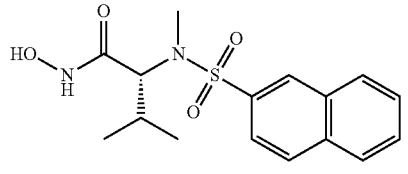 [SMILES: CC(C)[C@H](C(=O)NO)N(C)S(=O)(=O)c1ccc2ccccc2c1] | N-Hydroxy-3-methyl-2-[methyl-(naphthalene-2-sulfonyl)-amino]-butyramide | 0.0542 | 0.0029 | 336.41 | 335.3 (M − 1) |
| 18 | 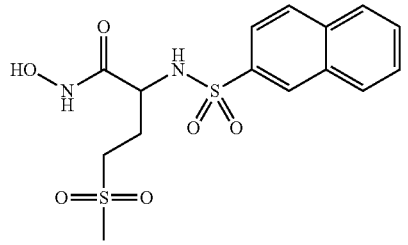 [SMILES: CS(=O)(=O)CCC(NS(=O)(=O)c1ccc2ccccc2c1)C(=O)NO] | N-Hydroxy-4-methanesulfonyl-2-(naphthalene-2-sulfonylamino)-butyramide | 0.157 | 0.153 | 386.45 | 385.3 (M − 1) |
| 19 | 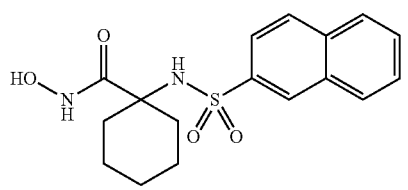 [SMILES: O=C(NO)C1(NS(=O)(=O)c2ccc3ccccc3c2)CCCCC1] | 1-(Naphthalene-2-sulfonylamino)-cyclohexanecarboxylic acid hydroxyamide | 0.451 | 0.727 | 348.42 | 347.3 (M − 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 20 | 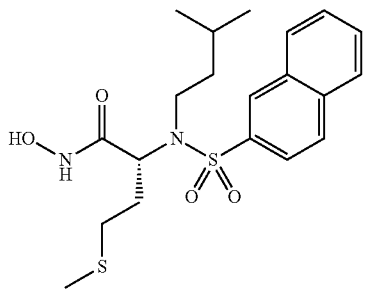 [SMILES: CSCC[C@H](C(=O)NO)N(CCC(C)C)S(=O)(=O)c1ccc2ccccc2c1] | N-Hydroxy-2-[(3-methyl-butyl)-(naphthalene-2-sulfonyl)-amino]-4-methylsulfanyl-butyramide | 0.0121 | 0.0003 | 424.59 | 425 (M + 1) |
| 21 | 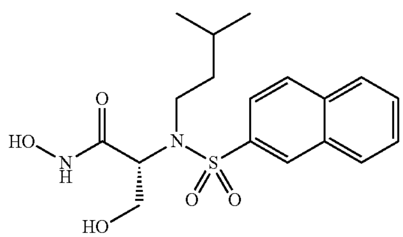 [SMILES: CC(C)CCN([C@H](CO)C(=O)NO)S(=O)(=O)c1ccc2ccccc2c1] | 3,N-Dihydroxy-2-[(3-methyl-butyl)-(naphthalene-2-sulfonyl)-amino]-propionamide | 0.0825 | 0.0013 | 380.47 | 381 (M + 1) |
| 22 | 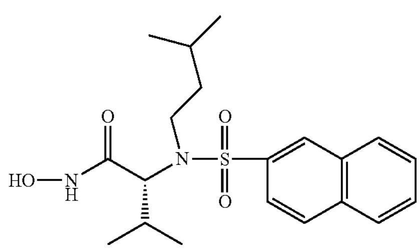 [SMILES: CC(C)CCN([C@@H](C(=O)NO)C(C)C)S(=O)(=O)c1ccc2ccccc2c1] | N-Hydroxy-3-methyl-2-[(3-methyl-butyl)-(naphthalene-2-sulfonyl)-amino]-butyramide | 0.384 | 0.0031 | 392.52 | 393.1 (M + 1) |
| 23 | 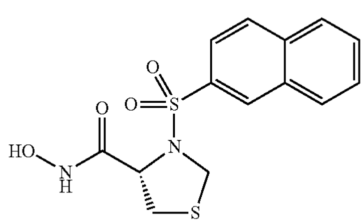 [SMILES: O=C(NO)[C@H]1CSCN1S(=O)(=O)c1ccc2ccccc2c1] | (S)-3-(Naphthalene-2-sulfonyl)-thiazolidine-4-carboxylic acid hydroxyamide | | | 338.41 | 339.17 (M + 1) |
| 24 | 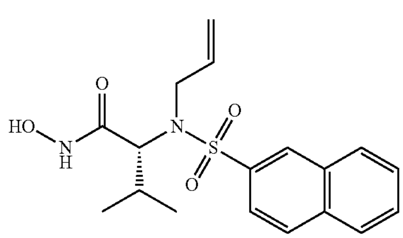 [SMILES: C=CCN([C@@H](C(=O)NO)C(C)C)S(=O)(=O)c1ccc2ccccc2c1] | 2-[Allyl-(naphthalene-2-sulfonyl)-amino]-N-hydroxy-3-methyl-butyramide | 0.0904 | 0.0034 | 362.45 | 363 (M + 1) |

| # | Structure Name | MMP2 IC$_{50}$ [μM] | MMP13 IC$_{50}$ [μM] | MW (Calc'd) | LCMS |
|---|---|---|---|---|---|
| 25 | 3-(4-Benzyloxy-phenyl)-N-hydroxy-2-[(3-methyl-butyl)-(naphthalene-2-sulfonyl)-amino]-propionamide | 1.96 | 0.0441 | 546.69 | 547 (M + 1) |
| 26 | 1-(Naphthalene-2-sulfonyl)-1,2,3,6-tetrahydro-pyridine-2-carboxylic acid hydroxyamide | 0.0186 | 0.0017 | 332.38 | 333 (M + 1) |
| 27 | 2-[Benzyl-(7-ethoxy-naphthalene-2-sulfonyl)-amino]-N-hydroxy-3-methyl-butyramide | 4.40 | 0.535 | 456.57 | 455.37 (M − 1) |
| 28 | N-Hydroxy-3-methyl-2-[(naphthalene-2-sulfonyl)-pyridin-4-ylmethyl-amino]-butyramide | 0.200 | 0.0068 | 413.5 | 414 (M + 1) |
| 29 | 2-[(6-Ethyl-naphthalene-2-sulfonyl)-(3-methyl-butyl)-amino]-N-hydroxy-3-methyl-butyramide | 0.0447 | <0.0003 | 420.58 | 419.32 (M − 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 30 | 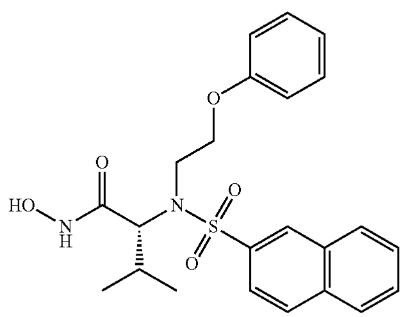 [SMILES: CC(C)[C@H](C(=O)NO)N(CCOc1ccccc1)S(=O)(=O)c1ccc2ccccc2c1] | N-Hydroxy-3-methyl-2-[(naphthalene-2-sulfonyl)-(2-phenoxy-ethyl)-amino]-butyramide | 0.0612 | 0.0021 | 442.54 | 441.4 (M − 1) |
| 31 | 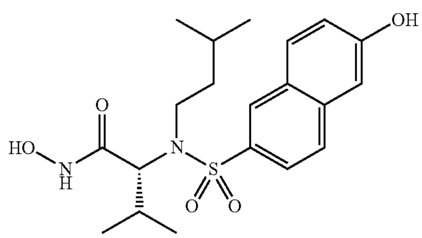 [SMILES: CC(C)CCN([C@@H](C(=O)NO)C(C)C)S(=O)(=O)c1ccc2cc(O)ccc2c1] | N-Hydroxy-2-[(6-hydroxy-naphthalene-2-sulfonyl)-(3-methyl-butyl)-amino]-3-methyl-butyramide | 0.178 | 0.0010 | 408.52 | 407.29 (M − 1) |
| 32 | 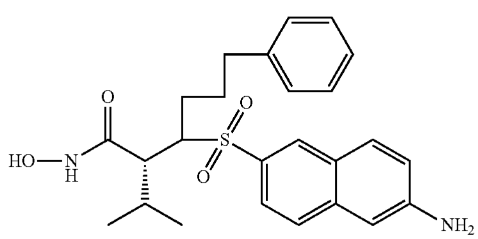 [SMILES: CC(C)[C@H](C(=O)NO)C(CCCc1ccccc1)S(=O)(=O)c1ccc2cc(N)ccc2c1] | 2-[(6-Amino-naphthalene-2-sulfonyl)-(3-phenyl-propyl)-amino]-N-hydroxy-3-methyl-butyramide | 0.0822 | 0.0010 | 455.58 | 454.27 (M − 1) |
| 33 | 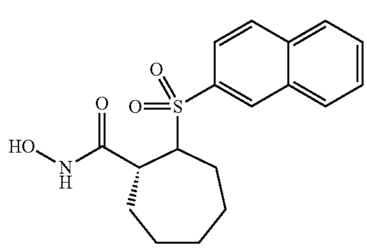 | 1-(Naphthalene-2-sulfonyl)-azepane-2-carboxylic acid hydroxyamide | 0.0745 | 0.0087 | 348.42 | 349 (M + 1) |
| 34 | 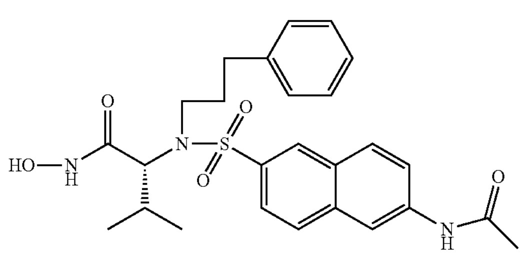 [SMILES: CC(=O)Nc1ccc2cc(S(=O)(=O)N(CCCc3ccccc3)[C@@H](C(=O)NO)C(C)C)ccc2c1] | 2-[(6-Acetylamino-naphthalene-2-sulfonyl)-(3-phenyl-propyl)-amino]-N-hydroxy-3-methyl-butyramide | 2.90 | 1.31 | 497.62 | 496.3 |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 35 | 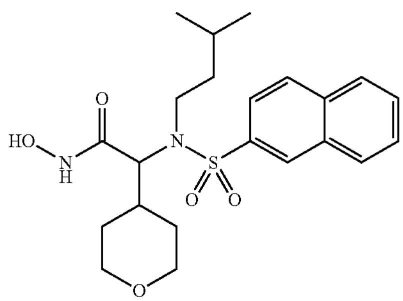 [SMILES: CC(C)CCN(C(C(=O)NO)C1CCOCC1)S(=O)(=O)c1ccc2ccccc2c1] | N-Hydroxy-2-[(3-methyl-butyl)-(naphthalene-2-sulfonyl)-amino]-2-(tetrahydro-pyran-4-yl)-acetamide | 0.0810 | 0.0119 | 434.56 | 433.5 (M − 1) |
| 36 | 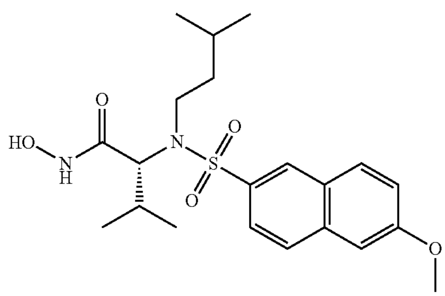 [SMILES: COc1ccc2cc(S(=O)(=O)N(CCC(C)C)[C@@H](C(=O)NO)C(C)C)ccc2c1] | N-Hydroxy-2-[(6-methoxy-naphthalene-2-sulfonyl)-(3-methyl-butyl)-amino]-3-methyl-butyramide | 0.180 | 0.0013 | 422.55 | 421.36 (M − 1) |
| 37 | 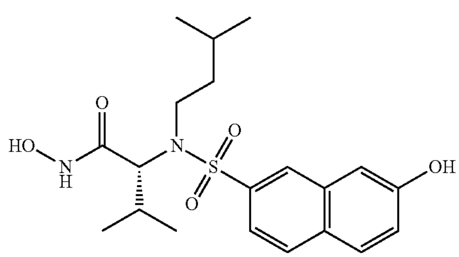 [SMILES: CC(C)CCN([C@@H](C(=O)NO)C(C)C)S(=O)(=O)c1ccc2ccc(O)cc2c1] | N-Hydroxy-2-[(7-hydroxy-naphthalene-2-sulfonyl)-(3-methyl-butyl)-amino]-3-methyl-butyramide | 3.286 | 0.242 | 408.52 | 407.3 (M − 1) |
| 38 | 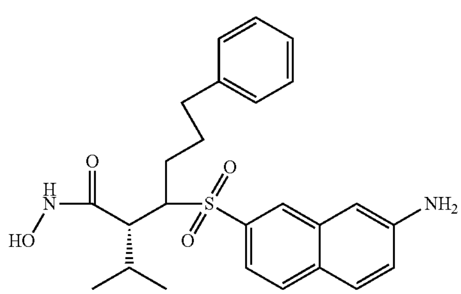 [SMILES: CC(C)[C@H](C(=O)NO)C(CCCc1ccccc1)S(=O)(=O)c1ccc2ccc(N)cc2c1] | 2-[(7-Amino-naphthalene-2-sulfonyl)-(3-phenyl-propyl)-amino]-N-hydroxy-3-methyl-butyramide | >0.3 | 0.190 | 455.58 | 454.37 (M − 1) |
| 39 | 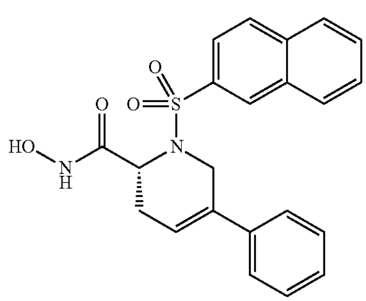 [SMILES: O=C(NO)[C@H]1CC=C(c2ccccc2)CN1S(=O)(=O)c1ccc2ccccc2c1] | 1-(Naphthalene-2-sulfonyl)-5-phenyl-1,2,3,6-tetrahydro-pyridine-2-carboxylic acid hydroxyamide | 0.0278 | 0.0014 | 408.48 | 409 (M + 1) |

-continued

| # | Structure Name | MMP2 IC$_{50}$ [μM] | MMP13 IC$_{50}$ [μM] | MW (Calc'd) | LCMS |
|---|---|---|---|---|---|
| 40 | N-Hydroxy-2-[(7-methoxy-naphthalene-2-sulfonyl)-(3-methyl-butyl)-amino]-3-methyl-butyramide | 4.37 | 0.480 | 422.55 | 423 (M + 1) |
| 41 | 2-[[2-(4-Fluoro-phenoxy)-ethyl]-(naphthalene-2-sulfonyl)-amino]-N-hydroxy-3-methyl-butyramide | 1.13 | 0.0387 | 460.53 | 459.3 (M − 1) |
| 42 | 2-[(6-Ethoxy-naphthalene-2-sulfonyl)-(3-methyl-butyl)-amino]-N-hydroxy-3-methyl-butyramide | 0.307 | 0.0036 | 436.57 | 435.34 (M − 1) |
| 43 | 2-[Benzyl-(6-p-tolylamino-naphthalene-2-sulfonyl)-amino]-N-hydroxy-3-methyl-butyramide | >0.3 | 0.118 | 517.65 | 516.32 (M − 1) |
| 44 | 1-(Naphthalene-2-sulfonyl)-4-vinyl-1,2,3,6-tetrahydro-pyridine-2-carboxylic acid hydroxyamide | 0.0301 | 0.0018 | 358.42 | 359 (M + 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 45 | 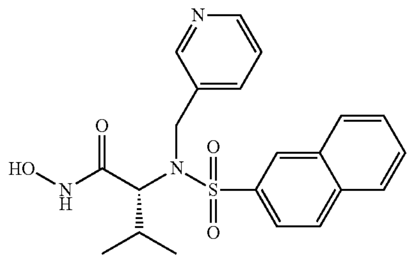 [SMILES: CC(C)[C@H](C(=O)NO)N(Cc1cccnc1)S(=O)(=O)c1ccc2ccccc2c1] | N-Hydroxy-3-methyl-2-[(naphthalene-2-sulfonyl)-pyridin-3-ylmethyl-amino]butyramide | 0.0255 | 0.0147 | 413.5 | 412.2 (M − 1) |
| 46 | 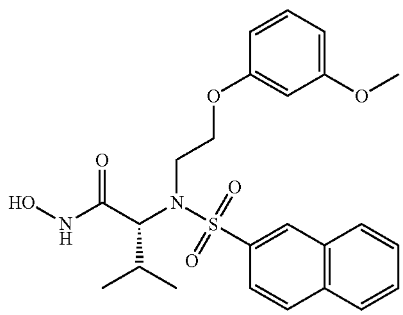 [SMILES: COc1cccc(OCCN([C@@H](C(=O)NO)C(C)C)S(=O)(=O)c2ccc3ccccc3c2)c1] | N-Hydroxy-2-[[2-(3-methoxy-phenoxy)-ethyl]-(naphthalene-2-sulfonyl)-amino]-3-methyl-butyramide | 0.655 | 0.0139 | 472.56 | 473 (M + 1) |
| 47 | 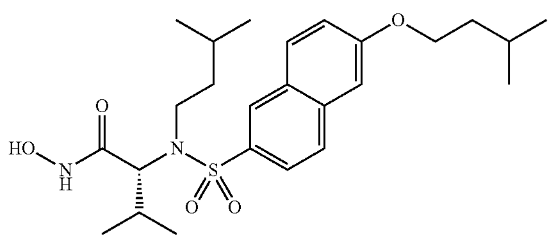 [SMILES: CC(C)CCOc1ccc2cc(S(=O)(=O)N(CCC(C)C)[C@@H](C(=O)NO)C(C)C)ccc2c1] | N-Hydroxy-3-methyl-2-[[6-(3-methyl-butoxy)-naphthalene-2-sulfonyl]-(3-methyl-butyl)-amino]-butyramide | 0.931 | 0.176 | 478.66 | 477.36 (M − 1) |
| 48 | 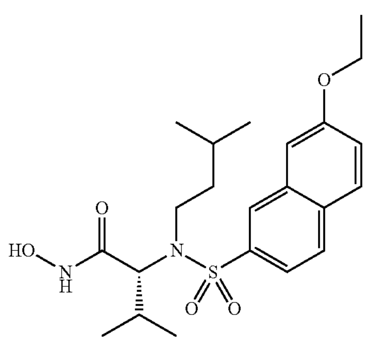 [SMILES: CCOc1ccc2ccc(S(=O)(=O)N(CCC(C)C)[C@@H](C(=O)NO)C(C)C)cc2c1] | 2-[(7-Ethoxy-naphthalene-2-sulfonyl)-(3-methyl-butyl)-amino]-N-hydroxy-3-methyl-butyramide | 9.20 | 0.603 | 436.57 | 435.32 (M − 1) |
| 49 | 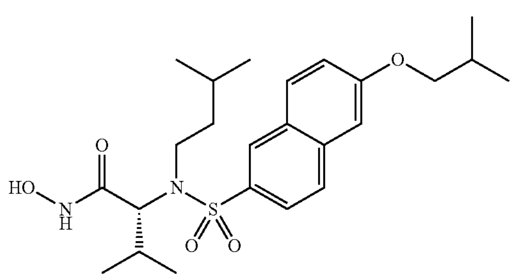 [SMILES: CC(C)CCN([C@@H](C(=O)NO)C(C)C)S(=O)(=O)c1ccc2cc(OCC(C)C)ccc2c1] | N-Hydroxy-2-[(6-isobutoxy-naphthalene-2-sulfonyl)-(3-methyl-butyl)-amino]-3-methyl-butyramide | 0.102 | 0.0134 | 464.63 | 463.43 (M − 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 50 | 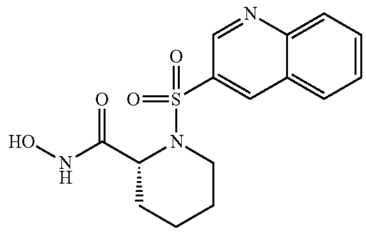 [SMILES: O=C(NO)[C@H]1CCCCN1S(=O)(=O)c1cnc2ccccc2c1] | 1-(Quinoline-3-sulfonyl)-piperidine-2-carboxylic acid hydroxyamide | 0.975 | 0.132 | 335.38 | 336 (M + 1) |
| 51 | 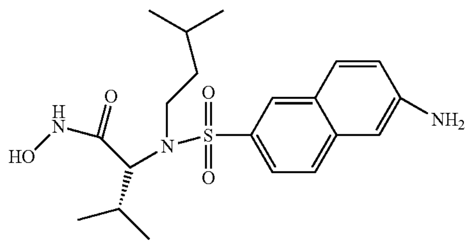 | 2-[(6-Amino-naphthalene-2-sulfonyl)-(3-methyl-butyl)-amino]N-hydroxy-3-methyl-butyramide | 1.13 | 0.0900 | 407.54 | 406.2 (M − 1) |
| 52 | 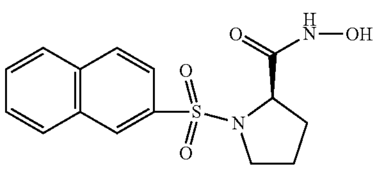 [SMILES: O=C(NO)[C@H]1CCCN1S(=O)(=O)c1ccc2ccccc2c1] | 1-(Naphthalene-2-sulfonyl)-pyrrolidine-2-carboxylic acid hydroxyamide | 0.350 | 0.293 | 320.37 | 319.18 (M − 1) |
| 53 | 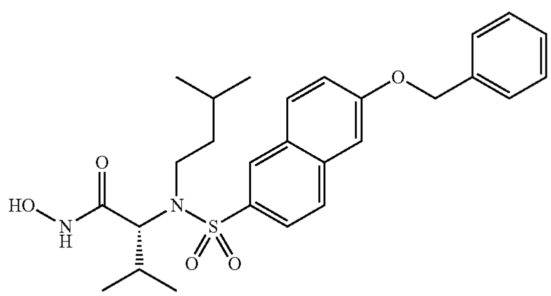 [SMILES: CC(C)CCN([C@@H](C(=O)NO)C(C)C)S(=O)(=O)c1ccc2cc(OCc3ccccc3)ccc2c1] | 2-[(6-Benzyloxy-naphthalene-2-sulfonyl)-(3-methyl-butyl)-amino]-N-hydroxy-3-methyl-butyramide | 1.61 | 0.165 | 498.65 | 497.44 (M − 1) |
| 54 | 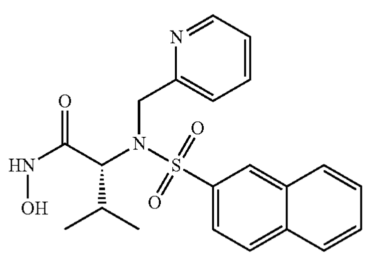 [SMILES: CC(C)[C@H](C(=O)NO)N(Cc1ccccn1)S(=O)(=O)c1ccc2ccccc2c1] | N-Hydroxy-3-methyl-2-[(naphthalene-2-sulfonyl)-pyridin-2-ylmethyl-amino]-butyramide | 0.232 | 0.0022 | 413.5 | 414 (M + 1) |
| 55 | 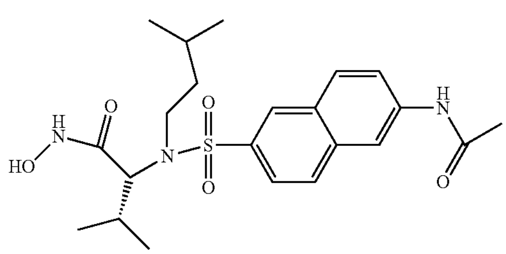 | 2-[(6-Acetylamino-naphthalene-2-sulfonyl)-(3-methyl-butyl)-amino]-N-hydroxy-3-methyl-butyramide | 0.0813 | 0.0031 | 449.57 | 448.3 (M − 1) |

| # | Structure Name | MMP2 IC$_{50}$ [μM] | MMP13 IC$_{50}$ [μM] | MW (Calc'd) | LCMS |
|---|---|---|---|---|---|
| 56 | 2-[(2-Dimethylamino-ethyl)-(naphthalene-2-sulfonyl)-amino]-N-hydroxy-3-methyl-butyramide | 0.607 | 0.0324 | 393.51 | 392.3 (M − 1) |
| 57 | N-Hydroxy-3-methyl-2-{(3-methyl-butyl)-[7-(3-methyl-butylamino)-naphthalene-2-sulfonyl]-amino}-butyramide | >3 | 1.58 | 477.67 | 476.3 (M − 1) |
| 58 | 2-[[2-(4-Chloro-phenoxy)-ethyl]-(naphthalene-2-sulfonyl)-amino]-N-hydroxy-3-methyl-butyramide | 2.65 | 0.116 | 476.98 | 477 (M + 1) |
| 59 | 3-tert-Butoxy-N-hydroxy-2-[(3-methyl-butyl)-(naphthalene-2-sulfonyl)-amino]-propionamide | 0.199 | 0.0023 | 436.57 | 437 (M + 1) |
| 60 | 5-Methyl-1-(naphthalene-2-sulfonyl)-1,2,3,6-tetrahydro-pyridine-2-carboxylic acid hydroxyamide | 0.0125 | 0.0009 | 346.41 | 345.2 (M − 1) |

-continued

| # | Structure Name | MMP2 IC$_{50}$ [μM] | MMP13 IC$_{50}$ [μM] | MW (Calc'd) | LCMS |
|---|---|---|---|---|---|
| 61 | 2-[(7-Acetylamino-naphthalene-2-sulfonyl)-(3-methyl-butyl)-amino]-N-hydroxy-3-methyl-butyramide | 0.0228 | 0.0005 | 449.57 | 448.40 (M − 1) |
| 62 | 2-[[2-(3-Chloro-phenoxy)-ethyl]-(naphthalene-2-sulfonyl)-amino]-N-hydroxy-3-methyl-butyramide | 3.89 | 0.138 | 476.98 | 475.4 (M − 1) |
| 63 | 1-(Quinoline-6-sulfonyl)-1,2,3,6-tetrahydro-pyridine-2-carboxylic acid hydroxyamide | 0.0547 | 0.0105 | 333.37 | 334 (M + 1) |
| 64 | 2-[[2-(2-Chloro-phenoxy)-ethyl]-(naphthalene-2-sulfonyl)-amino]-N-hydroxy-3-methyl-butyramide | 0.898 | 0.0161 | 476.98 | 475.3 (M − 1) |
| 65 | N-Hydroxy-2-methyl-2-[(3-methyl-butyl)-(naphthalene-2-sulfonyl)-amino]-propionamide | 2.86 | 2.26 | 378.49 | 377.29 (M − 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 66 | 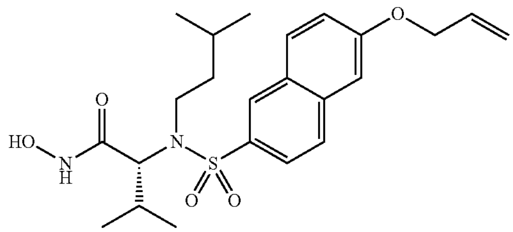 [SMILES: C=CCOc1ccc2cc(S(=O)(=O)N(CCC(C)C)[C@@H](C(=O)NO)C(C)C)ccc2c1] | 2-[(6-Allyloxy-naphthalene-2-sulfonyl)-(3-methyl-butyl)-amino]-N-hydroxy-3-methyl-butyramide | 0.128 | 0.0073 | 448.59 | 447.31 (M − 1) |
| 67 | 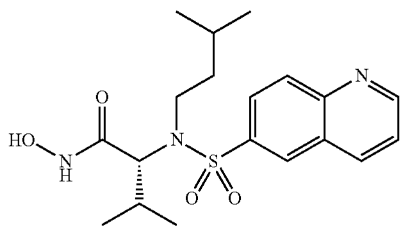 [SMILES: CC(C)CCN([C@@H](C(=O)NO)C(C)C)S(=O)(=O)c1ccc2ncccc2c1] | N-Hydroxy-3-methyl-2-[(3-methyl-butyl)-(quinoline-6-sulfonyl)-amino]-butyramide | 0.306 | 0.0121 | 393.51 | 394 (M + 1) |
| 68 | 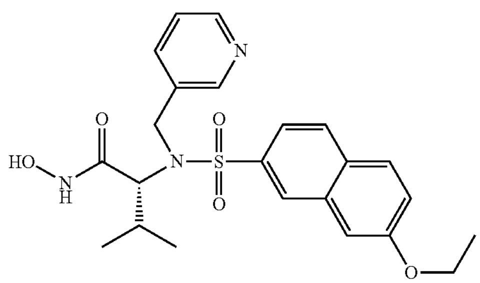 [SMILES: CCOc1ccc2ccc(S(=O)(=O)N(Cc3cccnc3)[C@@H](C(=O)NO)C(C)C)cc2c1] | 2-[(7-Ethoxy-naphthalene-2-sulfonyl)-pyridin-3-ylmethyl-amino]-N-hydroxy-3-methyl-butyramide | 0.976 | 0.0287 | 457.55 | 456.26 (M − 1) |
| 69 | 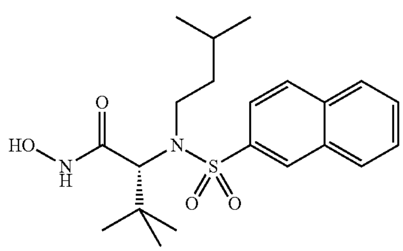 [SMILES: CC(C)CCN([C@@H](C(=O)NO)C(C)(C)C)S(=O)(=O)c1ccc2ccccc2c1] | N-Hydroxy-3,3-dimethyl-2-[(3-methyl-butyl)-(naphthalene-2-sulfonyl)-amino]-butyramide | 3.67 | 0.0344 | 406.55 | 405 (M − 1) |
| 70 | 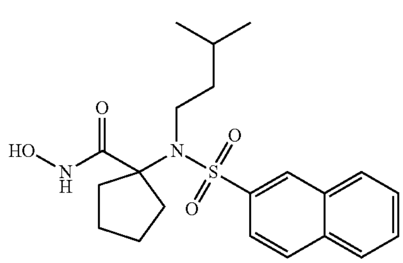 [SMILES: CC(C)CCN(C1(C(=O)NO)CCCC1)S(=O)(=O)c1ccc2ccccc2c1] | 1-[(3-Methyl-butyl)-(naphthalene-2-sulfonyl)-amino]-cyclopentanecarboxylic acid hydroxyamide | 0.940 | 0.212 | 404.53 | 403.3 (M − 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 71 | 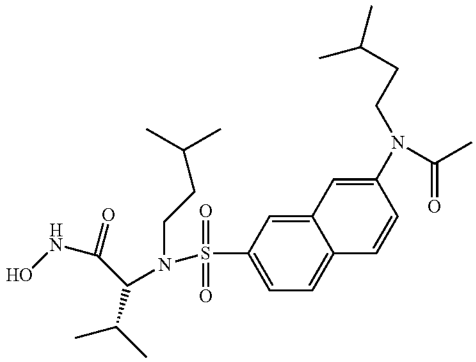 | 2-[{7-[Acetyl-(3-methyl-butyl)-amino]-naphthalene-2-sulfonyl}-(3-methyl-butyl)-amino]-N-hydroxy-3-methyl-butyramide | >30 | >30 | 519.71 | 518.28 (M − 1) |
| 72 | 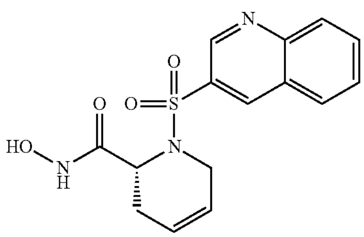 [SMILES: O=C(NO)[C@H]1CC=CCN1S(=O)(=O)c1cnc2ccccc2c1] | 1-(Quinoline-3-sulfonyl)-1,2,3,6-tetrahydro-pyridine-2-carboxylic acid hydroxyamide | 0.853 | 0.0957 | 333.37 | 334 (M + 1) |
| 73 | 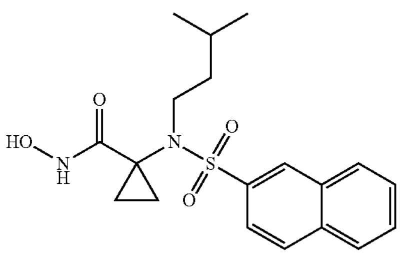 [SMILES: CC(C)CCN(C1(C(=O)NO)CC1)S(=O)(=O)c1ccc2ccccc2c1] | 1-[(3-Methyl-butyl)-(naphthalene-2-sulfonyl)-amino]-cyclopropanecarboxylic acid hydroxyamide | 0.402 | 0.035 | 376.48 | 375.1 (M − 1) |
| 74 | 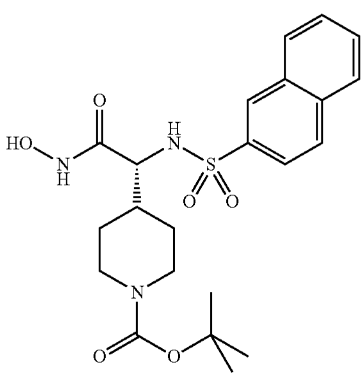 [SMILES: CC(C)(C)OC(=O)N1CCC([C@@H](NS(=O)(=O)c2ccc3ccccc3c2)C(=O)NO)CC1] | 4-[Hydroxycarbamoyl-(naphthalene-2-sulfonylamino)-methyl]-piperidine-1-carboxylic acid tert-butyl ester | 0.0004 | 0.0004 | 463.56 | 462.5 (M − 1) |
| 75 | 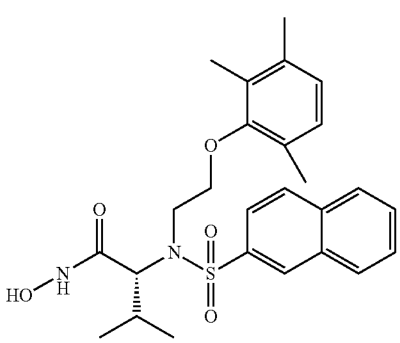 [SMILES: Cc1ccc(C)c(OCCN([C@@H](C(=O)NO)C(C)C)S(=O)(=O)c2ccc3ccccc3c2)c1C] | N-Hydroxy-3-methyl-2-{(naphthalene-2-sulfonyl)-[2-(2,3,6-trimethyl-phenoxy)-ethyl]-amino}-butyramide | 3.11 | 0.0673 | 484.62 | 483.4 (M − 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 76 | 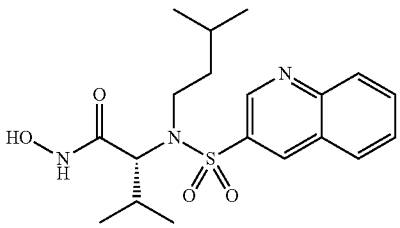 [SMILES: CC(C)CCN([C@@H](C(=O)NO)C(C)C)S(=O)(=O)c1cnc2ccccc2c1] | N-Hydroxy-3-methyl-2-[(3-methyl-butyl)-(quinoline-3-sulfonyl)-amino]-butyramide | 6.91 | 0.361 | 393.51 | 394 (M + 1) |
| 77 | 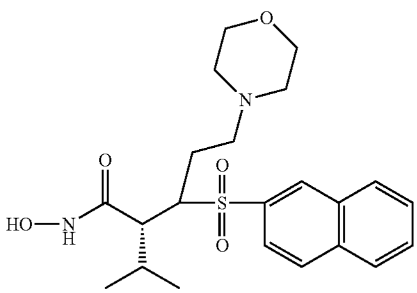 [SMILES: CC(C)[C@H](C(=O)NO)C(CCN1CCOCC1)S(=O)(=O)c1ccc2ccccc2c1] | N-Hydroxy-3-methyl-2-[(2-morpholin-4-yl-ethyl)-(naphthalene-2-sulfonyl)-amino]-butyramide | 0.144 | 0.0183 | 435.55 | 434.54 (M − 1) |
| 78 | 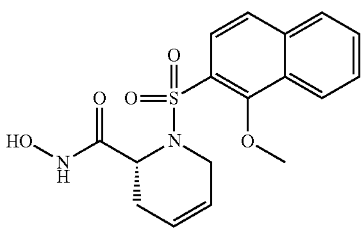 [SMILES: COc1c(S(=O)(=O)N2CC=CC[C@@H]2C(=O)NO)ccc2ccccc12] | 1-(1-Methoxy-naphthalene-2-sulfonyl)-1,2,3,6-tetrahydro-pyridine-2-carboxylic acid hydroxyamide | 0.0199 | 0.0021 | 362.41 | 363 (M + 1) |
| 79 | 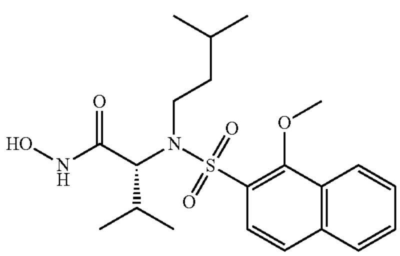 [SMILES: COc1c(S(=O)(=O)N(CCC(C)C)[C@@H](C(=O)NO)C(C)C)ccc2ccccc12] | N-Hydroxy-2-[(1-methoxy-naphthalene-2-sulfonyl)-(3-methyl-butyl)-amino]-3-methyl-butyramide | 0.0518 | 0.0011 | 422.55 | 423 (M + 1) |
| 80 | 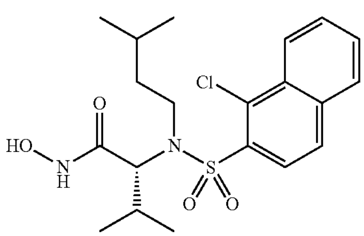 [SMILES: CC(C)CCN([C@@H](C(=O)NO)C(C)C)S(=O)(=O)c1ccc2ccccc2c1Cl] | 2-[(1-Chloro-naphthalene-2-sulfonyl)-(3-methyl-butyl)-amino]-N-hydroxy-3-methyl-butyramide | 0.779 | 0.118 | 426.97 | 425 (M − 1) |
| 81 | 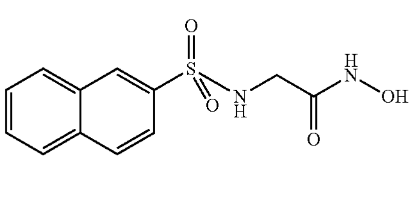 [SMILES: O=C(CNS(=O)(=O)c1ccc2ccccc2c1)NO] | N-Hydroxy-2-(naphthalene-2-sulfonylamino)-acetamide | 0.199 | 0.395 | 280.3 | 281.0 (M + 1) |

-continued

| # | Structure Name | MMP2 IC$_{50}$ [μM] | MMP13 IC$_{50}$ [μM] | MW (Calc'd) | LCMS |
|---|---|---|---|---|---|
| 82 | 4-{Hydroxycarbamoyl-[(3-methyl-butyl)-(naphthalene-2-sulfonyl)-amino]-methyl}-piperidine-1-carboxylic acid tert-butyl ester | <0.0003 | <0.0003 | 533.69 | 532.4 (M − 1) |
| 83 | 7-(Naphthalene-2-sulfonyl)-7-aza-bicyclo[4.2.1]nonane-8-carboxylic acid hydroxyamide | 0.770 | 0.135 | 374.46 | 373.0 (M − 1) |
| 84 | 2-[(7-Amino-naphthalene-2-sulfonyl)-(3-methyl-butyl)-amino]-N-hydroxy-3-methyl-butyramide | >1 | 0.0521 | 407.54 | 406.3 (M − 1) |
| 85 | N-Hydroxy-3-methyl-2-[(3-methyl-butyl)-(7-methyl-naphthalene-2-sulfonyl)-amino]-butyramide | 3.35 | 0.134 | 406.55 | 405.3 (M − 1) |
| 86 | N-Hydroxy-3-methyl-2-[[7-(3-methyl-butoxy)-naphthalene-2-sulfonyl]-(3-methyl-butyl)-amino]-butyramide | >10 | 3.25 | 478.66 | 479 (M + 1) |

| # | Structure Name | MMP2 IC$_{50}$ [µM] | MMP13 IC$_{50}$ [µM] | MW (Calc'd) | LCMS |
|---|---|---|---|---|---|
| 87 | N-Hydroxy-3-methyl-2-[(3-methyl-butyl)-(6-propoxy-naphthalene-2-sulfonyl)-amino]-butyramide | 0.197 | 0.0098 | 450.61 | 449.36 (M − 1) |
| 88 | 1-(Naphthalene-2-sulfonyl)-2,3,6,7-tetrahydro-1H-azepine-2-carboxylic acid hydroxyamide | 0.0635 | 0.0162 | 346.41 | 347 (M + 1) |
| 89 | 3,N-Dihydroxy-2-[(3-methyl-butyl)-(naphthalene-2-sulfonyl)-amino]-butyramide | 0.111 | 0.0032 | 394.49 | 395 (M + 1) |
| 90 | 2,2-Dimethyl-4-(naphthalene-2-sulfonyl)-thiomorpholine-3-carboxylic acid hydroxyamide | 0.0507 | <0.0003 | 380.49 | 379.3 (M − 1) |
| 91 | 2-(Naphthalene-2-sulfonyl)-2-aza-bicyclo[2.2.2]octane-3-carboxylic acid hydroxyamide | 22.2 | 6.95 | 360.44 | 359.4 (M − 1) |
| 92 | N-Hydroxy-3,3-dimethyl-2-(quinoline-6-sulfonylamino)-butyramide | 0.765 | 0.225 | 337.40 | 338 (M + 1) |

-continued

| # | Structure | Structure Name | MMP2 IC$_{50}$ [μM] | MMP13 IC$_{50}$ [μM] | MW (Calc'd) | LCMS |
|---|---|---|---|---|---|---|
| 93 | 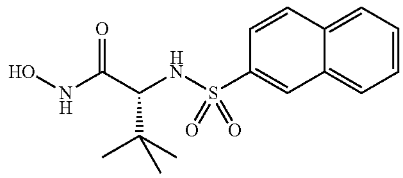 [SMILES: CC(C)(C)[C@@H](NS(=O)(=O)c1ccc2ccccc2c1)C(=O)NO] | N-Hydroxy-3,3-dimethyl-2-(naphthalene-2-sulfonylamino)-butyramide | 0.6 | 0.09 | 336.41 | 335 (M − 1) |
| 94 | 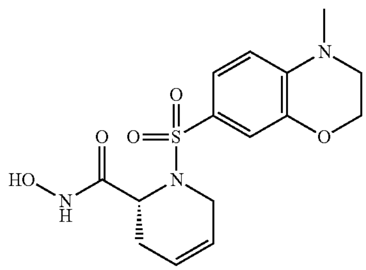 [SMILES: CN1CCOc2cc(S(=O)(=O)N3CC=CC[C@@H]3C(=O)NO)ccc21] | (R)-1-(4-Methyl-3,4-dihydro-2H-benzo[1,4]oxazine-7-sulfonyl)-1,2,3,6-tetrahydro-pyridine-2-carboxylic acid hydroxyamide | | 0.037 | 353.40 | 354 (M + 1) |
| 95 | 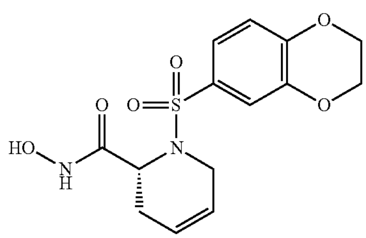 [SMILES: O=C(NO)[C@H]1CC=CCN1S(=O)(=O)c1ccc2c(c1)OCCO2] | (R)-1-(2,3-Dihydro-benzo[1,4]dioxine-6-sulfonyl)-1,2,3,6-tetrahydro-pyridine-2-carboxylic acid hydroxyamide | | 0.0026 | 342.37 | 341 (M − 1) |
| 96 | 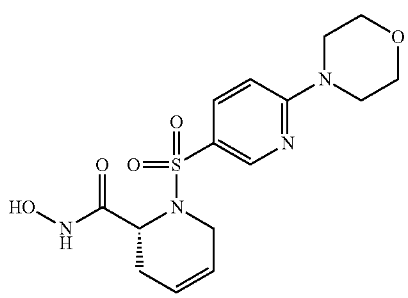 [SMILES: O=C(NO)[C@H]1CC=CCN1S(=O)(=O)c1ccc(N2CCOCC2)nc1] | (R)-1-(6-Morpholin-4-yl-pyridine-3-sulfonyl)-1,2,3,6-tetrahydro-pyridine-2-carboxylic acid hydroxyamide | | 0.326 | 368.4 | 369 (M + 1) |
| 97 | 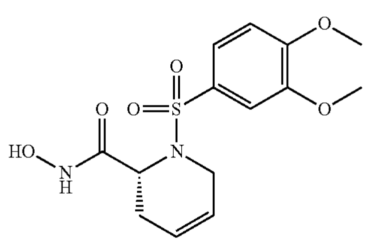 [SMILES: COc1ccc(S(=O)(=O)N2CC=CC[C@@H]2C(=O)NO)cc1OC] | (R)-1-(3,4-Dimethoxy-benzenesulfonyl)-1,2,3,6-tetrahydro-pyridine-2-carboxylic acid hydroxyamide | | 10.2 | 342.3 | 343 (M + 1) |
| 98 | 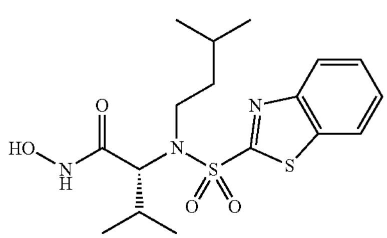 [SMILES: CC(C)CCN([C@@H](C(=O)NO)C(C)C)S(=O)(=O)c1nc2ccccc2s1] | (R)-2-[(Benzothiazole-2-sulfonyl)-(3-methyl-butyl)-amino]-N-hydrox-3-methyl-butyramide | 0.713 | 0.063 | 399.53 | 400 (M + 1) |

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

We claim:

1. A compound or salt thereof selected from the group consisting of:
   (R)—N-Hydroxy-2-[(1-hydroxy-naphthalene-2-sulfonyl)-(3-methyl-butyl)-amino]-3-methyl-butyramide;
   2-[Benzyl-(7-ethoxy-naphthalene-2-sulfonyl)-amino]-N-hydroxy-3-methyl-butyramide;
   N-isoamyl-N-(6-ethyl naphthalene-2-sulfonyl)-D-valine hydroxamic acid;
   N-Hydroxy-2-[(6-hydroxy-naphthalene-2-sulfonyl)-(3-methyl-butyl)-amino]-3-methyl-butyramide;
   2-[(6-Amino-naphthalene-2-sulfonyl)-(3-phenyl-propyl)-amino]-N-hydroxy-3-methyl-butyramide;
   2-[(6-Acetylamino-naphthalene-2-sulfonyl)-(3-phenyl-propyl)-amino]-N-hydroxy-3-methyl-butyramide;
   N-isoamyl-N-(6-methoxy naphthalene-2-sulfonyl)-D-valine hydroxamic acid;
   N-isoamyl-N-(6-hydroxy naphthalene-2-sulfonyl)-D-valine hydroxamic acid;
   2-[(7-Amino-naphthalene-2-sulfonyl)-(3-phenyl-propyl)-amino]-N-hydroxy-3-methyl-butyramide;
   (R)—N-Hydroxy-2-[(7-methoxy-naphthalene-2-sulfonyl)-(3-methyl-butyl)-amino]-3-methyl-butyramide;
   2-[(6-Ethoxy-naphthalene-2-sulfonyl)-(3-methyl-butyl)-amino]-N-hydroxy-3-methyl-butyramide;
   2-[Benzyl-(6-p-tolylamino-naphthalene-2-sulfonyl)-amino]-N-hydroxy-3-methyl-butyramide;
   N-Hydroxy-3-methyl-2-[[6-(3-methyl-butoxy)-naphthalene-2-sulfonyl]-(3-methyl-butyl)-amino]-butyramide;
   2-[(7-Ethoxy-naphthalene-2-sulfonyl)-(3-methyl-butyl)-amino]-N-hydroxy-3-methyl-butyramide;
   N-Hydroxy-2-[(6-isobutoxy-naphthalene-2-sulfonyl)-(3-methyl-butyl)-amino]-3-methyl-butyramide;
   2-[(6-Amino-naphthalene-2-sulfonyl)-(3-methyl-butyl)-amino]-N-hydroxy-3-methyl-butyramide;
   2-[(6-Benzyloxy-naphthalene-2-sulfonyl)-(3-methyl-butyl)-amino]-N-hydroxy-3-methyl-butyramide;
   2-[(6-Acetylamino-naphthalene-2-sulfonyl)-(3-methyl-butyl)-amino]-N-hydroxy-3-methyl-butyramide;
   N-Hydroxy-3-methyl-2-{(3-methyl-butyl)-[7-(3-methyl-butylamino)-naphthalene-2-sulfonyl]-amino}-butyramide;
   2-[(7-Acetylamino-naphthalene-2-sulfonyl)-(3-methyl-butyl)-amino]-N-hydroxy-3-methyl-butyramide;
   2-[(6-Allyloxy-naphthalene-2-sulfonyl)-(3-methyl-butyl)-amino]-N-hydroxy-3-methyl-butyramide;
   2-[(7-Ethoxy-naphthalene-2-sulfonyl)-pyridin-3-ylmethyl-amino]-N-hydroxy-3-methyl-butyramide;
   (R)—N-Hydroxy-2-[(1-methoxy-naphthalene-2-sulfonyl)-(3-methyl-butyl)-amino]-3-methyl-butyramide;
   2-[(1-Chloro-naphthalene-2-sulfonyl)-(3-methyl-butyl)-amino]-N-hydroxy-3-methyl-butyramide;
   2-[(7-Amino-naphthalene-2-sulfonyl)-(3-methyl-butyl)-amino]-N-hydroxy-3-methyl-butyramide;
   N-isoamyl-N-(6-methyl naphthalene-2-sulfonyl)-D-valine hydroxamic acid;
   (R)—N-Hydroxy-3-methyl-2-[[7-(3-methyl-butoxy)-naphthalene-2-sulfonyl]-(3-methyl-butyl)-amino]-butyramide; and
   N-Hydroxy-3-methyl-2-[(3-methyl-butyl)-(6-propoxy-naphthalene-2-sulfonyl)-amino]-butyramide.

2. A pharmaceutical composition comprising a therapeutically effective amount of a compound of claim 1 and one or more pharmaceutically acceptable carriers.

* * * * *